(12) United States Patent
Soubrier

(10) Patent No.: US 7,364,894 B2
(45) Date of Patent: Apr. 29, 2008

(54) CIRCULAR DNA MOLECULE HAVING A CONDITIONAL ORIGIN OF REPLICATION, PROCESS FOR THEIR PREPARATION AND THEIR USE IN GENE THERAPY

(75) Inventor: Fabienne Soubrier, Thiais (FR)

(73) Assignee: Centelion (FR)

( * ) Notice: Subject to any disclaimer, the term of this patent is extended or adjusted under 35 U.S.C. 154(b) by 316 days.

(21) Appl. No.: 10/684,830

(22) Filed: Oct. 15, 2003

(65) Prior Publication Data
US 2004/0142452 A1 Jul. 22, 2004

(51) Int. Cl.
| | | |
|---|---|---|
| C12N 1/21 | (2006.01) | |
| C12N 15/00 | (2006.01) | |
| C12N 15/70 | (2006.01) | |
| C12N 15/74 | (2006.01) | |

(52) U.S. Cl. ............................. 435/252.3; 435/320.1
(58) Field of Classification Search ................. None
See application file for complete search history.

(56) References Cited

U.S. PATENT DOCUMENTS

| | | | | |
|---|---|---|---|---|
| 4,654,307 | A | 3/1987 | Morgan .................... | 435/253 |
| 4,761,367 | A | 8/1988 | Edgell et al. ................ | 435/6 |
| 5,434,065 | A | 7/1995 | Mahan et al. ............ | 435/172.3 |
| 5,510,099 | A | 4/1996 | Short et al. .................. | 424/9.2 |
| 5,656,481 | A | 8/1997 | Baetge et al. ............... | 435/325 |
| 5,693,622 | A | 12/1997 | Wolff et al. .................... | 514/44 |
| 5,700,657 | A | 12/1997 | Beaudry et al. ........... | 435/69.1 |
| 5,714,323 | A | 2/1998 | Ohshima et al. ............... | 435/6 |
| 5,773,246 | A | 6/1998 | Keene et al. ............... | 435/69.1 |
| 5,851,808 | A | 12/1998 | Elledge et al. | |
| 5,859,208 | A | 1/1999 | Fiddes et al. ............... | 530/399 |
| 5,874,259 | A | 2/1999 | Szybalski | |
| 5,955,056 | A | 9/1999 | Short et al. ................... | 424/9.2 |
| 5,985,644 | A | 11/1999 | Roseman et al. ......... | 435/252.3 |
| 6,254,874 | B1 | 7/2001 | Mekalanos et al. ...... | 424/234.1 |
| 6,573,100 | B1 | 6/2003 | Seeber et al. ............... | 435/455 |

FOREIGN PATENT DOCUMENTS

| | | |
|---|---|---|
| WO | WO 95/30762 | 11/1995 |
| WO | WO 96/01899 | 1/1996 |

OTHER PUBLICATIONS

Bergemann, J., et al., "Excision of specific DNA-sequences from integrated retroviral vectors via site-specific recombination," *Nucleic Acids Research*, 1995, 23(21):4451-4456.
Gage, P. J., et al., "A Cell-Free Recombination System for Site-Specific Integration of Multigenic Shuttle Plasmids into the Herpes Simplex Virus Type 1 Genome," *Journal of Virology*, 1992, 66(9):5509-5515.
Hanzlik, A. J., et al., "A small plasmid for recombination-based screening," *Gene*, 1992, 122:171-174.
Kelley, W. L., et al., Conformation Changes Induced by Integration Host Factor at Origin γ of R6K and Copy Number Control, *The Journal of Biological Chemistry*, 1991, 266(24):15924-15937.
Metzger, D., et al., "Conditional site-specific recombination in mammalian cells using a ligand-dependent chimeric Cre recombinase," *Proc. Natl. Acad. Sci. USA*, 1995, 92:6991-6995.
Stewart, G. D., et al., "Plasmids for recombination-based screening," *Gene*, 1991, 106:97-101.
W. French Anderson, Human gene therapy, Nature, vol. 392, pp. 25-28, Apr. 30, 1998.
Dalyot et al., Efficient Transfer Of The Complete Human Beta-Globin Gene Into Human And Mouse Hemopoeitic Cells Via SV40 Pseudovirions, Gene Transfer & Gene Therapy 47-56 (1989).
Filutowicz et al., J. Cell Sci. Suppl. 7, 15-31, 1987.
Flensburg et al., J. Mol. Biol. 195:439-445, 1987.
Gluzman, SV40-Transformed Simian Cells Support the Replication of Early SV40 Mutants, Cell, 23:175-182 (1981).
Herrero et al., Transposon Vectors Containing Non-Antibiotic Resistance Selection Markers for Cloning and Stable Chromosomal Insertion of Foreign Genes in Gram-Negative Bacteria, Journal of Bacteriology, 172(11):6557-6567 (1990).
Inuzuka et al., An initiator protein for plasmid R6K DNA replication Mutations affecting the copy-number control, FEBS Letters 228(1):7-11 (1988).
Larsen et al., Low-copy-number plasmid-cloning vectors amplifiable by derepression of an inserted foreign promoter, Gene 28:45-54 (1984).
Metcalf et al., Use of the rep technique for allele replacement to construct new *Escherichia coli* hosts for maintenance of R6Kγ origin plasmids at different copy numbers, Gene 138:1-7 (1994).
Posfai et al., NAR 22(12):2392-2398, 1994.
Rusconi et al., A novel expression assay to study transcriptional activators, Gene 89:211-221 (1990).
June Rothman Scott, "Regulation of Plasmid Replication," *Microbiological Reviews*, Mar. 1984, vol. 48, No. 1, p. 1-23.
Summers et al., Multimerization of High Copy Number Plasmids Causes Instability: ColE1 Encodes a Determinant Essential for Plasmid Monomerization and Stability, Cell 36:1097-1103 (1984).
Vasavada et al., A contingent replication assay for the detection of protein-protein interactions in animal cells, Proc. Natl. Acad. Sci., USA 88:10686-10690 (1991).
Winnacker, E.L., *From Genes to Clones*, pp. 132-138, 1987.
Baum et al., "Novel Cloning Vectors for *Bacillus thuringiensis*," *Applied and Environmental Microbiology*, Nov. 1990, vol. 56, No. 11, pp. 3420-3428.
Koons et al., "Characterization of p*Pvu*1, the autonomous plasmid from *Proteus vulgaris* that carries the genes of the *Pvu*II restriction-modification system," Gene, 157:73-79, 1995.
Penfold et al., "An improved suicide vector for construction of chromosomal insertion mutations in bacteria," Gene, 18:145-146, 1992.

*Primary Examiner*—Nancy Vogel
(74) *Attorney, Agent, or Firm*—Finnegan, Henderson, Farabow, Garrett & Dunner, LLP

(57) ABSTRACT

A prokaryotic recombinant host cell comprising a heterologous replication initiation protein that activates a conditional origin of replication and an extrachromosomal DNA molecule comprising a heterologous therapeutic gene and a conditional origin of replication whose functionality in the prokaryotic recombinant host cell requires a replication initiating protein which is foreign to the host cell is described. The host cell may comprise a pir gene having at least one mutation, which may occur in the pir gene copy number control region, the pir gene leucine zipper-like motif, or the pir gene DNA binding region.

22 Claims, 30 Drawing Sheets

(SEQ ID NO: 21)

```
      Met Arg Leu Lys Val Met Met Asp Val Asn Lys Lys Thr Lys Ile Arg His Arg
  1   ATG AGA CTC AAG GTC ATG ATG GAC GTG AAC AAA AAA ACG AAA ATT CGC CAC CGA

Asn Glu Leu Asn His Thr Leu Ala Gln Leu Pro Leu Pro Ala Lys Arg Val Met
 55   AAC GAG CTA AAT CAC ACC CTG GCT CAA CTT CCT TTG CCC GCA AAG CGA GTG ATG

Tyr Met Ala Leu Ala Leu Ile Asp Ser Lys Glu Pro Leu Glu Arg Gly Arg Val
109   TAT ATG GCC CTT CGT CTC ATC GAT AGC AAA GAA CCT CTT GAA CGA GGG CGA GTT

Phe Lys Ile Arg Ala Glu Asp Leu Ala Ala Leu Ala Lys Ile Thr Pro Ser Leu
163   TTC AAA ATT AGG GCT GAA GAC CTT GCA GCG CTC GCC AAA ATC ACC CCA TCG CTT

Ala Tyr Arg Gln Leu Lys Glu Gly Gly Lys Leu Lue Gly Ala Ser Lys Ile Ser
217   GCT TAT CGA CAA TTA AAA GAG GGT GGT AAA TTA CTT GGT GCC AGC AAA ATT TCG

Leu Arg Gly Asp Asp Ile Ile Ala Leu Ala Lys Glu Leu Asn Leu Leu Phe Thr
271   CTA AGA GGG GAT GAT ATC ATT GCT TTA GCT AAA GAG CTT AAC CTG CTC TTT ACT

Ala Lys Asn Ser Pro Glu Glu Leu Asp Leu Asn Ile Ile Glu Trp Ile Ala Tyr
325   GCT AAA AAC TCC CCT GAA GAG TTA GAT CTT AAC ATT ATT GAG TGG ATA GCT TAT

Ser Asn Asp Glu Gly Tyr Leu Ser Leu Lys Phe Thr Arg Thr Ile Glu Pro Tyr
379   TCA AAT GAT GAA GGA TAC TTG TCT TTA AAA TTC ACC AGA ACC ATA GAA CCA TAT

Ile Ser Ser Leu Ile Gly Lys Lys Asn Lys Phe Thr Thr Gln Leu Leu Thr Ala
433   ATC TCT AGC CTT ATT GGG AAA AAA AAT AAA TTC ACA ACG CAA TTG TTA ACG GCA

Ser Leu Arg Leu Ser Ser Gln Tyr Ser Ser Ser Leu Tyr Gln Leu Ile Arg Lys
487   AGC TTA CGC TTA AGT AGC CAG TAT TCA TCT TCT CTT TAT CAA CTT ATC AGG AAG

His Tyr Ser Asn Phe Lys Lys Lys Asn Tyr Phe Ile Ile Ser Val Asp Glu Leu
541   CAT TAC TCT AAT TTT AAG AAG AAA AAT TAT TTT ATT ATT TCC GTT GAT GAG TTA
```

FIG. 12.1

```
       Lys Glu Glu Leu Ile Ala Tyr Thr Phe Asp Lys Asp Gly Asn Ile Glu Tyr Lys
   595 AAG GAA GAG TTA ATA GCT TAT ACT TTT GAT AAA GAT GGA AAT ATT GAG TAC AAA

Tyr Pro Asp Phe Pro Ile Phe Lys Arg Asp Val Leu Asn Lys Ala Ile Ala Glu
   649 TAC CCT GAC TTT CCT ATT TTT AAA AGG GAT GTG TTA AAT AAA GCC ATT GCT GAA

Ile Lys Lys Lys Thr Glu Ile Ser Phe Val Gly Phe Thr Val His Glu Lys Glu
   703 ATT AAA AAG AAA ACA GAA ATA TCG TTT GTT GGC TTC ACT GTT CAT GAA AAA GAA

Gly Arg Lys Ile Ser Lys Leu Lys Phe Glu Phe Val Val Asp Glu Asp Glu Phe
   757 GGA AGA AAA ATT AGT AAG CTG AAG TTC GAA TTT GTC GTT GAT GAA GAT GAA TTT

Ser Gly Asp Lys Asp Asp Glu Ala Phe Phe Met Asn Leu Ser Glu Ala Asp Ala
   811 TCT GGC GAT AAA GAT GAT GAA GCT TTT TTT ATG AAT TTA TCT GAA GCT GAT GCA

Ala Phe Leu Lys Val Phe Asp Glu Thr Val Pro Pro Lys Lys Ala Lys Gly ***
   865 GCT TTT CTC AAG GTA TTT GAT GAA ACC GTA CCT CCC AAA AAA GCT AAG GGG TGA
```

FIG. 12.2

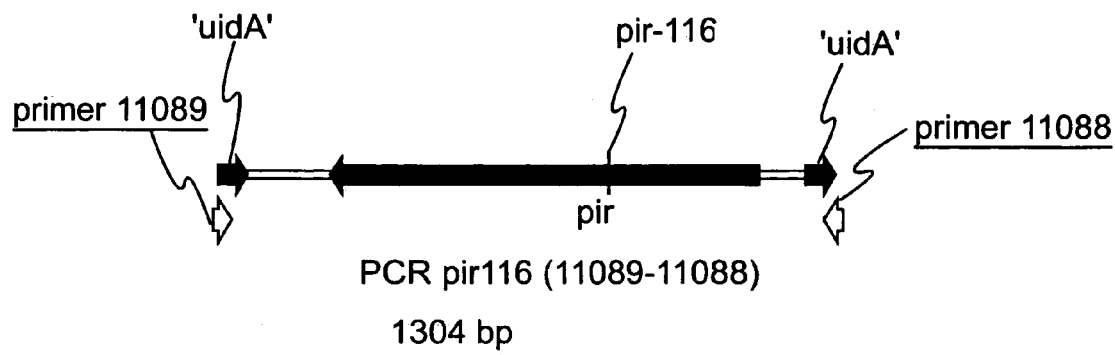
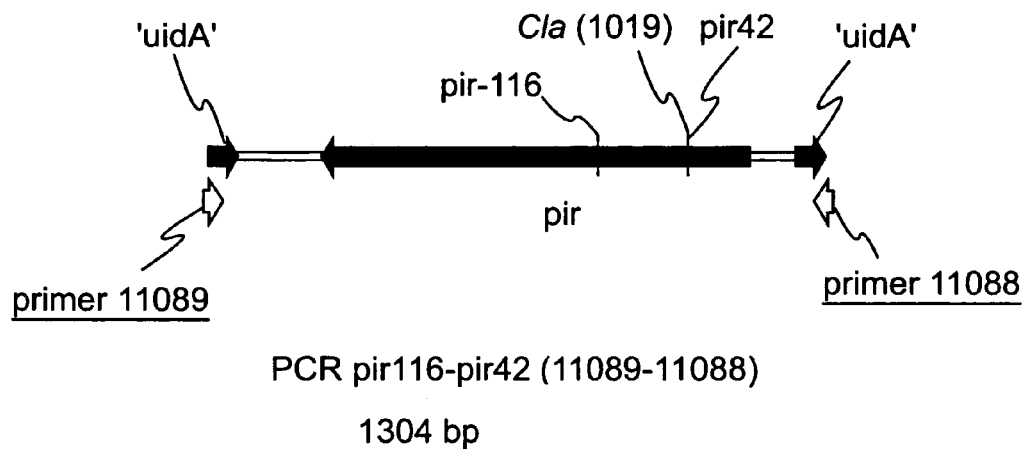
FIG. 14

M: 1 kb LADDER (LIFE BIOTECHNOLOGIES)
1->4: TEX1*cop*21 (pXL2979)
5->8: XAC1*pir* (pXL2979)
9->12: TEX1 (pXL2979)

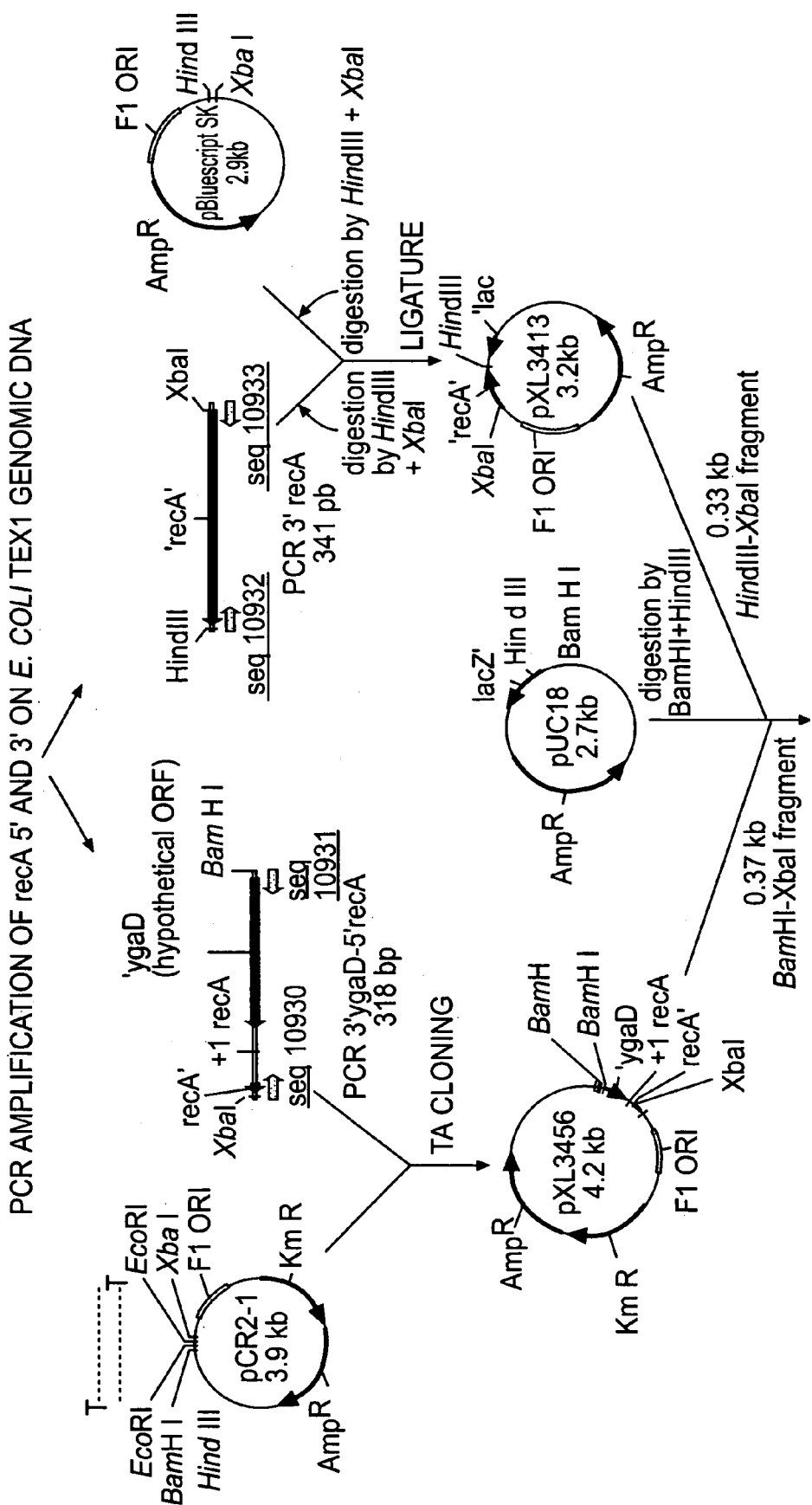
FIG. 18.1

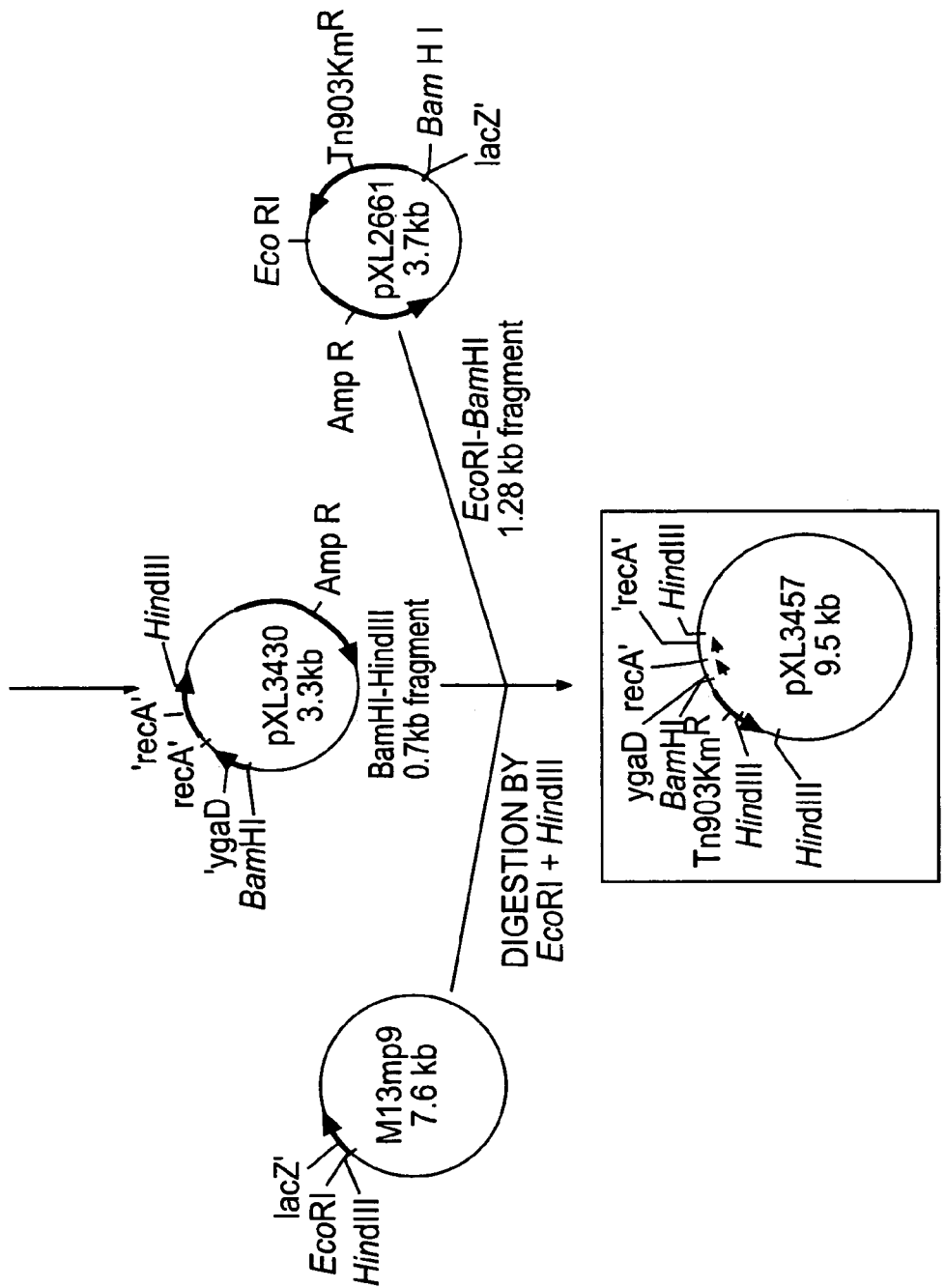
FIG. 18.2

A: SUPERCOILED DNA LADDER (PROMEGA)
B: pXL3179 IN TEX2 *pir42*
C: pXL3179 IN TEX1 *pir42*
D: pXL3179 IN TEX1

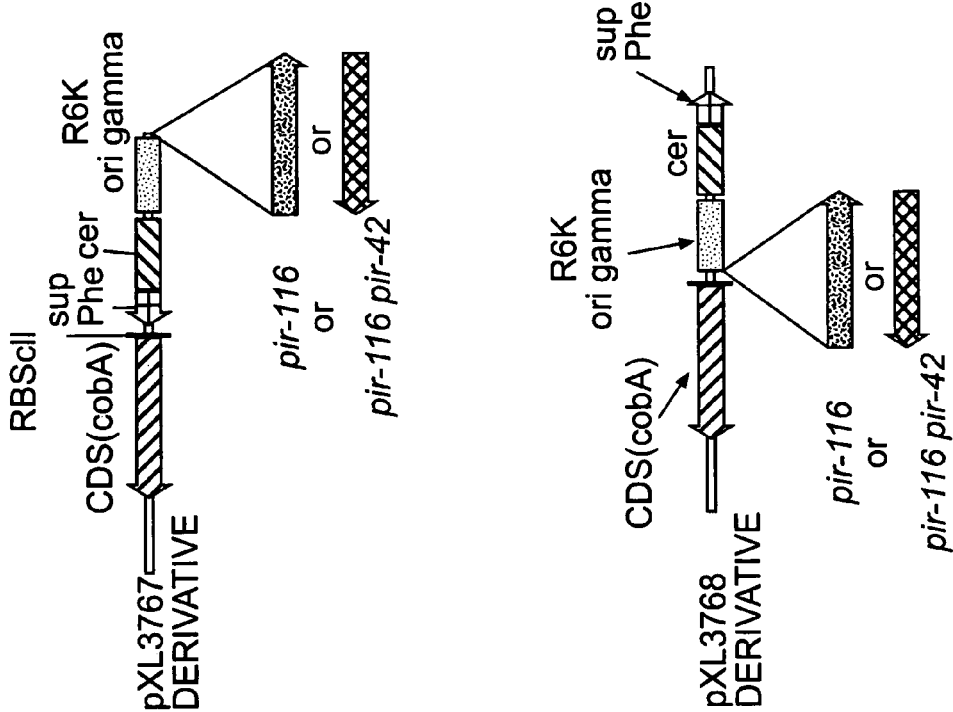
*FIG. 23*
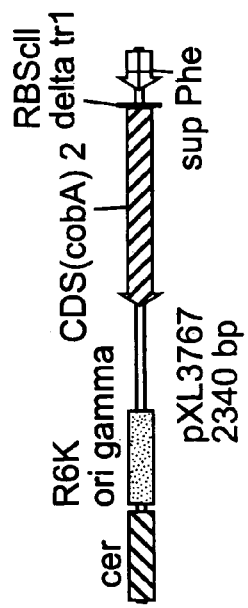
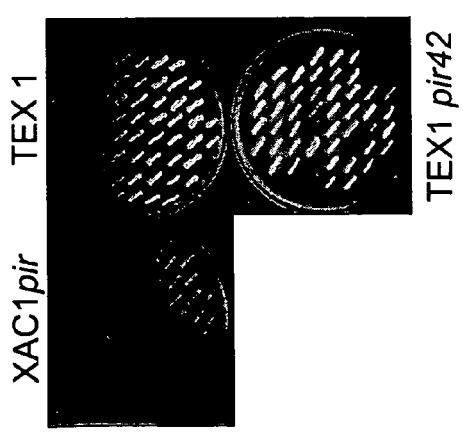
*FIG. 22*

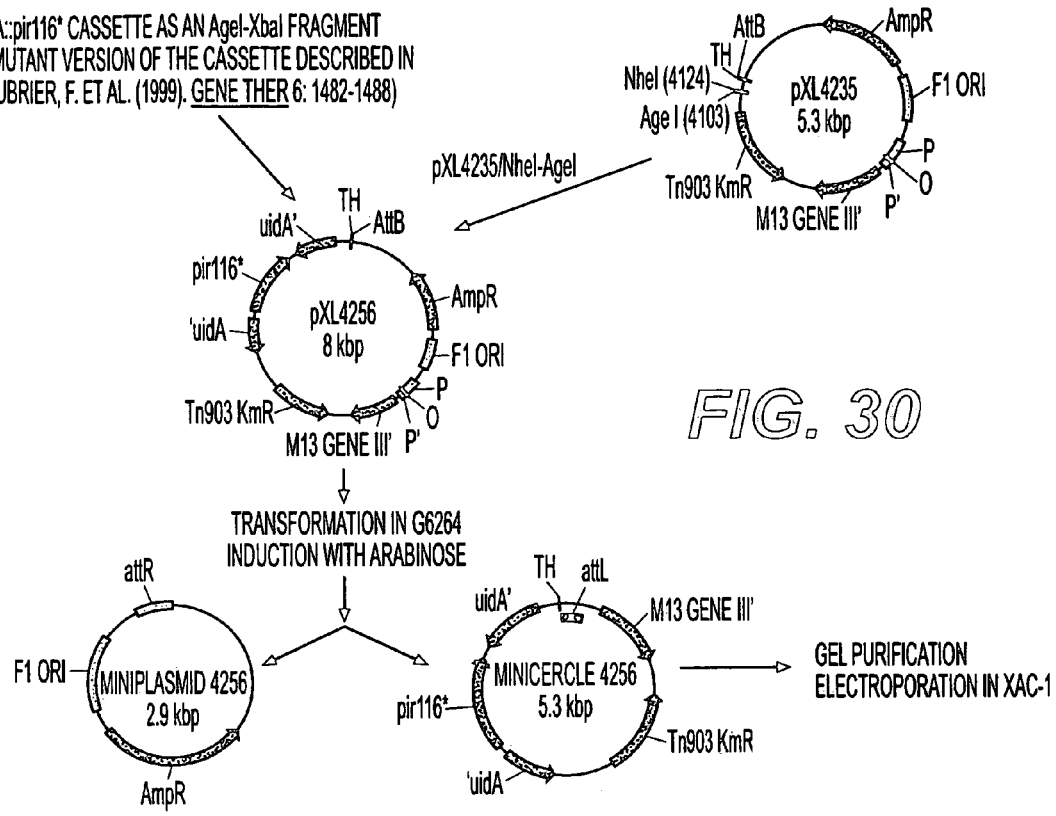
FIG. 30
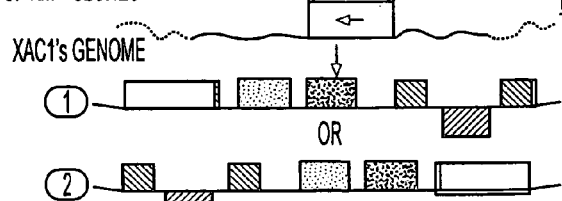
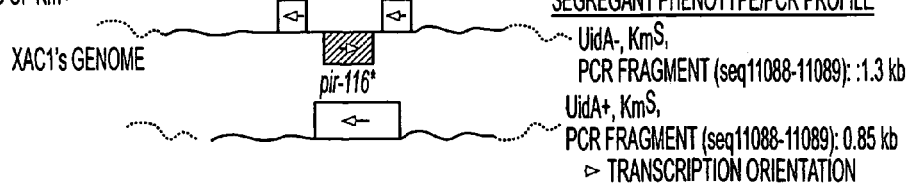
FIG. 31

CIRCULAR DNA MOLECULE HAVING A CONDITIONAL ORIGIN OF REPLICATION, PROCESS FOR THEIR PREPARATION AND THEIR USE IN GENE THERAPY

The present invention relates to a novel conditional replication DNA molecule which can be used in gene therapy or for the production of recombinant proteins. The novel DNA molecules according to the present invention are designated pCOR™ herein after.

Gene therapy consists in correcting a deficiency or an anomaly by introducing genetic information into the affected organ or cell. This information may be introduced either in vitro into a cell extracted from the organ and then reinjected into the body, or in vivo, directly into the target tissue. As a molecule of high molecular weight and of negative charge, DNA has difficulty in spontaneously crossing phospholipid cell membranes. Various vectors are thus used in order to enable gene transfer to take place: viral vectors, on the one hand, and natural or synthetic chemical and/or biochemical vectors, on the other hand.

Viral vectors (retroviruses, adenoviruses, adeno-associated viruses, etc.) are very effective, in particular for crossing membranes, but present a certain number of risks such as pathogenicity, recombination, replication, and immunogenicity.

Chemical and/or biochemical vectors allow these risks to be avoided (for reviews, see Behr, 1993, Cotten and Wagner 1993). These are, for example, cations (calcium phosphate, DEAE-dextran, etc.) which act by forming precipitates with DNA, which may be "phagocytosed" by the cells. They may also be liposomes in which the DNA is incorporated and which fuse with the plasma membrane. Synthetic gene-transfer vectors are generally lipids or cationic polymers which complex the DNA and form with it a particle bearing positive surface charges. As illustrations of vectors of this type, mention may be made in particular of dioctadecyla-midoglycylspermine (DOGS, Transfectam™) or N-[1-(2,3-dioleyloxy)propyl]-N,N,N-trimethylammonium (DOTMA, Lipofectin™).

However, the use of chemical and/or biochemical vectors or naked DNA implies the possibility of producing large amounts of DNA of pharmacological purity. The reason for this is that in gene therapy techniques, the medicinal product consists of the DNA itself and it is essential to be able to manufacture, in suitable amounts, DNAs having properties which are appropriate for therapeutic use in man.

In the case of non-viral vectorology, the vectors used are plasmids of bacterial origin. The plasmids generally used in gene therapy carry (i) an origin of replication, (ii) a marker gene such as a gene for resistance to an antibiotic (kanamycin, ampicillin, etc.) and (iii) one or more transgenes with sequences necessary for their expression (enhancer(s), promoter(s), polyadenylation sequences, etc.). However, the technology currently available is not entirely satisfactory.

On the one hand, the risk remains of dissemination in the body. Thus, a bacterium which is present in the body can, at low frequency, receive this plasmid. There is a greater likelihood of this taking place if it involves an in vivo gene therapy treatment in which the DNA may be disseminated in the body of the patient and may come into contact with bacteria which infect this patient or bacteria of the commensal flora. If the bacterium receiving the plasmid is an enterobacterium, such as *E. coli*, this plasmid can be replicated. Such an event then leads to dissemination of the therapeutic gene. Insofar as the therapeutic genes used in gene therapy treatments can code, for example, for a lymphokine, a growth factor, an anti-oncogene or a protein whose function is defective in the host and which thus makes it possible to correct a genetic defect, the dissemination of some of these genes could have unforeseeable and worrying effects (for example if a pathogenic bacterium acquired a human growth factor gene).

On the other hand, the plasmids generally used in non-viral gene therapy also possess a marker for resistance to an antibiotic (ampicillin, kanamycin, etc.). The bacterium acquiring such a plasmid thus has an undeniable selective advantage since any antibiotic therapy, using an antibiotic from the same family as that which selects the plasmid resistance gene, will lead to selection of the plasmid in question. In this respect, ampicillin belongs to the α-lactams, which is the family of antibiotics which is most frequently used worldwide. The use in bacteria of selection markers which are not antibiotic-resistance genes would thus be particularly advantageous. This would avoid the selection of bacteria which may have received a plasmid carrying such a marker.

It is thus particularly important to seek to limit the dissemination of therapeutic genes and resistance genes as much as possible.

The subject of the present invention is specifically to propose novel DNA molecules which can be used in gene therapy or for the production of recombinant proteins in vitro and which replicate only in cells which can complement certain functions of these non-viral vectors.

The invention also relates to a particularly effective method for preparing these DNA molecules.

The DNA molecules claimed have the advantage of removing the risks associated with dissemination of the plasmid, such as (1) replication and dissemination, which can lead to uncontrolled overexpression of the therapeutic gene, (2) dissemination and expression of resistance genes. The genetic information contained in the DNA molecules according to the invention effectively comprises the therapeutic gene(s) and the signals for regulating its (their) expression, a functional conditional origin of replication which greatly limits the host cell spectrum of this plasmid, a selection marker of reduced size which is preferably different from a gene which imparts resistance to an antibiotic and, where appropriate, a DNA fragment which allows the resolution of plasmid multimers. The probability of these molecules (and thus the genetic information which they contain) being transferred to a microorganism, and maintained stably, is very limited.

Lastly, the vectors according to the invention, also referred to as miniplasmids on account of their circular structure, their reduced size and their supercoiled form, have the following additional advantages: on account of their size which is reduced in comparison with the ColE1-derived plasmids used conventionally, the DNA molecules according to the invention potentially have better in vivo bioavailability, and the DNA molecules or pCOR stay in a stable extrachromosomal form in the host prokaryotic or eukaryotic cells that do not contain the initiating protein. In particular, they have improved capacities of cell penetration and distribution. Thus, it is acknowledged that the diffusion coefficient in tissues is inversely proportional to the molecular weight (Jain, 1987). Similarly, in the cell, high molecular weight molecules have poorer permeability across the plasma membrane. In addition, in order for the plasmid to pass into the nucleus, which is essential for its expression, the high molecular weight is also a disadvantage, the nuclear pores imposing a size limit for diffusion into the nucleus (Landford et al., 1986). The reduction in size of the non-therapeutic parts of the DNA molecule (origin of replication and selection gene in particular) according to the invention also makes it possible to decrease the size of the DNA molecules. The part which allows the replication and selection of this plasmid in the bacterium (1 kb) is decreased by a factor of 3, counting, for example, 3 kb for the origin of replication and the resistance marker vector part. This decrease (i) in molecular weight and (ii) in negative charge imparts improved tissue, cellular and nuclear bioavailability and diffusion to the molecules of the invention.

More precisely, the present invention relates to a circular DNA molecule, which is useful in gene therapy, this molecule comprising at least one nucleic acid sequence of interest, characterized in that the region which allows its replication comprises an origin of replication whose functionality in a host cell requires the presence of at least one specific protein which is foreign to the said host cell.

This DNA molecule may be in single- or double-stranded form and advantageously possesses a supercoiled form.

For the purposes of the present invention, the host cells used can be of various origins. They can be eukaryotic or prokaryotic cells. According to a preferred embodiment of the invention, they are prokaryotic cells.

The replication of bacterial plasmids conventionally requires the presence of at least one protein, which is coded for by the host cell, of the RNA polymerase, Rnase, DNA polymerase, etc. type. For the reasons already explained above, it is not possible to overcome entirely, with this type of replication, any possible risks of dissemination in the treated organism. Advantageously, the functionality of the origin of replication of the DNA molecule according to the invention requires the presence of a specific protein which is foreign to the host cell. The significance of this characteristic is to reduce the host spectrum of the claimed plasmid to specific strains that express this initiator protein. The DNA molecule developed within the context of the present invention thus advantageously possesses a so-called conditional origin of replication.

The conditional origin of replication used according to the present invention may originate from plasmids or bacteriophages which share the following characteristics: they contain in their origin of replication repeat sequences, or iterons, and they code for at least one replication-initiating protein (Rep) which is specific to them. By way of example, mention may be made of the conditional replication systems of the following plasmids and bacteriophages:

| plasmid or bacteriophage | specific initiator protein |
|---|---|
| RK2 (Stalker et al., 1981) | TrfA |
| R1 (Ryder et al., 1981) | RepA |
| pSC101 (Vocke and Bastia, 1983) | RepA |
| F (Murotsu et al., 1981) | protein E |
| Rts1 (Itoh et al., 1982, 1987) | RepA |
| RSF1010 (Miao et al., 1995) | RepC |
| P1 (Abeles et al., 1984) | RepA |
| P4 (Flensburg and Calendar, 1987) | alpha protein |
| lambda (Moore et al., 1981) | protein O |
| phi 82 (Moore et al., 1981) | protein O from phi 82 |
| phi 80 | protein O from phi 80 |

According to a preferred embodiment of the invention, the origin of replication used in the DNA molecules claimed is derived from a natural E. coli plasmid referred to as R6K.

The replication functions of R6K are grouped together in a 5.5 kbp DNA fragment (FIG. 1) comprising 3 origins of replication $\alpha$, $\beta$, and $\gamma$ ($\gamma$ and $\alpha$ providing 90% of the replication) and an operon coding for the $\Pi$ replication-initiator protein and the protein Bis. The minimum amount of genetic information required to maintain this plasmid at its characteristic number of copies (15 copies per genome) is contained in two elements: the 400 bp of ori $\gamma$ and the gene pir, whose product is the $\Pi$ initiator protein.

Ori $\gamma$ may be divided into two functional parts: the core part and the activator element (FIG. 1). The core part, which is essential for replication, contains the iterons (7 direct repeats of 22 bp) to which the $\Pi$ protein represented in SEQ ID No. 1 becomes bound, and flanking segments, which are targets of the host proteins (IHF, DnaA).

According to a preferred mode of the invention, the origin of replication of the vector claimed consists entirely or partially of this $\gamma$ origin of replication of the plasmid R6K and more preferably, entirely or partially of SEQ ID No. 1 or one of its derivatives.

The origin of replication described above, which has the advantage of being of very limited size, is functional solely in the presence of a specific initiator protein, protein Pi, produced by the gene pir (SEQ ID No. 2). Since this protein can act in trans, it is possible to physically dissociate the ori gamma from the pir gene, which may be introduced into the genome of the cell which is chosen as the specific host for these plasmids. Mutations in $\Pi$ may alter its inhibitory functions (Inuzuka and Wada, 1985) and lead to an increase in the number of copies of the R6K derivatives, up to more than 10 times the initial number of copies. These substitutions may be within a domain of 40 amino acids, which therefore appears to be responsible for the control by $\Pi$ of the number of plasmid copies (FIG. 2), or in other regions of the $\Pi$ protein.

According to an advantageous embodiment of the present invention, the $\Pi$ protein, expressed in the host cell, results from the expression of the gene represented in SEQ ID No. 2 or one of its derivatives as defined above and more particularly of the gene pir 116 which comprises a mutation when compared with the pir gene. This mutation corresponds to the replacement of a proline by a leucine at position 106 from the start codon. In this context, the number of copies of the R6K derivatives is about 250 copies per genome.

For the purposes of the present invention, the term derivative denotes any sequence which differs from the sequence considered, obtained by one or more modifications of genetic and/or chemical nature, as well as any sequence which hybridizes with these sequences or fragments thereof and whose product possesses the activity indicated with regard to the replication-initiator protein $\Pi$. The term modification of the genetic and/or chemical nature may be understood to refer to any mutation, substitution, deletion, addition and/or modification of one or more residues. The term derivative also comprises the sequences homologous with the sequence considered, derived from other cellular sources and in particular cells of human origin, or from other organisms, and possessing an activity of the same type. Such homologous sequences may be obtained by hybridization experiments. The hybridizations may be performed starting with nucleic acid libraries, using the native sequence or a fragment thereof as probe, under conventional conditions of stringency (Maniatis et al., cf. General techniques of molecular biology), or, preferably, under conditions of high stringency.

Besides a conditional origin of replication as defined above, the DNA molecules claimed contain a region comprising one (or more) gene(s) which make it possible to ensure selection of the DNA molecule in the chosen host.

This may be a conventional marker of gene type which imparts resistance to an antibiotic, such as kanamycin, ampicillin, chloramphenicol, streptomycin, spectinomycin, lividomycin or the like.

However, according to a preferred embodiment of the invention, this region is different from a gene which imparts resistance to an antibiotic. It may thus be a gene whose product is essential for the viability of the host envisaged, under defined culturing conditions. It may be, for example:

a gene coding for a suppressor tRNA, of natural or synthetic origin. This is, more preferably, an amber codon tRNA (TAG)

a gene whose product is necessary for metabolism of the cell, under certain culturing conditions, namely a gene involved in the biosynthesis of a metabolite (amino acid, vitamin, etc.), or a catabolism gene which makes it possible to assimilate a substance present in the culture medium (specific nitrogen or carbon source), etc.

According to a preferred mode of the invention, this region contains an expression cassette of a gene coding for a suppressor tRNA for specific codons. This latter may be chosen, in particular, from those coding for phenylalanine, cysteine, proline, alanine and histidine amino acids. It is more particularly a suppressor tRNA for amber codons (TAG).

In this particular case, the system used to select, in the host cells, the DNA molecules which are the subject of the present invention includes two elements: 1) on the DNA molecule, a gene coding for a suppressor transfer RNA for the amber codon (TAG) which constitutes the selection marker, known as (sup) gene and 2) a specific host, one of whose genes, which is essential under certain culture conditions, contains an amber TAG codon. This cell may grow, under the culture conditions for which the product of the gene containing the TAG codon is essential, only if the plasmid allowing the expression of sup is present in the cell. The culture conditions thus constitute the pressure for selection of the DNA molecule. The sup genes used may be of natural origin (Glass et al., 1982) or may originate from a synthetic construction (Normanly et al., 1986, Kleina et al., 1990).

Such a system offers great flexibility insofar as, depending on the gene containing an amber mutation, it is possible to determine various selective media. In the bacterium *Lactococcus lactis* for example, the amber codon is located in a purine biosynthesis gene. This allows the selection of the plasmid carrying the gene coding for the suppressor tRNA when the bacteria multiply in milk. Such a marker has the advantage of being very small and of containing no "foreign" sequences, originating from phages or transposons.

According to a particular embodiment of the invention, the DNA molecule also comprises a DNA fragment, the target for site-specific recombinases, which allows the resolution of plasmid multimers.

Thus, such a fragment, introduced on to a DNA molecule which is circular and whose origin of replication is, for example, ori gamma, allows the resolution of multimers of such a plasmid. Such multimers are observed, in particular, when the DNA molecule is prepared in a strain carrying a mutated allele of pir, such as pir116, which makes it possible to increase the number of copies of the R6K derivatives.

This recombination may be achieved by means of various systems which entail site-specific recombination between sequences. More preferably, the site-specific recombination of the invention is obtained by means of specific intramolecular recombination sequences which are capable of recombining with each other in the presence of specific proteins, generally referred to as recombinases. In this specific case, these are the recombinases XerC and XerD. For this reason, the DNA molecules according to the invention generally also comprise a sequence which allows this site-specific recombination. The specific recombination system present in the genetic constructions according to the invention (recombinases and specific recognition site) may be of different origins. In particular, the specific sequences and the recombinases used may belong to different structural classes, and in particular to the transposon Tn3 resolvase family or to the bacteriophage lambda integrase family. Among the recombinases belonging to the transposon Tn3 family, mention may be made in particular of the resolvase of transposon Tn3 or of transposons Tn21 and Tn522 (Stark et al., 1992); the Gin invertase of bacteriophage mu or alternatively plasmid resolvases, such as that of the par fragment of RP4 (Abert et al., Mol. Microbiol. 12 (1994) 131). Among the recombinases belonging to the bacteriophage λ integrase family, mention may be made in particular of the integrase of the phages lambda (Landy et al., Science 197 (1977) 1147), P22 and Φ80 (Leong et al., J. Biol. Chem. 260 (1985) 4468), HP1 of *Haemophilus influenzae* (Hauser et al., J. Biol. Chem. 267 (1992) 6859), the Cre integrase of phage P1, the integrase of plasmid pSAM2 (EP 350 341) or alternatively the FLP recombinase of the 2μ plasmid and the XerC and XerD recombinases from *E. coli*.

Preferably, the DNA molecules which form the subject of the present invention contain the fragment cer from the natural *E. coli* plasmid ColE1. The cer fragment used is a 382 bp HpaII fragment from ColE1 which has been shown to bring about, in cis, the resolution of plasmid multimers (Summers et al., 1984; Leung et al., 1985). It is also possible to use a HpaII-TaqI fragment of smaller size (280 bp) or a smaller fragment (about 220 bp), contained in the HpaII fragment, which fragments possess the same properties (Summers and Sherratt, 1988). This resolution takes place by way of a specific intramolecular recombination, which involves four proteins encoded by the genome of *E. coli*: ArgR, PepA, XerC and XerD (Stirling et al., 1988, 1989; Colloms et al., 1990, Blakely et al., 1993). It was found that insertion of the fragment cer from the natural *E. coli* plasmid ColE1 allows to obtain a high resolution of plasmids multimers, thereby resulting in high proportion of monomers in a reproducible manner. This is particularly unexpected as it has been shown that the insertion of the cer site into a minicircle which contains the ColE1 origin of replication from pBluescript SK+ did not result in efficient multimer resolution (Kreiss et al., Appl. Microbiol. Biotechnol, 49:560-567 (1998)), and thus effective resolution in cis of plasmids is unpredictable and seems to depend on the plasmid conformation. In the case of the pCOR plasmid, an effective cis resolution is reached when cer is present on the pCOR, thereby resulting in a unexpectedly high monomers of pCOR in a reproducible manner.

In this respect, it is particularly advantageous to use all or part of the cer fragment of ColE1 or one of its derivatives as defined above.

According to an implementation variant, the DNA molecules of the invention may also comprise a sequence capable of interacting specifically with a ligand. Preferably, this is a sequence capable of forming, by hybridization, a triple helix with a specific oligonucleotide. This sequence thus makes it possible to purify the molecules of the invention by selective hybridization with a complementary oligonucleotide immobilized on a support (see application WO 96/18744 and WO 02/07727). The sequence may be naturally present in the origin of replication of the plasmid as described in US publication application 2003/186268 of the Applicant, or naturally present in the transgene as described in WO 02/07727, and alternatively can be positioned at any site in the DNA molecule of the invention, provided that it does not affect the functionality of the gene of interest and of the origin of replication. Formation of a triple helix by hybridization thus occurs between the oligonucleotide and the specific complementary sequence present in the DNA. In this connection, to obtain the best yields and the best selectivity, an oligonucleotide and a specific sequence which are fully complementary are used in the method of the invention. These can be, in particular, an oligonucleotide poly(CTT) and a specific sequence poly(GAA). For example, oligonucleotides containing repeated motifs such as CTT are capable of forming a triple helix with a specific sequence containing complementary units (GAA). The sequence in question can, in particular, be a region containing 7, 14 or 17 GAA units, and in the oligonucleotides a corresponding numbers of repeat CTT. In this case, the oligonucleotide binds in an antiparallel orientation to the polypurine strand. These triple helices are stable only in the presence of $Mg^{2+}$ (Vasquez et al., Biochemistry, 34: 7243-7251 (1995); Beal and Dervan, Science, 251: 1360-1363 (1991)).

As stated above, the specific sequence can be a sequence naturally present in the pCOR, or may be a synthetic sequence introduced artificially in the latter. It is especially advantageous to use an oligonucleotide capable of forming a triple helix with a sequence naturally present in the pCOR, for example in the origin of replication of a plasmid or in a marker gene. The synthesis of oligonucleotides capable of forming triple helices with these natural homopurine-homopyrimidine regions is particularly advantageous, as it may be applied to unmodified pCOR plasmids. Particularly preferred target sequences which can form triplex structures with particular oligonucleotides have been identified in ColE1 and in pCOR origins of replication. ColE1-derived plasmids contain a 12-mer homopurine sequence (5'-AGAAAAAAAGGA-3') (SEQ ID NO: 33) mapped upstream of the RNA-II transcript involved in plasmid replication (Lacatena et al., Nature, 294: 623 (1981)). This sequence forms a stable triplex structure with the 12-mer complementary 5'-TCTTTTTTTCCT-3' (SEQ ID NO: 34) oligonucleotide. The pCOR backbone contains a homopurine stretch of 14 non repetitive bases (5'-AAGAAAAAAAGAA-3') (SEQ ID NO: 35) located in the A+T-rich segment of the γ origin replicon of pCOR (Levchenko et al., Nucleic Acids Res., 24:1936 (1996)). This sequence forms a stable triplex structure with the 14-mer complementary oligonucleotide 5'-TTCTTTTTTTTCT-3' (SEQ ID NO: 36). The corresponding oligonucleotides 5'-TCTTTTTTCCT-3' (SEQ ID NO: 37) and 5'-TTCTTTTTTTTCTT-3' (SEQ ID NO: 38) efficiently and specifically target their respective complementary sequences located within the origin of replication of either ColE1 ori or pCOR (oriγ). Also, use of an oligonucleotide capable of forming a triple helix with a sequence present in an origin of replication or a marker gene is especially advantageous, since it makes it possible, with the same oligonucleotide, to purify any DNA containing the said origin of replication or said marker gene. Hence it is not necessary to modify the plasmid or the double-stranded DNA in order to incorporate an artificial specific sequence in it.

Although fully complementary sequences are preferred, it is understood, however, that some mismatches may be tolerated between the sequence of the oligonucleotide and the sequence present in the DNA, provided they do not lead to too great a loss of affinity. The sequence 5'-AAAAAAGGGAATAAGGG-3' (SEQ ID NO: 39) present in the E. coli β-lactamase gene may be mentioned. In this case, the thymine interrupting the polypurine sequence may be recognized by a guanine of the third strand, thereby forming a G*TA triplet which it is stable when flanked by two T*AT triplets (Kiessling et al., Biochemistry, 31: 2829-2834 (1992)).

According to a particular embodiment, the oligonucleotides used may comprise the sequence $(CCT)_n$, the sequence $(CT)_n$ or the sequence $(CTT)_n$, in which n is an integer between 1 and 15 inclusive. It is especially advantageous to use sequences of the type $(CT)_n$ or $(CTT)_n$. Oligonucleotides may also combine (CCT), (CT) or (CTT) units.

The oligonucleotides used may be natural (composed of unmodified natural bases) or chemically modified. In particular, the oligonucleotide may advantageously possess certain chemical modifications enabling its resistance to or its protection against nucleases, or its affinity for the specific sequence, to be increased.

As a DNA molecule representative of the present invention, the plasmid pXL2774 and its derivatives may be claimed most particularly. For the purposes of the invention, the term derivative is understood to refer to any construction derived from pXL2774 and containing one or more genes of interest other than the luciferase gene. Mention may also be made of the plasmids pXL3029, pXL3030, and plasmid pXL3179 or NV1FGF containing an expression cassette of a therapeutic gene. In a most preferred embodiment, the invention relates to a pCOR comprising the FGFa or FGF-1 gene as described in U.S. Pat. No. 4,686,113 of the Applicant, which is designated pXL 3179 or NV1FGF.

The present invention also relates to the development of a process for the construction of specific host cells, which are particularly effective for the production of these therapeutic DNA molecules.

Another subject of the present invention relates to a process for the production of a circular DNA molecule, characterized in that a host cell is cultured containing at least one DNA molecule as defined above and a protein, which may or may not be expressed in situ, which conditions the functionality of the origin of replication of the said DNA molecule, which is specific and which is foreign to the said host cell, under conditions which allow the selection of host cells transformed by the said DNA molecules.

More preferably, the protein which conditions the functionality of the origin of replication of the DNA molecule is expressed in situ from a corresponding gene. The gene coding for the replication-initiating protein may be carried by a subsidiary replicon, which is compatible with the derivatives of the conditional origin of replication used or which may be introduced into the genome of the host cell by recombination, by means of a transposon, a bacteriophage or any other vector. In the particular case in which the gene expressing the protein is placed on a subsidiary replicon, the latter also contains a promoter region for functional transcription in the cell, as well as a region which is located at the 3' end and which specifies a transcription termination signal. As regards the promoter region, this may be a promoter region which is naturally responsible for expressing the gene under consideration when the latter is capable of functioning in the cell. It may also be a case of regions of different origin (responsible for expressing other proteins), or even of synthetic origin. In particular, it may be a case of promoter sequences for prokaryotic or bacteriophage genes. For example, it may be a case of promoter sequences obtained from the cell genome.

As genes coding for the replication-initiating protein, use may be made either of wild-type genes or of mutated alleles which make it possible to obtain an increased number of copies of the plasmids (or derivatives) specific for the initiator protein which conditions the functionality of the origin of replication used in the DNA molecule.

Such mutants have been described in particular for the plasmids R6K (Inuzuka and Wada, 1985; Greener et al., (1990), Rts1 (Terawaki and Itoh, 1985, Terawaki et al., 1990; Zeng et al., 1990), F (Seelke et al., 1982; Helsberg et al., 1985; Kawasaki et al., 1991), RK2 (Durland et al., 1990; Haugan et al., 1992, 1995), pSC101 (Xia et al., 1991; Goebel et al., 1991; Fang et al., 1993).

In the particular case in which the DNA molecule used possesses an origin of replication derived from the plasmid R6K, the initiator protein is a derivative of the II protein of this same plasmid. It is particularly advantageous to express a mutated form of this protein which is capable of increasing the number of initial copies appreciably. To do this, the gene incorporated into the host cell is preferably represented by all or part of the sequence represented in SEQ ID No. 2 or one of its derivatives and more preferably by the pir116 gene. The associated mutation corresponds to the replacement of a proline by a leucine. According to a particular embodiment of the invention, this pir116 gene is directly incorporated into the host cell genome.

Advantageously, one of the genes of the specific host cell, which is essential under the culture conditions chosen, contains a specific codon which is recognizable by the selected suppressor tRNA in the DNA molecule. According to a preferred mode of the invention, this is an amber TAG codon. In this particular case, the cell may grow, under culture conditions for which the product of the gene containing the TAG codon is essential, only if the plasmid allowing the expression of sup is present in the host cell. The culture conditions thus constitute the pressure for selection of the DNA molecule.

Preferably, the gene containing the amber codon is a gene involved in the biosynthesis of an amino acid, arginine. This gene, argE, codes for an N-acetylornithinase (Meinnel et al., 1992) and in this case contains a TAG codon corresponding to a point mutation Gln-53 (CAG)->TAG; the pressure for selection of the plasmid carrying the sup gene is then provided by culturing in minimal M9 medium (Maniatis et al., 1989). However, this could also be, for example, a gene for biosynthesis of a vitamin or a nucleic acid base, or alternatively a gene which allows a specific nitrogen or carbon source to be used or any other gene whose functionality is essential for cellular viability under the chosen culture conditions.

The host cell is preferably chosen from E. coli strains and is more preferably represented by the strain E. coli XAC-1.

According to a specific embodiment of the invention, the host cell used in the claimed process is a cell of the E. coli strain XAC-1, containing the pir116 gene in its genome and transformed by the plasmid pXL2774 or one of its derivatives.

According to an advantageous variant of the invention, the host cell used in the process claimed is a prokaryotic cell in which the endA1 gene or a homologous gene is inactivated. The endA gene codes for endonuclease I of E. coli. This periplasmic enzyme has a non-specific activity of cleaving double-stranded DNA (Lehman, I. R., G. G. Roussos and E. A. Pratt (1962) J. Biol. Chem. 237: 819-828; Wright M. (1971) J. Bacteriol. 107: 87-94). A study carried out on various strains of Escherichia coli (wild-type or endA) showed that the degradation of plasmid DNA incubated in extracts of these bacterial strains existed in the endA+ strains but not in the endA mutants. (Wnendt S. (1994) BioTechniques 17: 270-272). The quality of the plasmid DNA isolated from endA+ strains or from endA mutants was studied by the company Promega using their purification system (Shoenfeld, T., J. Mendez, D. Storts, E. Portman, B.†Patterson, J. Frederiksen and C. Smith. 1995. Effects of bacterial strains carrying the endA1 genotype on DNA quality isolated with Wizard plasmid purification systems. Promega notes 53). Their conclusion is as follows: the quality of the DNA prepared from endA mutants is, overall, better than that of DNA prepared in the endA+ strains tested.

The quality of the plasmid DNA preparations is thus affected by any contamination with this endonuclease (relatively long-term degradation of the DNA).

The deletion or mutation of the endA gene can be envisaged without difficulty insofar as the mutants no longer having this endonuclease activity behave on the whole like wild-type bacteria (Dürwald, H. and H. Hoffmann-Berling (1968) J. Mol. Biol. 34: 331-346).

The endA1 gene can be inactivated by mutation, total or partial deletion, disruption, etc. Inactivation of the endA gene of the E. coli strain chosen to produce the pCOR plasmids can be achieved more particularly by transferring, by means of the P1 bacteriophage, the ΔendA::Tc$^R$ deletion described by Cherepanov and Wackernagel (Cherepanov, P. P. and W. Wackernagel. 1995. Gene disruption in Escherichia coli: Tc$^R$ and Km$^R$ cassettes with the option of Flp-catalyzed excision of the antibiotic-resistance determinant. Gene 158:9-14) or by exchanging the wild-type allele present in the genome of the bacterium of interest with a mutated or deleted allele of endA, by homologous recombination. The use of this type of strain in the context of the present invention makes it possible advantageously to improve the quality of the DNA produced. The invention also relates to any recombinant cell containing a DNA molecule as defined above. This may be a cell of various origins, of eukaryotic, prokaryotic, etc. type.

According to another embodiment of the invention, the E. coli XAC-1 host cell used in the process claimed is designated TEX1, and comprises a traD gene, or a homologous gene thereof, inactivated to abolish F' transfer. The traD is at the 5' end of one of the tra operon and encodes a 81.7 kDa membrane protein that is directly involved in DNA transfer and DNA metabolism (Frost et al., Microbiology Reviews, 1994, 58: 162-210). traD mutants do not transfer DNA (Panicker et al., J. Bacteriol., 1985, 162:584-590). The episomal traD gene may be inactivated by mutation, total or partial deletion, or disruption using methods well known to those of skill in the art (See Example 9). One method of inactivating this gene is described in Example 1, and the resulting E. coli XAC-1 pir116 endA$^-$ traD$^-$ strain so obtained is designated TEX1 (Soubrier et al., Gene Therapy, 1999, 6: 1482-1488).

According to one embodiment of the invention, the host cell used in the claimed process is a cell of the E. coli strain XAC-1, containing the pir116 mutation combined with the pir42 mutation. The pir116 and pir42 mutations affect different domains of the pi protein. The pir116 mutation affects the copy number control region, whereas the pir42 mutation affects the putative leucine zipper motif, as displayed in FIG.

11. The nucleotide and amino acid sequences of the pir gene containing the pir116 and pir42 mutations are set forth in FIG. 12 and SEQ ID NOs: 21 and 22, respectively. The pir42 mutation comprises a C to T transition at position 124 from the methionine initiator codon, and thus results in substitution of the proline at position 42 by a leucine. The pir42 mutation was described by Miron et al. (Proc Natl Acad Sci USA, 1994. 91(14): p. 6438-42; EMBO J, 1992. 11(3): p. 1205-16), and was reported to increase the copy number of an "ori gamma R6K-$Km^R$-pir42" plasmid by 2.5 fold as compared to the same plasmid harboring the wild-type pir gene. However the pir42 mutation was never used or described in combination with the pir116 mutation and while other copy-up mutations such as cop21 in the pir gene combined with the pir116 do not exhibit an increase of the plasmid copy number, combination of the pir116 and pir42 mutations in a E. coli XAC-1 endA− traD− strain surprisingly showed a significant increase of the plasmid copy number. Applicants have thus shown unexpected results of this combination in terms of copy number of the plasmids produced in E. coli host strains comprising the mutated pir116 and pir42 gene as compared with strains harboring pir116 alone, or in a host cell comprising the pir116 mutation combined with another mutation of the pir gene, such as the mutation cop21 (Inuzuka et al., FEBS Lett, 1988. 228(1): p. 7-11). For example, E. coli TEX1pir42 (=XAC-1 endA− traD− pir116 pir42) exhibited a 2-5 fold increase in the number of plasmids, as compared to a pir116 strain, or strains comprising combined pir116 and cop21 mutations (See Example 11). In other embodiments, the pir gene comprises at least one mutation, which, for example, may occur in the copy number control region, in the leucine zipper-like motif, in the DNA binding region, or in one or more of these regions or another region of the protein pi coded by the pir gene.

The prokaryotic host cell according to the present invention also comprises one or more mutations in the same or a different domain of the protein pi, coded by the pir gene copy, such as the DNA binding domain, and/or the copy number control region and/or the leucine-zipper motif. The prokaryotic recombinant host cell may comprise the heterologous pir gene is in a plasmid or in the genome of the host cell.

Such mutations may be screened by using the fluorescence-based screening method according to one aspect of the present invention as described thereafter. As shown in the Example 13, host cells comprising at least one mutation in the pir gene, the mutation pir116 and a mutation in the DNA binding domain were screened using the fluorescence-based screening method according to the present invention. Host cells comprising mutations present in the DNA binding domain in addition to the pir116, i.e., as for example in the construct 100B, wherein the tyrosine (K) at position 292 is replaced by a methionine (M), in the construct 114C, wherein a glutamic acid (E) at position 130 is replaced by a valine (V), or in the construct 201C, wherein an aspartic acid (D) at position 117 is replaced by a glycine (G) (FIG. 26) are tested for their capacity to produce high copy number of plasmid using the fluorescence-based screening method.

According to another embodiment of the present invention, the host cell used in the process claimed is a prokaryotic host cell in which the recA gene or a homologous gene has been inactivated. Preferably, the host cell according to the present invention is E. coli strain XAC-1 comprising mutations pir116, pir42, endA−, traD−, recA−. Such a strain is designated TEX2pir42. recA may be inactivated by methods well known to those in the art. recA encodes a major recombination protein and mutations in this gene reduce the frequency of recombination-mediated alteration in plasmids and intramolecular recombination that could lead to the multimerization of plasmids. As described in Example 12, a deleted recA gene containing 3 translation stop codons (one in each frame) at its 5' end may be obtained by PCR. The resulting inactivated gene was then introduced by gene replacement into TEX1 genome (Example 12.1).

These cells are obtained by any technique known to those skilled in the art which allows the introduction of the said plasmid into a given cell. Such a technique may be, in particular, transformation, electroporation, conjugation, fusion of protoplasts or any other technique known to those skilled in the art.

Strain XAC-1pir116 was deposited under the terms of the Budapest Treaty with the Collection Nationale De Cultures de Micro-organismes (CNCM), Institut Pasteur, 28, rue Dr. Roux, 75724 Paris Cedex 15, France, on Oct. 1, 2003 under accession no. I-3108.

Strain TEX2pir42 was deposited under the terms of the Budapest Treaty with the Collection Nationale De Cultures de Micro-organismes (CNCM), Institut Pasteur, 28, rue Dr. Roux, 75724 Paris Cedex 15, France, on Oct. $10^{th}$, 2003, under accession no. I-3109.

The DNA molecules according to the invention may be used in any application of vaccination or of gene and cell therapy for transferring a gene to a given cell, tissue or organism, or for the production of recombinant proteins in vitro.

In particular, they may be used for direct in vivo administration or for the modification of cells in vitro or ex vivo, for the purpose of implanting them into a patient.

In this respect, another subject of the present invention relates to any pharmaceutical composition comprising at least one DNA molecule as defined above. This molecule may or may not be associated therein with a chemical and/or biochemical transfection vector. This may in particular involve cations (calcium phosphate, DEAE-dextran, etc.) or liposomes. The associated synthetic vectors may be cationic polymers or lipids. Examples of such vectors which may be mentioned are DOGS (Transfectam™) or DOTMA (lipofectin™).

The pharmaceutical compositions according to the invention may be formulated for the purpose of topical, oral, parenteral, intranasal, intravenous, intramuscular, subcutaneous, intraocular, or transdermal administrations. The claimed plasmid is preferably used in an injectable form or in application. It may be mixed with any vehicle which is pharmaceutically acceptable for an injectable formulation, in particular for a direct injection to the site to be treated. This may involve, in particular, sterile, isotonic solutions or dry compositions, in particular freeze-dried compositions, which, by addition, depending on the case, of sterilized water or of physiological saline, allow injectable solutions to be made up. This may in particular involve Tris or PBS buffers diluted in glucose or in sodium chloride. A direct injection into the affected region of the patient is advantageous since it allows the therapeutic effect to be concentrated at the level of the affected tissues. The doses used may be adapted as a function of various parameters, and in particular as a function of the gene, the vector, the mode of administration used, the pathology concerned or the desired duration of the treatment.

The DNA molecules of the invention may contain one or more genes of interest, that is to say one or more nucleic acids (synthetic or semi-synthetic DNA, gDNA, cDNA, etc.)

whose transcription and, possibly, whose translation in the target cell generate products of therapeutic, vaccinal, agronomic or veterinary interest.

Among the genes of therapeutic interest which may be mentioned more particularly are genes coding for enzymes, blood derivatives, hormones and lymphokines: interleukins, interferons, TNF, etc. (FR 92/03120), growth factors, neurotransmitters or their precursors or synthetic enzymes, and trophic factors (BDNF, CNTF, NGF, IGF, GMF, aFGF, bFGF, NT3, NT5, VEGF-B, VEGF-C etc.; apolipoproteins: ApoAl, ApoAIV, ApoE, etc. (FR 93/05125), dystrophin or a minidystrophin (FR 91/11947), tumour-suppressing genes: p53, Rb, Rap1A, DCC, k-rev, etc. (FR 93/04745), genes coding for factors involved in coagulation: factors VII, VII, IX, etc., suicide genes: thymidine kinase, cytosine deaminase, etc.; or alternatively all or part of a natural or artificial immunoglobulin (Fab, ScFv, etc.), an RNA ligand (WO 91/19813), etc. The therapeutic gene may also be an antisense sequence or gene, whose expression in the target cell makes it possible to control the expression of genes or the transcription of cellular mRNAs. Such sequences may, for example, be transcribed, in the target cell, into RNAs which are complementary to cellular mRNAs and thus block their translation into protein, according to the technique described in patent EP 140,308. A insert of interest that may be carried by the pCOR of the invention is a RNAi, whose is capable of interfering with the translation of a target gene (Wilson et al., Curr Opin Mol Ther. 2003 August; 5(4):389-96) and thereby regulating the expression of such gene.

The gene of interest may also be a vaccinating gene, that is to say a gene coding for an antigenic peptide, capable of generating an immune response in man or animals, for the purpose of producing vaccines. These antigenic peptides may in particular be specific antigenic peptides of Epstein-Barr virus, HIV virus, hepatitis B virus (EP 185,573), or pseudorabies virus, or alternatively specific antigenic peptides of tumours (EP 259,212).

Generally, in the DNA molecules of the invention, the gene of therapeutic, vaccinal, agronomic or veterinary interest also contains a promoter region for functional transcription in the target organism or cell, as well as a region located at the 3' end which specifies a transcription termination signal and a polyadenylation site. As regards the promoter region, it may be a promoter region naturally responsible for expression of the gene under consideration when this region is capable of functioning in the cell or the organism concerned. The promoter regions may also be regions of different origin (responsible for the expression of other proteins) or even of synthetic origin. In particular, they may be promoter sequences from eukaryotic or viral genes. For example, they may be promoter sequences obtained from the genome of the target cell. Among the eukaryotic promoters which may be used are any promoters or derived sequence which stimulates or suppresses the transcription of a gene in a specific or non-specific, inducible or non-inducible, strong or weak manner. The eukaryotic promoters may in particular be ubiquitous promoters (promoters of the genes for HPRT, PGK, α-actin, tubulin, etc.), intermediate filament promoters (promoters of the genes for GFAP, desmin, vimentin, neurofilaments, keratin, etc.), therapeutic gene promoters (for example the promoters of the genes for MDR, CFTR, factor VIII, ApoAI, etc.) tissue-specific promoters (promoters of the genes for pyruvate kinase, villin, intestinal fatty acid-binding protein, α-actin of smooth muscle, etc.) or alternatively promoters which respond to a stimulus (steroid hormone receptor, retinoic acid receptor, etc.). Similarly, they may be promoter sequences obtained from the genome of a virus, such as, for example, the promoters of the adenovirus E1A and MLP genes, the CMV early promoter or alternatively the LTR promoter of RSV, etc. In addition, these promoter regions may e modified by addition of activating or regulatory sequences or sequences which allow tissue-specific expression or expression which is predominantly tissue-specific.

Moreover, the gene of interest may also contain a signal sequence which directs the synthesized product into the secretory pathways of the target cell. This signal sequence may be the natural signal sequence of the synthesized product, but it may also be any other functional signal sequence or an artificial signal sequence. Preferred signal sequence used according to the present invention is the secretion signal peptide of human interferon as described Taniguchi et al. (Gene, 1980, 233 (4763):541-5)

Depending on the gene of interest, the DNA molecules of the invention may be used for the treatment or prevention of several pathologies, including genetic diseases (dystrophy, cystic fibrosis, etc.), neurodegenerative diseases (Alzheimer's disease, Parkinson's disease, ALS, etc.), cancers, pathologies associated with coagulation disorders or with dyslipoproteinaemias, pathologies associated with viral infections (hepatitis, AIDS, etc.), or in the agronomic and veterinary fields, etc.

According a preferred embodiment, the DNA molecules of the present invention are used for treating critical limb ischemia pathologies such as for example peripheral arterial occlusive disease and intermittent claudication.

Moreover, the present invention also relates to the use of conditional replication DNA molecules for the production of recombinant proteins. Bacteria can be used to produce proteins of various origins, eukaryotic or prokaryotic. Among the bacteria, $E. coli$ constitutes the organism of choice for expressing heterologous genes on account of its ease of manipulation, the large number of expression systems available and the large amounts of proteins which can be obtained. It is understood that the system of the invention can be used in other organisms, the tropism being determined by the nature of the origin of replication, as indicated above. For this use, the nucleic acid sequence of interest comprises a coding region under the control of expression signals that are appropriate for the host chosen, in particular a prokaryotic host. These may be, for example, Plac, Ptrp, PT7, Ptrc, Ptac, PL, $P_{BAD}$ or PR promoters, the Shine-Dalgarno sequence, etc. (this set constitutes the expression cassette). The nucleic acid sequence of interest can be any sequence coding for a protein which is of value in the fields of pharmacy, agri-foods, chemistry or agrochemistry. This may be a structural gene, a complementary DNA sequence, a synthetic or semi-synthetic sequence, etc.

The expression cassette can be introduced onto the conditional replication vector which is the subject of the invention, thus constituting a conditional replication vector which allows the expression of proteins of interest in $E. coli$. This vector has several advantages: no use of antibiotic to select it in the bacterium (reduced cost, no need for a study regarding the presence of antibiotic or of potentially toxic derived products in the finished product), virtually no probability of dissemination of the plasmid in nature (conditional origin of replication), possible fermentation in entirely defined medium. The examples given show the advantageous properties of these conditional vectors for the production of recombinant proteins.

As described above, the DNA molecule according to the present invention comprises an origin of replication ORIγ derived from R6K wherein the pir gene is removed and is introduced into the genome of a specific host cell that is used for the production of the DNA molecules at large scale. There is always a need to produce increasing quantities of plasmid for clinical trials and/or for use in DNA-based gene therapy. Production host cells have been engineered to carry the pir gene containing at least one mutation, such as the mutation pir116 and/or pir42. Use of such mutated host strain results in an increase of the plasmids copy number and thus significantly raises the yield of production. Also, conformation of the plasmids so produced is very satisfying.

According to a particular aspect, a novel fluorescence-based method of screening for copy-up mutant is provided. This fluorescence-based screening method is far superior to the classical method of screening based on the level of resistance to antibiotic in the bacteria, which may not be used when the basal copy number of plasmid is already very high such as the one obtained using the mutant pir116, e.g., around 400 copies of plasmid per cell. The fluorescence-based method of screening according to the present invention preferably uses the cobA gene as red fluorescence reporter gene of copy-up number. The cobA gene which is a gene from *Pseudomonas denitrificans* (Crouzet et al., J. Bacteriol. 1999, 172: 5968-79) encodes uro III methyltransferase, an enzyme of the vitamin B12 pathway, which adds two methyl groups to urogen III molecule. Wildt et al. (Nature Biotechnology, vol. 17, 1999, pp 1175) has described the use of cobA as a fluorescent transcriptional reporter gene for *E. coli*, yeast and mammalian cells. For example, such fluorescent reporter gene was used for the selection of recombinant plasmids containing *E. coli* strains which accumulate fluorescent porhyrinoid compounds due to overexpression of the cobA gene encoding the uroIII methyltransferase. When illuminated with UV light, the cells fluoresced with a bright red color (Biotechniques, 1995, vol 19, no. 7, p. 760).

The Applicant has surprisingly found a close correlation between the copy number of plasmid carrying the cobA gene and the level of fluorescence from pink to red. The fluorescence-based method of screening of copy-up mutants according to the present invention is thus useful for screening various mutants which can then be evaluated in the genome of the production host cell, such as *E. coli*, or mutants of any genes such as in the pir gene, which are inserted in the genome of the production host cell or carried in a plasmid.

In addition to the correlation with the copy number of plasmids, the fluorescence-based method of screening of the present invention is easily and rapidly conducted as it is only requires plating and culturing the transformed host cells overnight and exposing to UV lights, to reveal intensity of the fluorescence produced, thereby deducing directly the number of copy of plasmids in the host cell.

Thus, the present invention provides for a method for detecting a plasmid copy-up mutation comprising:
  (a) introducing at least one mutation into a target sequence;
  (b) transforming the mutated target sequence into a host cell comprising a plasmid, wherein the plasmid comprises a nucleotide sequence encoding uroIII methyltransferase and the copy number of the plasmid is effected by the target sequence;
  (c) growing the host cell under conditions wherein the nucleotide sequence is expressed to produce a culture of host cells;
  (d) exposing the culture of host cells to UV light; and
  (e) detecting fluorescence produced by the culture of host cells.

According to the present invention, the method further comprises comparing the fluorescence detected in (e) with fluorescence produced by a culture of host cells comprising an non-mutated target sequence.

Preferably, the uroIII methyltransferase gene is coded by the cobA gene from *Pseudomonas denitrificans*.

The mutation may be present in a plasmid comprising a heterologous pir gene comprising at least one mutation. The plasmid may comprise at least one mutation in the pir other regions such as in the copy control region and/or in the DNA binding domain, and/or in the leucine-zipper motif and/or in another region of the pir gene. Also, the plasmid may comprise at least one mutation in the heterologous pir gene copy number control region and the leucine zipper-like motif. The plasmid may further comprise a mutation in the pir gene DNA binding region. Furthermore, the plasmid may comprise one or more mutations in the same or a different region of the pir gene coding for the copy control region and/or the DNA binding region, and/or the leucine zipper-like motif, or other region of the protein π.

Within limitation, the prokaryotic recombinant host cell according to the present invention comprises the pir116 mutation and a second mutation in the DNA binding region such as pir292, pir130, or pir117 (FIG. 26).

Such mutated production host strain may be advantageously produced using an universal plasmid tool such as the minicircle. The minicircle technology is described inter alia in U.S. Pat. Nos. 6,143,530 and 6,492,164 of the Applicant or in PCT application WO 96/26270.

Minicircles are recombinant DNA molecules that do not contain any origin of replication, and thus represent excellent suicide vector for gene replacement of the genome of any microorganisms. In particular, the gene or genes of interest are flanked by the two sequences permitting site-specific recombination, positioned in the direct orientation in the minicircle. The position in the direct orientation indicates that the two sequences follow the same 5'-3' polarity in the recombinant DNA minicircle. The minicircle genetic constructions are generally circular double-stranded DNA molecules devoid of origin of replication, but may also be in linear form and contain the gene or genes of interest flanked by the two sequences permitting site-specific recombination, positioned in the direct orientation. According to this particular embodiment of the invention, the minicircle may be used to transform any competent microorganisms for the purpose of the gene replacement within the genome thereof (FIG. 31).

The minicircle for gene replacement is generated from a parent plasmid comprising at least:
  a) an origin of replication and, a selection marker gene,
  b) two sequences permitting site-specific recombination, positioned in the direct orientation, and,
  c) placed between said sequences b), one or more genes of interest.

The specific recombination system present in the genetic constructions can be of different origins. In particular, the specific sequences and the recombinases used can belong to different structural classes, and in particular to the integrase family of bacteriophage λ or to the resolvase family of the transposon Tn3. Among recombinases belonging to the integrase family of bacteriophage λ, there may be mentioned, in particular, the integrase of the phages lambda (Landy et al., Science 197: 1147, 1977), P22 and Φ80 (Leong et al., J. Biol. Chem. 260: 4468, 1985), HP1 of *Haemophilus influenza* (Hauser et al., J. Biol. Chem. 267 6859, 1992), the Cre integrase of phage P1, the integrase of the plasmid pSAM2 (EP 350,341) or alternatively the FLP recombinase of the 2µ plasmid. The minicircles are thus prepared by recombination by means of a site-specific system of the integrase family of bacteriophage λ, the DNA molecules according to the invention generally comprise, in addition, a sequence resulting from the recombination between two att attachment sequences of the corresponding bacteriophage or plasmid.

Among recombinases belonging to the family of the transposon Tn3, there may be mentioned, in particular, the resolvase of the transposon Tn3 or of the transposons Tn21 and Tn522 (Stark et al., Trends Genet, 8, 432-439, 1992); the Gin invertase of bacteriophage λ, or, alternatively, the resolvase of plasmids, such as that of the par fragment of RP4 (Albert et al., Mol. Microbiol. 12: 131, 1994). When the minicircles are prepared by recombination by means of a site-specific system of the family of the transposon Tn3, they generally comprise, in addition to the gene of interest that is aimed to be inserted in a microorganism genome, a sequence resulting from the recombination between two recognition sequences of the resolvase of the transposon in question. Sequences permitting site-specific recombination may also be derived from the loxP region of phage P1, which is composed essentially of two repeat sequences capable of recombining specifically with one another in the presence of a protein, designated Cre (Sternberg et al., J. Mol. Biol. 150: 467, 1971). The plasmid used to produce the minicircle thus comprises (a) a bacterial origin of replication and, a selection marker gene; (b) the repeat sequences of bacteriophage P1 (loxP region); and (c), placed between said sequences (b), one or more genes of interest that one's wish to insert in a microorganism genome.

Minicircles may comprise sequences permitting site-specific recombination are derived from a bacteriophage, such as attachment sequences (attP and attB sequences) of a bacteriophage or sequences derived from such attachment sequences. These sequences are capable of recombining specifically with one another in the presence of a recombinase referred to as an integrase with or without an excisionase. The term "sequences derived from such attachment sequences" includes the sequences obtained by modification(s) of the attachment sequences of the bacteriophages that retain the capacity to recombine specifically in the presence of the appropriate recombinase. Thus, such sequences can be reduced fragments of these sequences or, alternatively, fragments extended by the addition of other sequences (restriction sites, and the like). They can also be variants obtained by mutation(s), in particular by point mutation(s). The terms attP and attB sequences of a bacteriophage or of a plasmid denote, according to the invention, the sequences of the recombination system specific to said bacteriophage or plasmid, that is to say the attP sequence present in said phage or plasmid and the corresponding chromosomal attB sequence. Attachment sequences are well known in the art, and include inter alia the attachment sequences of the phages λ, P22, Φ80, P1, and HP1 of Haemophilus influenzae or, alternatively, of plasmid pSAM2 or the 2µ plasmid.

The minicircles are easly produced from the parent plasmid described above. The method for the production of the minicircle consists in bringing into contact culture of cells that are transformed with the parent plasmid with the integrase with or without the excisionase, so as to induce the site-specific recombination. The culture and the integrase with or without the excisionase are brought into contact either by transfection or infection with a plasmid or a phage containing the gene for said integrase and when applicable the gene for the excisionase. Alternatively, for example, the expression of genes coding for said integrase and when applicable the excisionase, present in the host cell, are induced. As mentioned below, these genes may be present in the host cell in integrated form in the genome, on a replicative plasmid, or, alternatively, on the plasmid of the invention, in the non-therapeutic portion.

To permit the production of the minicircles according to the invention by site-specific recombination in vivo, the integrase with/without the excisionase used are introduced into, or induced in, cells or the culture medium at a particular instant. For this purpose, different methods may be used. According to a first method, a host cell is used containing, for example, the recombinase gene, i.e., the integrase gene with or without the excisionase gene, in a form permitting its regulated expression. The integrase gene with or without the excisionase gene may, for example, be introduced under the control of a promoter, or of a system of inducible promoters, or, alternatively, in a temperature-sensitive system.

In particular, the integrase gene may be present in a temperature-sensitive phage, latent during the growth phase, and induced at a suitable temperature (for example, lysogenic phage λ Xis⁻ cl857).

Alternatively, the gene may be under the control of a regulated promoter, for example, the placUV5 promoter, the host cell is designated E. coli G6191.

Preferably, the integrase with or without the excisionase gene may be under the control of a regulated promoter, for example the $P_{BAD}$ promoter of the araBAD (arabinose) operon, which is regulated by arabinose (Guzman et al., J. Bacteriol, 1995, 4121-4130; U.S. Pat. No. 5,028,530). Particularly, use of $P_{BAD}$ promoter allows sufficient expression of excisionase and integrase in presence of arabinose, as the inducing agent, and thus more than 90% of recombination of the plasmids which are present in high copies number in the bacteria, whereas in absence of arabinose, the promoter is tightly inhibited. The cassette for expression of the integrase with/without excisionase may be carried by a plasmid, a phage, or even by the plasmid of the invention in the non-therapeutic region. It may be integrated in the genome of the host cell or maintained in replicative form. Such host cells are in particular E. coli G6264 and E. coli G6289. According to another method, the cassette for expression of the gene(s) is carried by a plasmid or a phage used to transfect or infect the cell culture after the growth phase. In this case, it is not necessary for the gene to be in a form permitting its regulated expression. In particular, any constitutive promoter may be used. The DNA may also be brought into contact with the integrase and when applicable the excisionase in vitro, on a plasmid preparation, by direct incubation with the protein.

The minicircle so produced thus comprises an expression cassette containing one or more genes of interest to be inserted in the targeted microorganism, lacks an origin of replication and comprises a sequence attR resulting from site-specific recombination between an attB and an attP sequence, or a sequence attL resulting from site-specific recombination between an attB and an attP sequence. The minicircle may thus be used as universal suicide vector for gene replacement in any microorganisms. In effect, the minicircle carrying a gene for replacement flanked by homologous sequences and a antibiotic resistance gene will easily integrate in a targeted site of the genome of any microorganism by homologous recombination as represented in FIG. 31. A second event of excision which may be triggered by a second selection pressure may then efficiently select the microorganisms only carrying the new inserted gene within their genome.

The present invention thus also relates to a method of gene engineering of a microorganism. This novel method may used to engineer any microorganism regardless of their origin. In effect, the minicircle does not contain any origin of replication, and thus can be used universally for gene replacement in any types of microorganisms. This method represents an advantageous alternative to the use of the bacteriophage M13 for gene replacement by double homologous recombination in a micro-organism.

According to a particular embodiment of the present invention, the minicircle comprises a first selectable marker such as an antibiotic resistance gene, allowing selecting for the first recombination event. Preferred second selectable marker is the gene III or the functional deleted gene III'. The gene III or its functional variant is capable of conferring sensibility to deoxycholate as described in Boecke et al. (Mol. Gen. Genet., 186, 185-92, 1982) and thus allows for counter-selecting the second event of recombination (FIG. 31). The method thus consists in introducing the minicircle into the microorganism by any transformation method well known in the art, and preferably by electroporation, selecting the event of integration of the minicircle in a culture supplemented with an antibiotic or under another pression of selection, and selecting a second event of excision by treating with deoxycholate or another appropriate pression of selection.

The present invention will be described more fully with the aid of the examples which follow, which should be considered as non-limiting illustrations.

BRIEF DESCRIPTION OF THE DRAWINGS

FIG. 12: Nucleotide and amino acid sequences of the pir gene comprising the pir116 and pir42 mutations.

FIG. 14: Schematic representation of the PCR products obtained when amplifying the region uidA::pir116+/− pir42.

FIG. 18: Representation of the cloning strategy for the construction of the recA− suicide vector.

FIG. 22: Fluorescence-based assay showing that fluorescence increases with plasmid copy number.

FIG. 23: Diagram of plasmids screened in the fluorescence-based assay.

FIG. 30: Construction of a minicircle vector used to generate pir116* mutant E. coli strains.

FIG. 31: Diagram of gene replacement by homologous recombination using a minicircle vector.

I—MATERIALS AND METHODS

A) Materials

1) Culture Media

Figure 1:
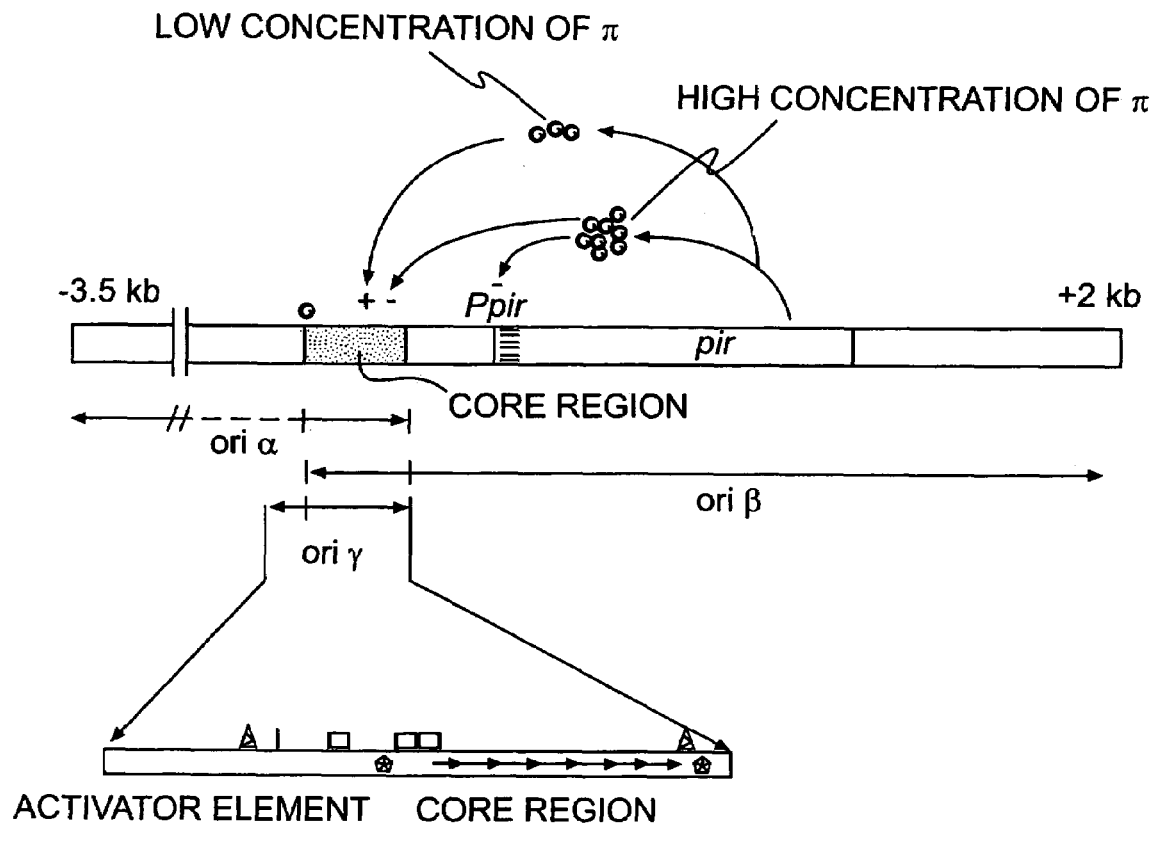
FIG. 1: Functional organization of the region of R6K involved in replication.
Figure 2:
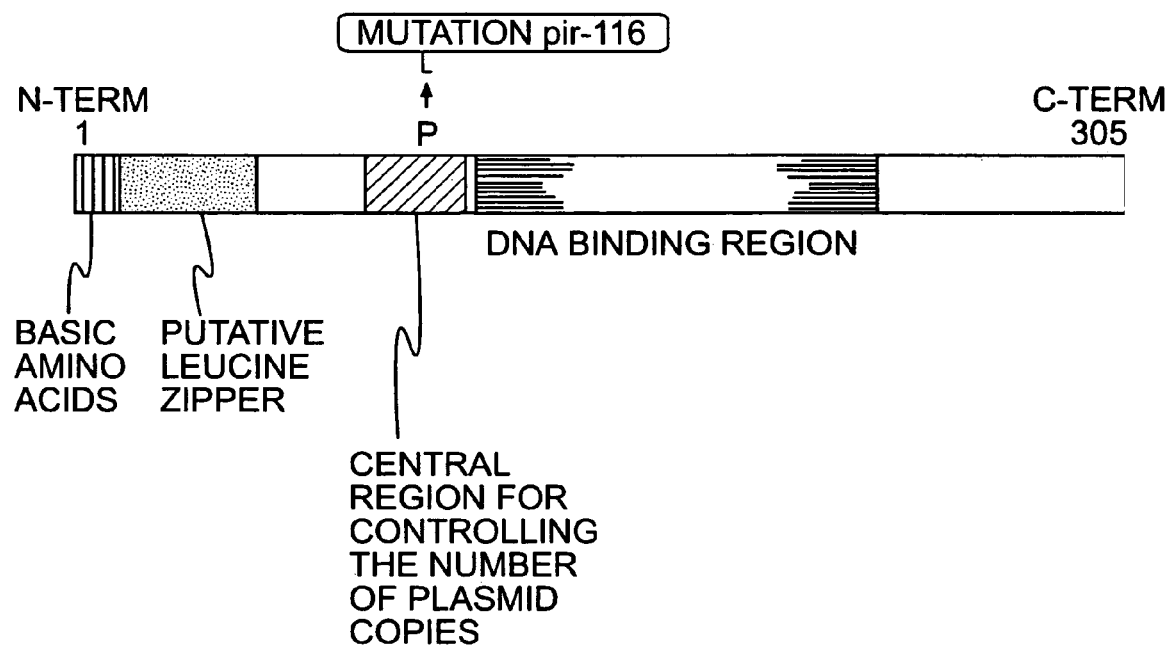
FIG. 2: Organization of the functional domains of the Π protein of the plasmid R6k.

Complete LB, 2XTY and SOC media and minimal M9 medium (Maniatis et al., 1989) were used. Agar media were obtained by addition of 15 g of Difco agar. Furthermore, if necessary, these media were supplemented with antibiotics (ampicillin or kanamycin) at respective concentrations of 100 mg/l and 50 mg/l. The chromogenic substrates X-Gal and X-Gluc were used at a concentration of 40 mg/l.

2) E. coli Strains, Plasmids and Bacteriophages

The E. coli strains, plasmids and bacteriophages used are respectively identified in the examples below.

B) Methods

1) Manipulation of the DNA

The isolation of bacterial DNA (plasmid and genomic) and phage DNA (replicative form of M13), digestion with restriction endonucleases, ligation of the DNA fragments, agarose gel electrophoresis (in TBE buffer) and other standard techniques were carried out according to the manufacturers' recommendations, for the use of enzymes, or in accordance with the procedures described in "Molecular Cloning: a Laboratory Manual" (Maniatis et al., 1989).

The DNA size markers used during the electrophoreses are as follows: 1 kb ladder (BRL) for the linear fragments and the supercoiled DNA marker (Stratagene) for the undigested plasmids.

Sequencing was carried out according to the Sanger technique (Sanger et al., 1977) adapted to the automated method using fluorescent dideoxynucleotides and Taq DNA polymerase (PRISM Ready Reaction DyeDideoxy Terminator Cycle Sequencing Kit, Applied Biosystems).

The oligodeoxynucleotides used (designated by "seq+ no.", see below) were synthesized on the "Applied Biosystems 394 DNA/RNA Synthesizer" by the phosphoramidite method, using α-cyanoethyl protecting groups (Sinha et al., 1984). After synthesis, the protecting groups are removed by treatment with ammonia. Two precipitations with butanol allow the oligonucleotide to be purified and concentrated (Sawadogo et al., 1991).

Sequences of the Oligonucleotides Used for the PCR Amplification:

```
SEQ ID No. 3    5'-GACCAGTATTATTATCTTAATGAG-3'
SEQ ID No. 4    5'-GTATTTAATGAAACCGTACCTCCC-3'
SEQ ID No. 5    5'-CTCTTTTAATTGTCGATAAGCAAG-3'
SEQ ID No. 6    5'-GCGACGTCACCGAGGCTGTAGCCG-3'
```

The PCR reactions (Saïki et al., 1985) were performed under the following conditions, in a total volume of 100 µl. The reaction mixture comprises 150 ng of genomic DNA from the strain to be studied, 1 µg of each of the two oligonucleotide primers (24-mer), 10 µl of 10×PCR buffer, the composition of which is as follows "500 mM KCl, 0.1% gelatin, 20 mM $MgCl_2$, 100 mM Tris-HCl pH 7.5", and 2.5 units of Taq DNA polymerase (Amplitaq Perkin-Elmer). The PCR conditions, on the Perkin-Elmer Cetus DNA Thermal Cycler machine are as follows: 2 min at 91° C., 30 successive cycles of denaturation (1 min at 91° C.), hybridization (2 min at 42° C.) and elongation (3 min at 72° C.), and finally 5 min at 72° C. The products thus obtained, which are or are not digested with a restriction enzyme, are analysed by agarose gel electrophoresis.

Analysis of the various plasmid species by DNA topoisomerases was performed according to the following procedure: the enzymes, purified in the laboratory, are incubated for 1 hour at 37° C. The reaction mixtures (total volume: 40 µl) have the following composition: 150 ng of plasmid, 300 ng of DNA topoisomerase I or 150 ng of *E. coli* DNA gyrase, or 160 ng of *S. aureus* DNA topoisomerase IV and 20 µl of buffer specific for each enzyme. The composition of these buffers is indicated below:

for DNA topoisomerase I:
50 mM Tris-HCl pH 7.7, 40 mM KCl, 1 mM DTT, 100 µg/ml BSA, 3 mM $MgCl_2$, 1 mM EDTA;

for DNA topoisomerase IV:
60 mM Tris-HCl pH 7.7, 6 mM $MgCl_2$, 10 mM DTT, 100 µg/ml BSA, 1.5 mM ATP, 350 mM potassium glutamate;

for DNA gyrase:
50 mM Tris-HCl pH 7.7, 5 mM $MgCl_2$, 1.5 mM ATP, 5 mM DTT, 100 µg/ml BSA, 20 mM KCl.

2) Transformation of *E. coli*

This was performed routinely according to the TSB (Transformation and Storage Buffer) method described by Chung and Miller (1988). For a strain such as TG1 (Gibson et al., 1984), the transformation efficiency obtained is about $10^5$-$10^6$ transformants per µg of pUC4K (Vieira and Messing; 1982). When a higher transformation efficiency was necessary, the bacteria were transformed by electroporation according to the procedure recommended by the electroporator manufacturer (Biorad). This method makes it possible to achieve efficiencies of from $10^8$ to $10^{10}$ transformants per µg of pUC4K.

3) Cellular Transfection Mediated by a Cationic Lipofectant

The cells used are NIH 3T3 mouse fibroblasts seeded the day before into 24-well plates, at a density of 50,000 cells per well. The culture medium used is DMEM medium, containing 4.5 g/l of glucose and supplemented with 10% fetal calf serum and 1% of solutions of 200 mM glutamine and antibiotics ($5.10^3$ µ/ml streptomycin, $5.10^3$ µg/ml penicillin) (Gibco). The plasmid DNA (1 µg in 25 µl of 9% NaCl) is mixed, on a volume-for-volume basis, with a suspension of lipofectant. Four "lipofectant charges/DNA charges" ratios are tested: 0, 3, 6 and 9. These ratios are calculated by considering that 1 µg of plasmid DNA carries 3.1 nmol of negative charges and that the lipofectant contains 3 positive charges per molecule. After a contact time of 10 minutes to allow formation of the DNA/lipid complex, 50 µl of DNA-lipofectant mixture are introduced onto the cells in serum-free culture medium (500 µl). The cells were prerinsed twice with this same medium. Inhibition of transfection by the serum is thus avoided. After incubation (2 hours at 37° C. in the $CO_2$ incubator), 10% fetal calf serum is added to the medium. The cells are then reincubated for 24 hours.

4) Measurement of the Luciferase Activity of Eukaryotic Cells

This is carried out 24 hours after the transfection. Luciferase catalyses the oxidation of luciferin in the presence of ATP, $Mg^{2+}$ and $O_2$, with concomitant production of a photon. The total amount of light emitted, measured by a luminometer, is proportional to the luciferase activity of the sample. The reagents used are supplied by Promega (luciferase assay system) and used according to the recommended procedure. After lysis of the cells, the insoluble fraction from each extract is eliminated by centrifugation. The assay is carried out on 5 µl of supernatant, which may or may not be diluted in the cell lysis buffer.

5) Measurement of the Protein Concentration in the Cell Extracts

This is carried out according to the BCA method (Pierce) using bicinchoninic acid (Wiechelman et al., 1988). The standard BSA range is prepared in the lysis buffer (cf. III-B-4). The samples to be assayed and those of the range are pretreated, on a volume-for-volume basis, with 0.1 M iodoacetamide/0.1 M Tris buffer, pH 8.2, for 1 hour at 37° C. This treatment makes it possible to prevent interference, during the assay, of the reducing agent (DTT) present in the lysis buffer. The assay result is read at 562 nm.

EXAMPLE 1

Construction of XAC-1 pir and pir116 Host Strains by Homologous Recombination

The strain used was the *E. coli* strain XAC-1 (Normanly et al., 1980). The argE gene of this strain advantageously includes a mutation of glutamine-53 (CAG) into the amber codon (TAG) (Meinnel et al., 1992). The argE gene belongs to the argECBH divergent operon and codes for an arginine biosynthesis enzyme, N-acetylornithinase. XAC-1 cannot therefore synthesize arginine and, consequently, grow in minimal medium. This auxotrophy will be relieved if the strain harbors a plasmid which allows the expression of a suppressor tRNA. It will thus be possible, by culturing in minimal medium, to select bacteria that carry such a plasmid. In order to allow the replication therein of plasmids derived from R6K, it was necessary to introduce, by homologous recombination, the pir gene into the genome of XAC-1. The pir gene (wild-type or mutated) is introduced at the uidA locus by exchange between the wild-type uidA gene and a copy interrupted by the pir (or pir116) gene. The uidA gene codes for β-glucuronidase, the enzyme for hydrolysis of β-glucuronides. This gene may be inactivated without any problem since it is not essential for growth in standard synthetic media, in which β-glucuronides are not used. Furthermore, the β-glucuronidase activity can be monitored by means of a chromogenic substrate, X-Gluc, whose hydrolysis releases a blue pigment.

1) Construction of a Suicide Vector Carrying the Cassette "$Km^R$-uidA::pir (or pir116)

We used a strategy involving a single bacterial host and minimizing the modifications to the genome of the strain of interest. The phage M13mp10 (Messing et Vieira; 1982) was used as a suicide vector (Blum et al., 1989). An amber mutation in the gene II, which is essential for replication, reduces the host spectrum of this M13 to the strains, such as TG1 (supE), which produce an amber suppressor tRNA; it will therefore not be able to replicate in E. coli sup+ strains, such as XAC-1.

The 3.8 kb BamHI cassettes, containing the kanamycin-resistance gene of Tn5 and _uidA::pir or pir116, were respectively purified from M13wm34 and 33 (Metcalf et al., 1994). They were cloned into M13 mp10 linearized with BamHI. The recombinant clones were selected by plating on LB agar medium supplemented with kanamycin, after electroporating the ligation mixtures into TG1. The conformity of the clones obtained was shown by analysing the restriction profile and by sequencing the region corresponding to the pir116 mutation.

Figure 3:
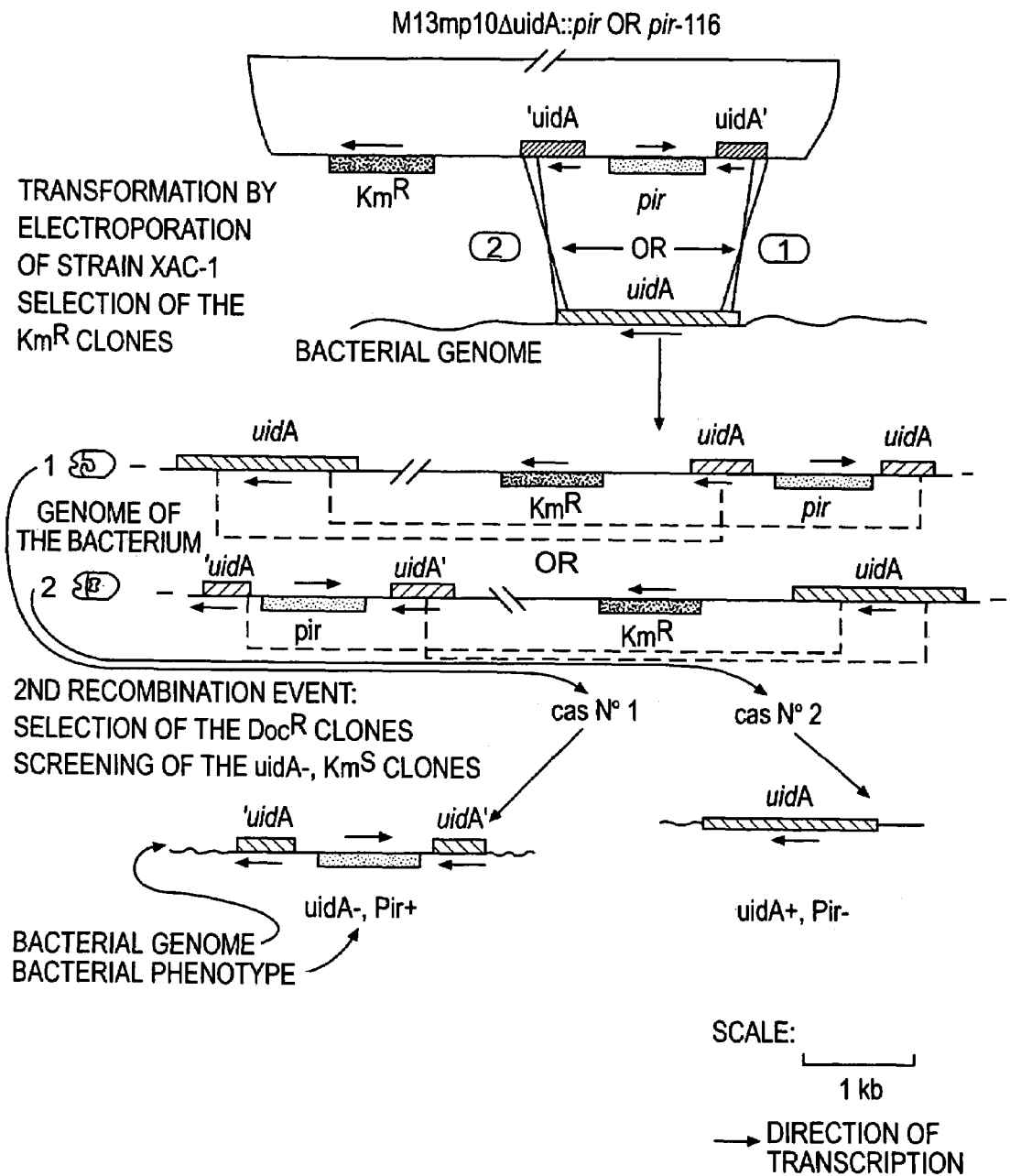
FIG. 3: Representation of the protocol for introducing the pir gene into the genome of E. coli XAC1.

2) Introduction of the pir or pir116 Genes Into the Genome of E. coli XAC-1 by Homologous Recombination The strategy adopted and the various events involved are presented in FIG. 3.

a) First Recombination Event

The XAC-1 strain was transformed by electroporation with 10, 100 or 2000 ng of each RF (mp10-_uidA::pir or pir116). One-third of each expression mixture was plated out on LB plates containing kanamycin and incubated overnight at 37° C. The mp10-_uidA::pir or pir116 phages cannot replicate in the strain XAC-1 (sup+). The kanamycin resistance ("$KM^R$") marker can therefore only be maintained by integration into the genome of the bacterium via a homologous recombination with the wild-type copy of the gene uidA. The results of the electroporations of XAC-1 are presented in Table 1. The transformation efficiency obtained was $4.10^9$ transformants per μg of pUC4K.

TABLE 1

| CONSTRUCT | Number of colonies obtained with the amounts of DNA transformed | | |
|---|---|---|---|
|  | 10 ng | 100 ng | 2000 ng |
| M13mp10-_uidA::pir | 1 | 41 | 146 |
| M13mp10-_uidA::pir116 | 0 | 16 | 124 |

Under the test conditions, the number of integrants increased in a non-linear manner with the amount of DNA. Given the transformation efficiency and the size of the RFs (11.7 kbp), it was possible to have an approximate idea of the level of recombination. By considering the point at 100 ng, a recombination frequency of about $10^{-6}$ was obtained.

b) Second Recombination Event

The second recombination event will then be selected by the resistance of the strains to deoxycholate ("$Doc^R$").

To do this, five integrants of each construct were cultured in 2TY medium supplemented with 0.2% sodium deoxycholate. Two distinct populations appeared. Certain clones gave quite visible cloudiness after about 8 hours at 37° C. (two clones for the pir construction and three for the pir116 construction). The other clones gave a dense culture only after one night at 37° C. They were virtually all sensitive to kanamycin ("$Km^S$"), as expected. For each of the electroporants studied, 50 $Km^S$ descendants were streaked onto LB medium supplemented with X-Gluc. After 48 hours at 37° C., the UidA$^+$ clones were pale blue whereas those which had undergone an allele replacement (case No. 1, FIG. 3) remained white on this medium (UidA$^-$). Table 2 summarizes the phenotypic analysis of the double recombinants obtained. From 18 to 30% of the double recombinants underwent an allele replacement.

TABLE 2

| Strain | Number of $Km^S$ among the $Doc^R$ | Percentage of UidA$^-$ among the $Km^S$ |
|---|---|---|
| XAC-1 pir-2 | 50/50 | 18 |
| XAC-1 pir-3 | 50/50 | 24 |
| XAC-1 pir-4 | 50/50 | 34 |
| XAC-1 pir116-1 | 50/50 | 32 |
| XAC pir116-4 | 35/50 | 30 |

3) Checking the Pir+ character nature of the strains obtained by recombination

To ensure the Pir+ character of the strains obtained by double recombination, we transformed three clones of each construct with pBW30 (Metcalf et al., 1994). The fact that transformants were obtained for all the test strains made it possible to show the functionality of the pir and pir116 genes, which were integrated into the genome of XAC-1. Under the same conditions, no transformant was obtained with the parental strain XAC-1. We continued to study two XAC-1pir clones (B and C) and two XAC-1pir116 clones (E and D).

4) Checking, by PCR Amplification, of the Strains Obtained by Recombination

To confirm the allele replacement, we checked the genomic regions on either side of the uidA locus by PCR amplification. Each pair of oligonucleotides consisted of an oligonucleotide corresponding to an internal region of pir and a second oligonucleotide corresponding to a region, close to chromosomal uidA, but not within the fragment which served for the recombination. The sequence of the latter oligonucleotide was determined by means of the ECOUIDAA sequence from Genbank (access number: M14641). We were thus able to verify the exact location of the pir gene in the bacterial genome. The nature of the amplified fragments, whose size is in accordance with that which might be expected, was confirmed by digestion with MluI.

EXAMPLE 2

Construction of Plasmid Vectors Derived from R6K Carrying the Selection Marker sup Phe Vectors were constructed containing ori γ from R6K and the kanamycin-resistance gene (pXL2666). The observation of pXL2666 multimers in the strain BW19610 (pir116) (Metcalf et al., 1993) led us to study the effect of the cer fragment from ColE1 on this phenomenon. We then introduced the expression cassette of the phenylalanine suppressor tRNA (sup Phe) onto the vector ori γ-$Km^R$-cer (pXL2730). This vector, pXL2760, serves as a basis for the construction of vectors which can be used in gene therapy.

Figure 4:
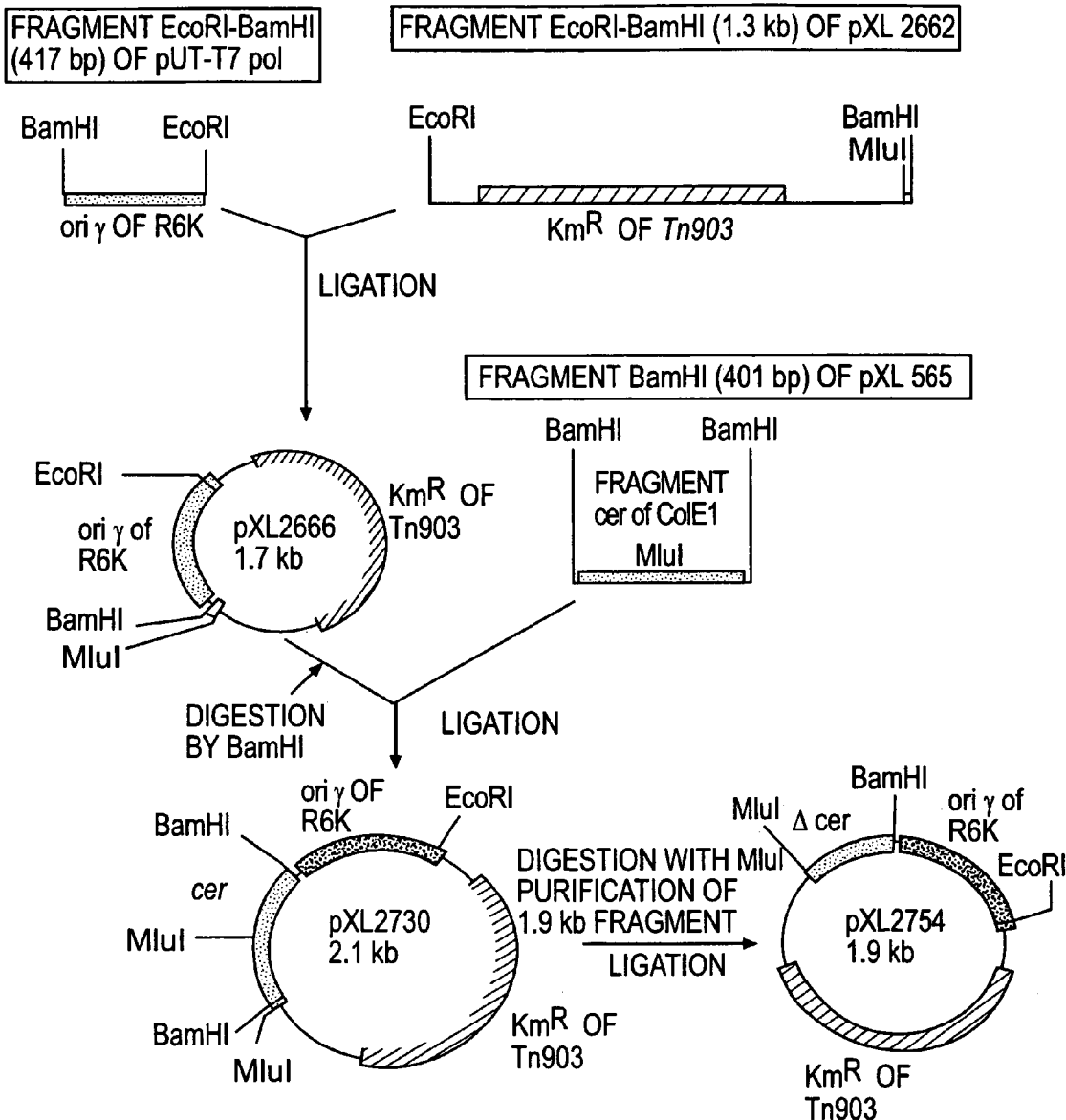
FIG. 4: Construction scheme for vectors pXL2666, 2730 and 2754.

1) Construction and Analysis of Vectors Containing ori γ from R6K and the Kanamycin Resistance Gene a) Constructs In the first plasmid constructed, pXL2666, the kanamycin resistance gene originated from pUC4K (Vieira and Messing; 1982) and the origin of replication, contained in a 417 bp EcoRI-BamHI fragment, originated from the suicide vector pUT-T7pol (Herrero et al., 1990) (FIG. 4). The transfer of pXL2666 into the strains BW19094 and 19610 (Metcalf et al., 1994) made it possible to show that the amount of plasmid is indeed increased in a pir116 strain, when compared with the same plasmid in a pir strain. However, electrophoretic analysis of the undigested plasmids showed that this increase goes hand in hand with the appearance of a few multimeric forms. This phenomenon is quite probably associated with intermolecular recombination between the multiple copies of the plasmid. Thus, we constructed pXL2730 by cloning the cer fragment of the natural *E. coli* plasmid, ColE1, which had been shown to permit, in cis, the resolution of plasmid dimers (Summers and Sherrat, 1984), into pXL2666. The fragment used corresponds to a 382 bp HpaII fragment from ColE1 (Leung et al., 1985). It contains a specific intermolecular recombination site; in order to function, it involves only host proteins including the recombinases XerC and XerD and the accessory factors ArgR and PepA (Stirling et al., 1988, 1989; Colloms et al., 1990). To ensure that the effects observed are indeed due to the cer fragment, we also constructed the control plasmid pXL2754, in which the cer fragment has a 165 bp deletion. This deletion was shown to abolish the action of cer on the resolution of the multimers (Leung et al., 1985). The various cloning steps leading to the construction of these plasmids are presented in FIG. 4.

b) Quantitative and Qualitative Analysis of the Plasmid Species (i) Analysis by Agarose Gel Electrophoresis Electrophoretic analysis of the different plasmids constructed allowed the demonstration of various plasmid species, which are variable according to the strains used. The size of the undigested plasmids was evaluated relative to a supercoiled DNA marker. In the pir strain (BW19094), the plasmids pXL2666, 2754 and 2730 were almost entirely in monomeric form. The bands above each main band correspond to various slightly less supercoiled topoisomers, as confirmed by the profile observed after the action of DNA gyrase on pXL2730.

In the case of the pir116 strain (BW 19610), the profiles were different: with the plasmids pXL2666 and 2754 different species were observed ranging from the monomer to multimers (2, 3 or 4 units), the major form being the dimer. After digestion with EcoRI, only the linear plasmid DNA was found; these plasmid species correspond either to plasmid multimers or to various topoisomers. However, since the size of the forms determined according to the supercoiled DNA marker was a whole product of that of the monomer plasmid, it is highly probable that they are multimers. The formation of multimers was most probably attributable to the pir116 mutation, although the two strains BW19094 and BW19610 are not strictly isogenic (BW19610 is recA). The profile obtained with pXL2730 was different: although multimeric forms were still visible, the major form is the monomeric form. The cer fragment can thus facilitate resolution of the plasmid multimers which we have constructed, independently of recA, in BW 19610.

(ii) Analysis After Treatment With DNA Topoisomerases

To disprove the theory that the forms observed in the strains carrying the pir116 allele are specific topoisomers, each plasmid preparation was subjected to the action of DNA topoisomerases. The activities of the various enzymes under the experimental conditions were as follows: relaxing of DNA for *E. coli* DNA topoisomerase I, negative supercoiling of relaxed DNA for *E. coli* DNA gyrase, and disentanglement of interlaced DNAs and relaxation of supercoiled DNA by *S. aureus* DNA topoisomerase IV. The action of DNA topoisomerase IV made it possible to show that the high-molecular-weight plasmid forms did not result from the entanglement of several plasmid molecules; in this case, they would then have been converted into the monomeric species. The functionality of the enzyme was, of course, checked on a preparation of kinetoplast DNA, composed of entangled DNA molecules (not shown). The relaxation activity was also visible since species are obtained which migrate less than in the untreated controls. The action of DNA gyrase made it possible to convert the slightly relaxed topoisomers into the more supercoiled species extracted from the bacterium (monomer or dimer mainly). Furthermore, it made it possible to verify that the DNAs prepared were mainly in supercoiled form. The samples thus treated allowed the above results to be confirmed as regards the major species for each construct. DNA topoisomerase I did indeed relax DNA, but only partially. This could be due to the fact that the plasmids studied contain only a few single-stranded regions, to which this enzyme preferably binds (Roca, 1995).

2) Introduction of the Selection Marker sup Phe into pXL2730

Figure 5:
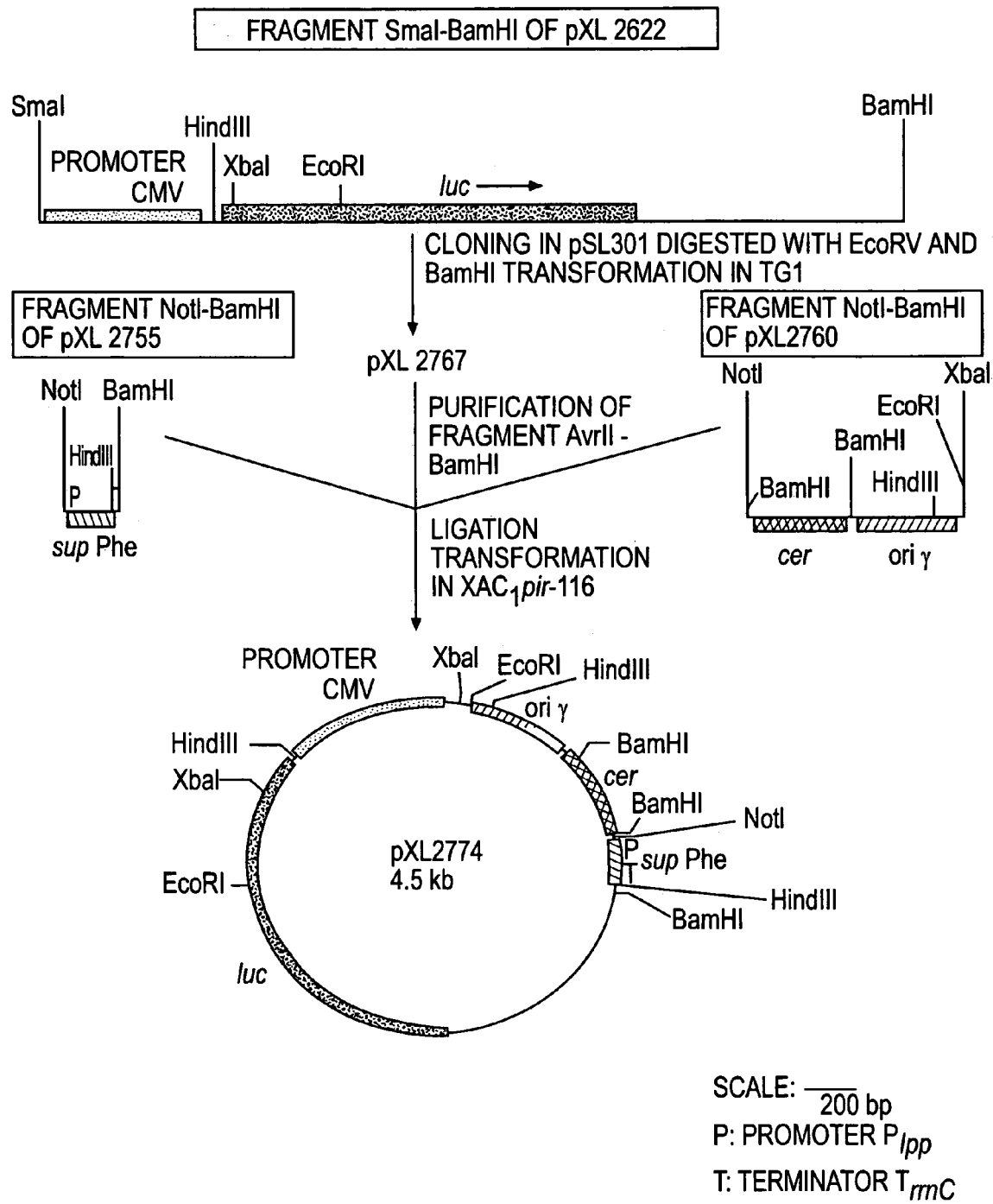
FIG. 5: Construction of pXL2774.

We used the expression cassette of the synthetic suppressor tRNA gene (Phe) (Kleina et al., 1990). This introduced a phenylalanine into the growing polypeptide chain in response to a TAG codon. Furthermore, it allowed the production in XAC-1 of an ArgE protein that was sufficiently active to allow good growth in arginine-deficient medium. sup Phe was expressed constitutively on the plasmid pCT-2-F (Normanly et al., 1986) from a synthetic promoter derived from the promoter sequence, Plpp, of the *E. coli* lpp gene. Downstream of this gene, transcription was stopped by the synthetic terminator, $T_{rrC}$, of the *E. coli* operon rrnC (Normanly et al., 1986). The various cloning steps are indicated in FIG. 5.

The various subclonings were performed in XAC-1. The functionality of the suppressor tRNA expression cassette was thus checked by means of the α-galactosidase activity of this strain, which only exists if there is suppression of the amber codon of the gene $lacZ_{u118am}$. The final step consists of the introduction of the sup Phe expression cassette into pXL2730. The results obtained with the cer fragment (B-1-b) led us to select this plasmid rather than pXL2666. We retained the kanamycin resistance gene for ease of subsequent cloning, in particular in order to have available additional screening during the final cloning (loss of $Km^R$).

EXAMPLE 3

Validation of the Plasmid Vector for Applications in Gene Therapy by Transfection of Mouse Fibroblasts 1) Construction of the Reporter Vector pXL2774

Figure 6:
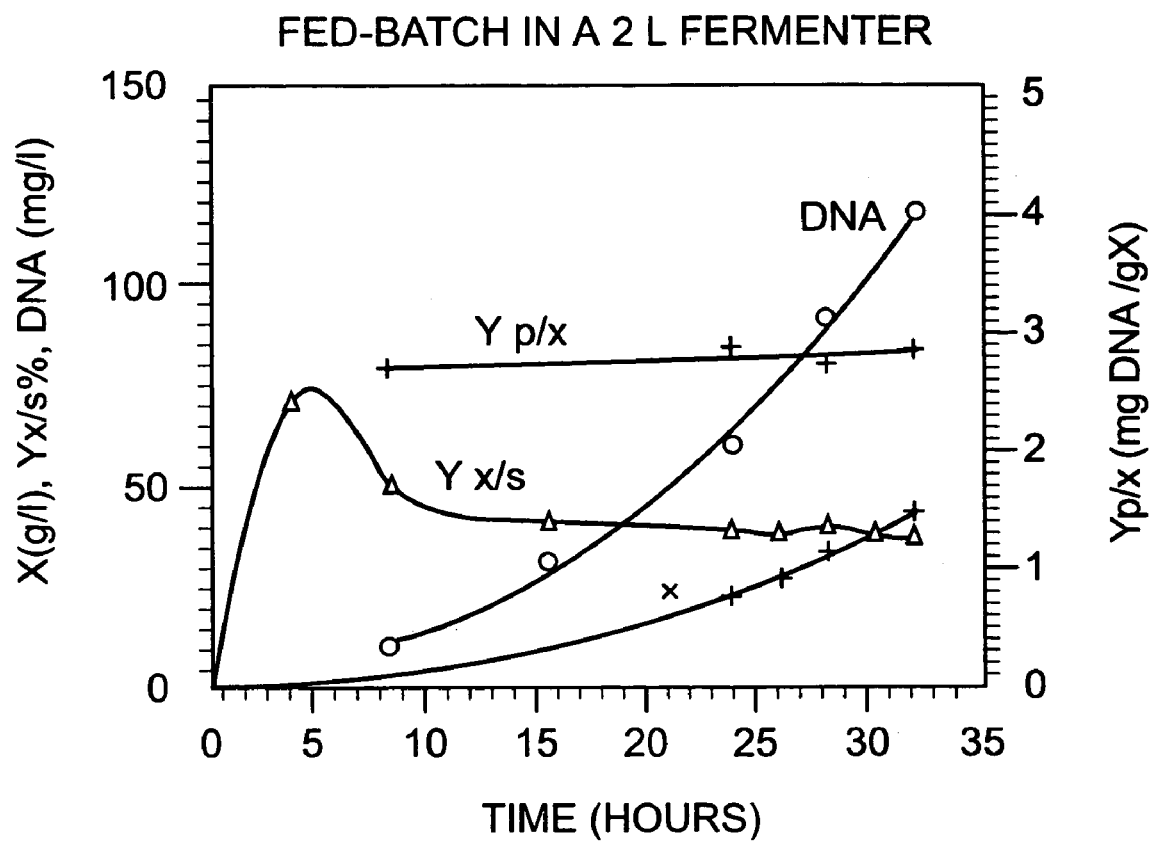
FIG. 6: Growth and production kinetics in a 2 L fermenter.

To test the validity for gene therapy of the system for producing plasmid DNA, we introduced a reporter gene, which can be used in eukaryotic cells, into pXL2760. We used the gene luc, which codes for *Photinus pyralis* luciferase, since the bioluminescence measurement test is very sensitive and is linear over a large range, and the background noise due to the endogenous activity of eukaryotic cells is very low. The luc gene was controlled by promoter-enhancer sequences of a human cytomegalovirus early gene (CMV promoter), which allowed a high level of expression. There was an untranslated region at the 3' end of luc, originating from the virus SV40, which contained the polyadenylation signal (poly(A)+). After intermediate cloning, which allowed the number of available restriction sites to be increased, the "CMV promoter-luc-poly(A)+" cassette was introduced into the minimal vector ori γ-cer-sup Phe (pXL2760) in place of the $Km^R$ marker. The resulting plasmid has been named pXL2774. FIG. 6 shows the various cloning steps. The ligation mixtures were transformed into XAC-1pir116 by electroporation. Incubation allowing the bacteria to express selection markers was carried out in rich medium (SOC medium); it was thus necessary to wash the cells twice with M9 medium before plating out. This made it possible to remove the residual medium, which would have resulted in culture background noise on minimal medium.

The medium chosen to plate out the electroporated cells was M9 minimal medium, which makes it possible to select bacteria expressing a suppressor tRNA and thus the presence of our plasmids. The addition of X-Gal made it possible, by means of the blue colouration, to visualize the expression of the suppressor tRNA. The dishes were analysed after about 20 hours at 37° C. The absence of colonies on the DNA-free control assures us that the selection was correct, even with dense seedings. All the clones examined by restriction (8) do indeed carry a plasmid, corresponding to the expected profile. The plasmid thus constructed, pXL2774, was prepared from a clone cultured in one liter of liquid M9 medium (about 18 hours at 37° C.), by a technique involving, inter alia, an ion-exchange step (Promega kit, MegaPreps). The amount of DNA collected was 2 mg.

2) Analysis of the Reporter Vector pXL2774 Transfected into Mammalian Cells.

The capacity of pXL2774 to transfect eukaryotic cells and to allow the expression of luciferase was evaluated by transfection into NIH 3T3 mouse fibroblasts. The vector chosen as reference was the plasmid pXL2622 (this is the plasmid pGL2 from Promega whose SV40 promoter has been replaced by the CMV promoter), which carries the same luciferase expression cassette as pXL2774, but on a different replicon. This is a 6.2 kb ColE1 derivative which carries the ampicillin-resistance gene. This plasmid serveed as a control. The luciferase activities (expressed as RLU, or relative luminescence units) are indicated in Table 3.

The best results were obtained with a "lipofectant charges/DNA charges" ratio of 6; under these conditions, pXL2622 and 2774 appear to be equivalent.

TABLE 3

| | pXL2622 | | | pXL2774 | | |
|---|---|---|---|---|---|---|
| Charge ratios | RLU/μg of proteins and per well | Average | Coefficient of variation (%) | RLU/μg of proteins and per well | Average | Coefficient of variation (%) |
| 0 | 0.0<br>0.0<br>0.0 | not detectable | | 0.0<br>0.0<br>0.0 | not detectable | |
| 3 | $9.9\ 10^6$<br>$6.2\ 10^6$<br>$6.6\ 10^6$ | $7.6\ 10^6$ | 22 | $3.3\ 10^6$<br>$2.9\ 10^6$<br>$2.4\ 10^6$ | $2.9\ 10^6$ | 13 |
| 6 | $1.2\ 10^7$<br>$1.5\ 10^7$<br>$1.9\ 10^7$ | $1.5\ 10^7$ | 19 | $9.4\ 10^6$<br>$9.9\ 10^6$<br>$1.1\ 10^7$ | $1.0\ 10^7$ | 7 |
| 9 | $9.5\ 10^6$<br>$7.5\ 10^6$<br>$1.4\ 10^7$ | $1.0\ 10^7$ | 26 | $1.1\ 10^7$<br>$8.3\ 10^6$<br>$8.5\ 10^6$ | $6.4\ 10^6$ | 13 |

EXAMPLE 4

Verification of the Suicide Vector Nature in *E. coli* of the pCOR Plasmids

The non-replicative nature of the pCOR-type plasmids derived from R6K was verified by an electroporation experiment in JM109 *E. coli* (Yanisch-Perron et al., 1985) of plasmids pUC4K (ori ColEI-KmR, (Vieira and Messing, 1982)) and pXL2730 (ori gamma from R6K-KmR, see Example 2). The electroporator used was the Biorad Gene Pulser and the electrocompetent JM109 cells were prepared and used according to the manufacturer's procedure (Bacterial electro-transformation and pulse controller instruction manual. catalog number 165-2098).

The electrotransformed cells were plated out on LB medium supplemented with kanamycin (50 mg/l) and incubated overnight at 37° C. The results obtained are presented below.

Results

| Plasmid | Amount transformed (ng) | Number of transformants | Efficacy (number of transformants/ ng of plasmid) |
|---|---|---|---|
| pUC4K | 0.01 | >>2000 | >2105 |
| pXL2730 | 5 | 0 | 0 |

These results show that there was a minimum of 5 logs of difference between the efficacy of transformation of a ColEI derivative (pUC4K) and that of an R6K derivative (pXL2730) in a strain which does not express the pir gene. In a pir+ strain such as XAC-1pir116, the electrotransformation efficacy of R6K-derived plasmids conventionally reaches or exceeds the 108 transformants/μg of plasmid.

EXAMPLE 5

Production of Plasmid DNA by High-Density Culturing of the *E. coli* Strain XAC-1pir116 (pXL2774): Fermentation Process 5.1. Strains:

Production in XAC-1pir116 *E. coli* (Example 1) of a minimal plasmid, pXL2774; this plasmid comprises the following elements: ori R6K-cer-tRNAamsupPhe and an expression cassette of the luc reporter gene under the control of the CMV promoter (Example 3). A high-productivity process for the production of plasmids of this type was developed.

5.2. Culturing Media and Conditions:

a) Growth Medium:

Composition of the medium defined used for the inoculum cultures (g/l): $Na_2HPO_4$ 6, $KH_2PO_4$ 3, NaCl 0.5, $NH_4Cl$ 1, $NH_4H_2PO_4$ 3, glucose 5, $MgSO_4.7H_2O$ 0.24, $CaCl_2.2H_2O$ 0.015, thiamine HCl 0.010

Composition of the complex medium used for the fed-batch cultures (g/l): $KH_2PO_4$ 8, $K_2HPO_4$ 6.3, $Na_2HPO_4$ 1.7, $(NH_4)_2SO_4$ 0.74, $NH_4Cl$ 0.12, yeast extract 3, glucose 2, $MgSO_4.7H_2O$ 2.4 g/l, $CaCl_2.2H_2O$ 0.015, thiamine 0.010, solution of salts (Fe, Mn, Co, Zn, Mo, Cu, B, Al).

Composition of the medium defined for the cultures in fed-batch medium identical to the complex medium, but the yeast extract is replaced by 2.5 μl of $NH_4Cl$.

b) Conditions of Fed-Batch Culturing:

Studies in 2-liter fermenters (Setric France) containing 1 l of medium were carried out in order to define the optimum conditions for growing and producing plasmid DNA. The fermenter was inoculated with 80 ml of an inoculum culture arrived at the start of the stationary phase of growth.

During the fermentation, the pH was controlled and adjusted automatically between 6.9 and 7.0 with 10% (w/v) aqueous ammonia; the temperature was maintained at 37° C.; the aeration was set at 75 l/h ((1.1 vvm) at a pressure of 0.2 bar and the dissolved oxygen was adjusted to (40% of air saturation by retroaction on the stirring rate and, if necessary, by enrichment with pure oxygen.

All the parameters (pH, temperature, stirring, OD, $O_2$ and $CO_2$ in the effluent gases) were collected and calculated in line via an HP3852 interface connected to a Hewlett-Packard 9000.

The base composition of the supply medium was as follows: 50% carbon source, 0.7% magnesium sulphate, 0.02% thiamine; for the complex medium, yeast extract was added to a concentration preferably of between 5 and 10%.

To adapt the culture conditions to 800-liter fermenters, production sequences composed of two successive inoculum cultures were carried out, on a laboratory scale: inoculum I in an agitated conical flask and inoculum II in a 2-liter fermenter (batch culturing), followed by fed-batch production culturing, in a 7-liter fermenter.

5.3. Results

Various culture conditions were studied in complex medium, in defined medium, and at various growth rates. In all cases, after initial batch culturing of the bacterial strain and consumption of the carbon source, the supply medium was added to the fermenter by means of a peristaltic pump coupled to a pre-programmed addition profile. This profile was deduced from previous experiments in which the supply rate had been controlled either by the level of dissolved oxygen or by a constant growth rate.

Furthermore, in order to extrapolate without difficulty the 2-liter fermentation condition to an 800l fermenter without overoxygenation of the medium, the maximum oxygen demand at the end of the culturing was set at 2.5-3 mM/min. For this, the growth rate of the microorganism was reduced, if necessary, by varying the supply rate of the complementary charge.

Figure 7:
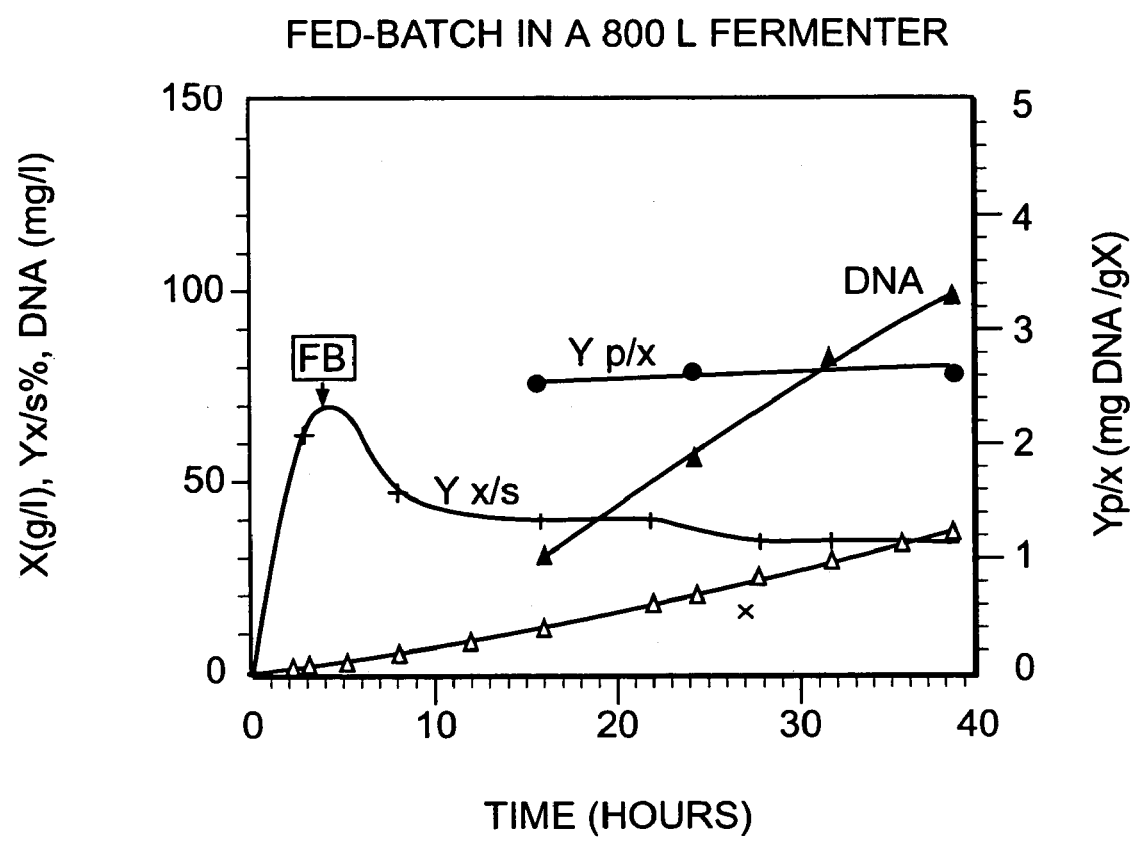
FIG. 7: Growth and production kinetics in an 800 L fermenter.

As seen in Table 4, very good results were obtained both in complex medium and in defined medium, both on the laboratory scale and on the 800-liter fermenter scale; furthermore, the plasmid DNA growth and production kinetics are entirely comparable (cf. FIGS. 6 and 7).

TABLE 4

| | Complex medium | | Defined medium |
|---|---|---|---|
| | 2 or 7 l fermenter | 800 l fermenter | 2 l fermenter |
| Duration of fermentation (hours) | 40 | 39 | 48 |
| μh-1 | 0.130 | 0.132 | 0.124 |
| OD (600 nm) | 114 | 100 | 94 |
| X g/l | 44 | 37 | 30 |
| Plasmid DNA (mg/l medium) | 115 | 100 | 100 |
| Plasmid DNA (mg/gX) | 2.6 | 2.7 | 3.3 |

X = Biomass (weight of dry cells)

From the overall results it emerges that:
- changing the scale of the fermenter from 2 liters to 800 liters can be carried out without any problem,
- the oxygen consumed is strongly correlated to the biomass produced (1.08 g $O_2$/g of biomass produced),
- the plasmid was stable for at least 50 generations without selection pressure,
- a high biomass, greater than 40 g of dry cells/liter, can be obtained in complex medium,
- the plasmid DNA production reaches 100 mg of supercoiled DNA/l of medium,
- there was very good correlation between the DNA production and the biomass: the production can be estimated to (1 mg of plasmid DNA/OD unit, or alternatively (2.7 mg of plasmid DNA/g of biomass, irrespective of the duration of fermentation,
- the use of a defined medium also makes it possible to achieve a high biomass (30 g of dry cells/l) and high plasmid DNA production (100 mg/l), without any loss of productivity.

EXAMPLE 6

Transfer of pXL2774 into Animal Cells, In Vitro and In Vivo

6.1. In Vitro Transfer of pXL2774 into Animal Cells

The capacity of the minimal plasmid pXL2774 to transfect various cell lines was tested in vitro, on cells of both human origin and murine origin. The pXL2784 plasmid was used as control. It contains the same eukaryotic expression cassette (CMV promoter-luciferase-polyA) as pXL2774, but this is a 6.4 kb ColE1 derivative which comprises the gene for imparting kanamycin resistance in *E. coli*.

The cells tested are the following:

| Cells | Type | Atcc ref./ literature ref. |
|---|---|---|
| 3LL | Mouse pulmonary carcinoma | |
| NIH 3T3 | Mouse embryo fibroblasts | CCL92 |
| 293 | Human embryo renal cells transformed with type-5 adenovirus | CRL1573 |
| HeLa | Human carcinoma from the neck of the womb | CCL2 |
| Caco-2 | Human colon adenocarcinoma | HTB37 |
| H460 | Human lung carcinoma with no small cells | HTB177 |
| ECV 304 | Human umbilical cord endothelial cells | Takahashi et al., 1990 |

The transfection conditions were as follows:

D-1: Inoculation of the cells at a density of 100,000 cells per 2 cm$^2$ well (24-well plate) in DMEM medium (Dulbecco's modified Eagle Medium) supplemented with 10% fetal calf serum (FCS).

D-3: Transfection of the cells, by 10 µl of a transfection solution containing: 0.5 µg of DNA, 150 mM NaCl, 5% glucose and 3 nmol of RPR120 535 lipofectant per µg of DNA, in 250 µl of culture medium, which was or was not supplemented with 10% FCS. After incubation for 2 hours, the medium was replaced by 500 µl of DMEM medium supplemented with 10% FCS.

D-4: Renewal of the culture medium

D-5: Wash of the cells with PBS, followed by lysis with 100 µl of Promega lysis buffer (Promega Cell Lysis Buffer E153 A). Assay of the luciferase activity was carried out in a Lumat LB 9501 luminometer (Berthold) on 10 µl of lysate, with a 10-second duration of intergration. The reactant used was that from Promega (Promega Luciferase Assay Substrate). The results, collated in the following tables 5-8, are expressed in RLU (Relative Lights Units) for 10 µl of lysate (average measurement on 4 wells). The coefficients of variation (CV) are also given.

The results of transfections in the absence of serum are presented below.

| | CELL TYPES | | | | | | |
|---|---|---|---|---|---|---|---|
| | NIH 3T3 | 3LL | 293 | | HeLa | CaCo2 | H460 | ECV304 |
| pXL2774 | 37 763 380 | 559 270 | 1 884 200 | RLU | 11 000 000 | 1 108 422 | 1 459 501 | 36 450 |
| | 16 | 25 | 73 | CV | 15 | 14 | 5 | 23 |
| pXL2784 | | 113 764 | 1 723 546 | RLU | 557 930 | 93 610 | 7 563 | 168 795 |
| | | 24 | 101 | CV | 87 | 40 | 11 | 40 |

| | CELL TYPES | | | | | |
|---|---|---|---|---|---|---|
| | NIH 3T3 | 3LL | 293 | HeLa | H460 | ECV304 |
| pXL2774 | 50 612 590 | 566 377 | 992 500 | 9 490 000 | 857 385 | 18 021 |
| | 12 | 18 | 59 | 25 | 16 | 30 |
| PXL2784 | 12 693 780 | 436 704 | 2 300 000 | 1 508 480 | 433 023 | 32 074 |
| | 38 | 12 | 47 | 23 | 27 | 47 |

These results reveal the capacity of pXL2774 to transfect effectively, in vitro, various cell types of both murine and human origin. The expression of the luc reporter gene made it possible to show that its transfection efficacy is at least as good as that of a "standard" plasmid, derived from ColE1, which carries the same expression cassette of luciferase.

6.2 In Vivo Transfer, in Animals (Mice), of pXL2774 a) Model 1: Naked DNA in Mouse Cranial Tibial Muscle

Naked plasmid DNA, dissolved in "5% glucose, 150 mM NaCl" was injected into the cranial tibula muscle of OF1 mice. The muscles were removed 7 days after injection, chopped up, homogenized in 750 µl of the lysis buffer (Promega Cell Lysis Buffer E 153A) and then centrifuged at 20,000×g for 10 minutes.

Assay of the luciferase activity was carried out on 10 µl of supernatant after addition of 50 µl of reagent (Promega Luciferase Assay Substrate). The reading was carried out on a Lumat LB9501 luminometer (Berthold) with a 10-second duration of integration.

The results are presented in the table below.

| | Plasmid | | | |
|---|---|---|---|---|
| | pXL2784 | pXL2774 | pXL2784 | pXL2774 |
| Number of muscles: | 8 | 8 | 10 | 10 |
| Volume injected (il): | 30 | 30 | 33 | 33 |
| µg of DNA/muscle | 19 | 13.5 | 10 | 6.25 |

-continued

| | Plasmid | | | |
|---|---|---|---|---|
| | pXL2784 | pXL2774 | pXL2784 | pXL2774 |
| | RLU (for 10 µl) | | | |
| Average | 80 922 | 471 733 | 35329 | 30569 |
| Standard deviation | 104 573 | 402 602 | 37041 | 35774 |

These results show that a conditional replication plasmid such as pXL2774 was indeed capable of transfecting mouse muscle cells in vivo and of doing so with comparable, or even superior, efficacy to that of a "standard" plasmid derived from ColE1, which carries the same expression cassette of the luciferase gene.

b) Model 2: 3T3 HER2 Tumour Model

The model is as follows:

Swiss/nude adult female type mice

Experimental tumours induced after injection of 107 3T3 HER2 cells subcutaneously into the flank.

The transfection mixture was injected 7 days after injection of the cells.

Solutions injected: The DNA was first dissolved in the buffer. After addition of all the products, the mixture contained, besides the DNA, NaCl (150 mM) and 5% D-glucose in water or 5 mM HEPES buffer.

Two days after the injection, the tumour tissue was removed, weighed and then chopped up and homogenized in 750 il of lysis buffer (Promega Cell Lysis Buffer E153 A).

After centrifugation (20,000×g for 10 minutes), 10 µl of supernatant was removed and luciferase activity was evaluated. This activity was determined by measuring the total light emission obtained after mixing with 50 µl of reagent (Promega Luciferase Assay Substrate) in a Lumat LB 9501 luminometer (Berthold) with a 10-second duration of integration.

The resulting activity was expressed in RLU (Relative Light Units) estimated in the entire tumour lysis supernatant.

| | | Results | | | |
|---|---|---|---|---|---|
| | | Plasmid | | | |
| Buffer | | [DNA] | RLU/tumour results | | |
| H20 or HEPES | reference | final in µg/tumour inj. sol. | average | standard deviation | +/n |
| HEPES | pXL2784 | 10 0.5 µg/µl | 744 150 | 682 434 | 6/6 |
| | pXL2774 | 10 0.5 µg/µl | 1 016 380 | 1 322 500 | 5/6 |
| H2O | pXL2784 | 24 0.6 µg/µl | 2 906 073 | 1 745 857 | 8/8 |
| | pXL2774 | 16.8 0.4 µg/µl | 4 292 043 | 4 995 187 | 6/6 |
| H2O | pXL2784 | 7.5 0.3 µg/µl | 702 554 | 552 207 | 6/7 |
| | pXL2774 | 5 0.2 µg/µl | 3 413 430 | 4 000 875 | 6/6 |

These results show that a conditional replication plasmid, such as pXL2774, was indeed capable of transfecting mouse tumour cells in vivo and of doing so with an efficacy at least comparable to that of a "standard" plasmid, derived from ColE1, which carries the same expression cassette of the luciferase gene.

These various experiments demonstrate that the conditional replication plasmids, and more particularly pXL2774, did indeed have animal cell transfection characteristics that are essential for use in gene therapy. More precisely, the following were shown:

1) the capacity of pXL2774 to transfect efficiently, in vitro, various cell types of human or murine origin;
2) the capacity of pXL2774 to transfect, in vivo, mouse muscle;
3) the capacity of pXL2774 to transfect, in vivo, tumour cells implanted into mice.

The electrotransformation, fermentation and transfection experiments thus made it possible to validate conditional replication plasmids as vectors which can be used in gene therapy by showing:

i) that they did not replicate detectably in an *E. coli* strain that does not express the pir gene (conditional origin of replication)

ii) that they could be produced on a scale compatible with industrial production, in a defined medium that does not contain antibiotics;

iii) that these plasmids could transfect, in vitro and especially in vivo, mammalian cells.

EXAMPLE 7

In Vitro Production of Recombinant Proteins 7.1. Construction of the Expression Vector To show the feasibility of such an approach, we constructed an expression vector according to the criteria described above (Examples 2 and 3). This vector, pXL3056, contains:

1) the bacterial part which comprises the conditional origin of replication (ori gamma), the cer fragment of ColE1, and the gene which ensures selection in bacteria (sup)

2) the expression cassette, based on the system described by Studier (Studier et al., 1990), comprising the promoter of gene 10 of bacteriophage T7, the lacO operator, the gene coding for aFGF 154 (acidic Fibroblast Growth factor, form containing 154 amino acids) (Jaye et al., 1986), and the TF terminator of bacteriophage T7. This expression cassette is identical to the one present on the pXL2434 plasmid, which is described in application WO 96/08572.

Figure 8:
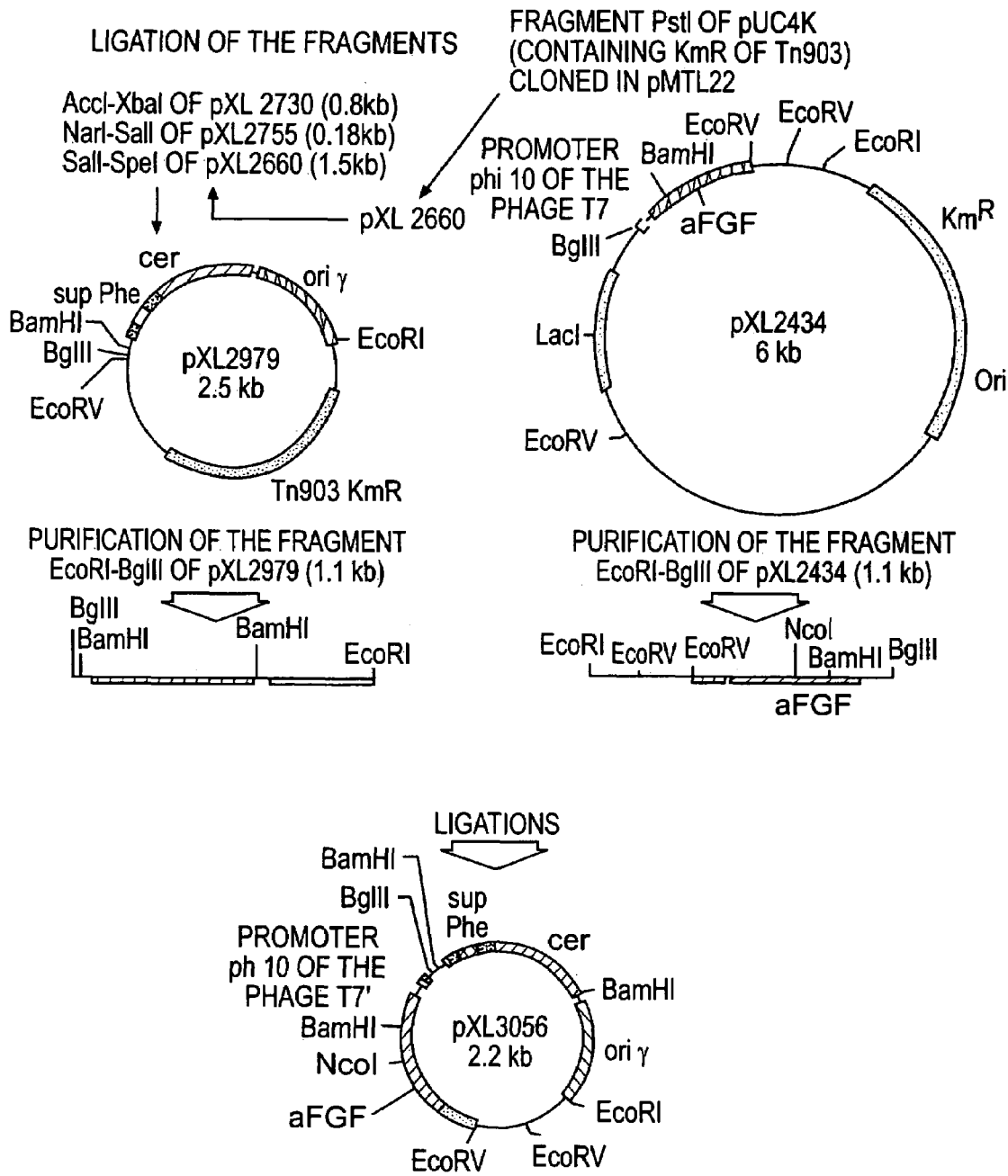
FIG. 8: Construction of pXL3056.

The construction of pXL3056 is presented in FIG. 8. The EcoRI-BglII fragment of pXL2434 (1.1 kb) containing the aFGF expression cassette was cloned in the pXL2979 conditional replication vector (1.1 kb purified fragment) at the BglII and EcoRI sites to generate pXL3056.

pXL2979 results from the ligation of 3 fragments: i) AccI-XbaI fragment of pXL2730 (0.8 kb, which provides ori gamma and cer), ii) NarI-SalI fragment of pXL2755 (0.18 kb, which provides the sup Phe gene), iii) SalI-SpeI fragment of pXL2660 (1.5 kb, which provides the kanamycin resistance gene).

pXL2660 results from the cloning of the 1.2 kb PstI fragment of pUC4K (Vicira and Messing, 1982) in pMTL22 (Chambers et al., 1988) linearized with PstI.

7.2. Production of the Expression Strain

Plasmid pXL3056 was introduced by transformation into the XAC-1pir116 strain. The resulting strain was then transformed by the plasmid PT7pol23 (Mertens et al., 1995), at 30° C. In order to express the gene of interest under control of the T7 promoter, the bacterium must contain in its genome, on a plasmid, or a bacteriophage, a cassette allowing expression of the RNA polymerase of bacteriophage T7. In the example described, we used the plasmid pT7pol23, which is compatible with R6K derivatives such as pXL3056, and which allows the temperature-inducible expression of bacteriophage T7 RNA polymerase. However, it can also be envisaged to lysogenize the XAC-1pir116 strain with lambda DE3 (Studier et al., 1990) to conserve only one plasmid and to induce the production of T7 RNA polymerase by IPTG rather than by temperature.

7.3. Expression of aFGF

The XAC-1pir116 strain (pXL3056+PT7pol23) was cultured at 30° C. in M9 minimum medium supplemented with 0.2% of casamino acids (DIFCO) and kanamycin (25 µg/ml), up to an optical density at 600 nm of 0.6-1.0. Half of the culture was then placed at 42° C. (induction of the T7 RNA polymerase), while the other half remained at 30° C. (negative control). The same experiment was carried out with the XAC-1pir116 (pXL3056+pUC4K) strain which constitutes a control for the expression of aFGF in the absence of T7 RNA polymerase.

Figure 9:
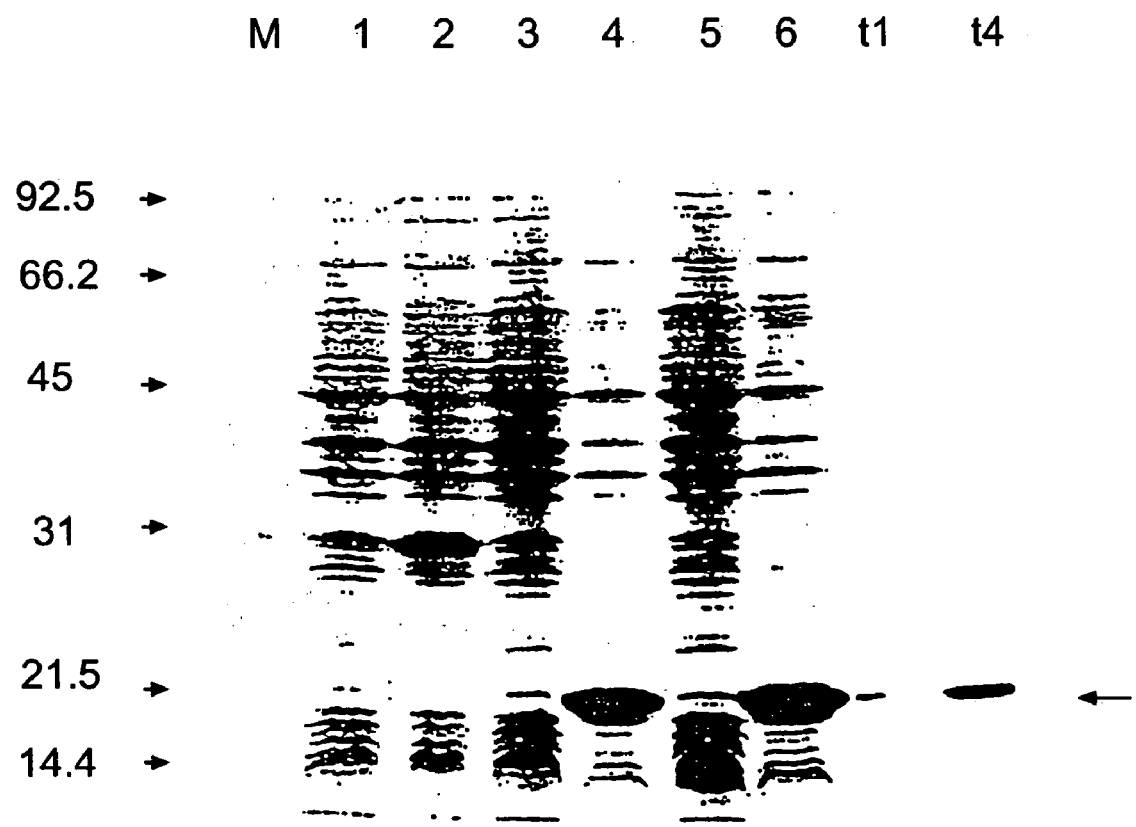
FIG. 9: Visualization of the aFGF protein produced by E. coli XAC-1pir116 (pXL3056+PT7pol23) after induction. The denatured total cell extracts are deposited on 12.5%-SDS polyacrylamide gel. M: molecular mass marker (Biorad, Low range). Each band is identified by an arrow and a figure which indicates its mass in kDaltons. 1: XAC-1pir116 (pXL3056+pUC4K) not induced; 2: XAC-1pir116 (pXL3056+pUC4K) induced at 42° C.; 3: XAC-1pir116 (pXL3056+PT7pol23) clone 1, not induced; 4: XAC-1pir116 (pXL3056+PT7pol23) clone 1, induced at 42° C.; 5: XAC-1pir116 (pXL3056+PT7pol23) clone 2, not induced; 6: XAC-1pir116 (pXL3056+PT7pol23) clone 2, induced at 42° C.; t1: 1 µg of purified aFGF; t4: 4 µg of purified aFGF.

The results obtained are presented in FIG. 9. They show that the production of aFGF was comparable or superior to that observed with BL21(DE3)(pXL2434) (WO 96/08572), which clearly shows the potential of conditional replication plasmids for the expression of recombinant proteins in vitro, especially in *E. coli*.

EXAMPLE 8

Construction of a pCOR Vector Which Expresses a Wild-Type or Hybrid p53 Protein or the FGF1 Human Protein This example describes the construction of conditional replication vectors according to the invention containing a nucleic acid coding for a p53 protein. These vectors can be used to restore a p53-type activity in deficient (mutated, deleted) cells such as, in particular, tumour cells.

The eukaryotic expression cassette contains the following elements:

1) CMV "immediate early" promoter (positions −522 to +72) followed by the leader sequence of the thymidine kinase gene of type I herpes simplex virus (position −60 to +1 of the gene, with reference to the sequence in the article by McKnight, S.†L. (1980) Nucleic Acids Res. 8:5949-5964);

2a) a nucleic acid which codes for wild-type p53 protein or for a p53 variant, as described in application PCT/FR 96/01111 (V325K variant=V325 with a Kozak sequence with ATG);

2b) a nucleic acid which codes for the human FGFa or FGF-1 as described in Jaye M. (Sciences 1986; 233 (4763): 451, U.S. Pat. No. 4,686,113, and European Patent No: 259 475;

2c) a nucleic acid which codes for a fusion gene between human fibroblast interferon secretion signal (Taniguchi et al.) and the naturally occurring truncated form of human FGF-1 from amino acid 21 to 154 as described by Jaye et al., and U.S. Pat. No. 5,849,538.

3) the polyA polyadenylation sequence of SV40.

These elements were placed in the form of a fragment AscI-XbaI on the pCOR vector pXL2988 between the sites BssHII and SpeI. pXL2988 is identical to pXL2979 (Example 7.1.) apart from the presence of an additional element, a sequence capable of forming a DNA triple helix composed of 17 copies of the trinucleotide GAA, placed alongside the gamma origin of replication.

Figure 10:
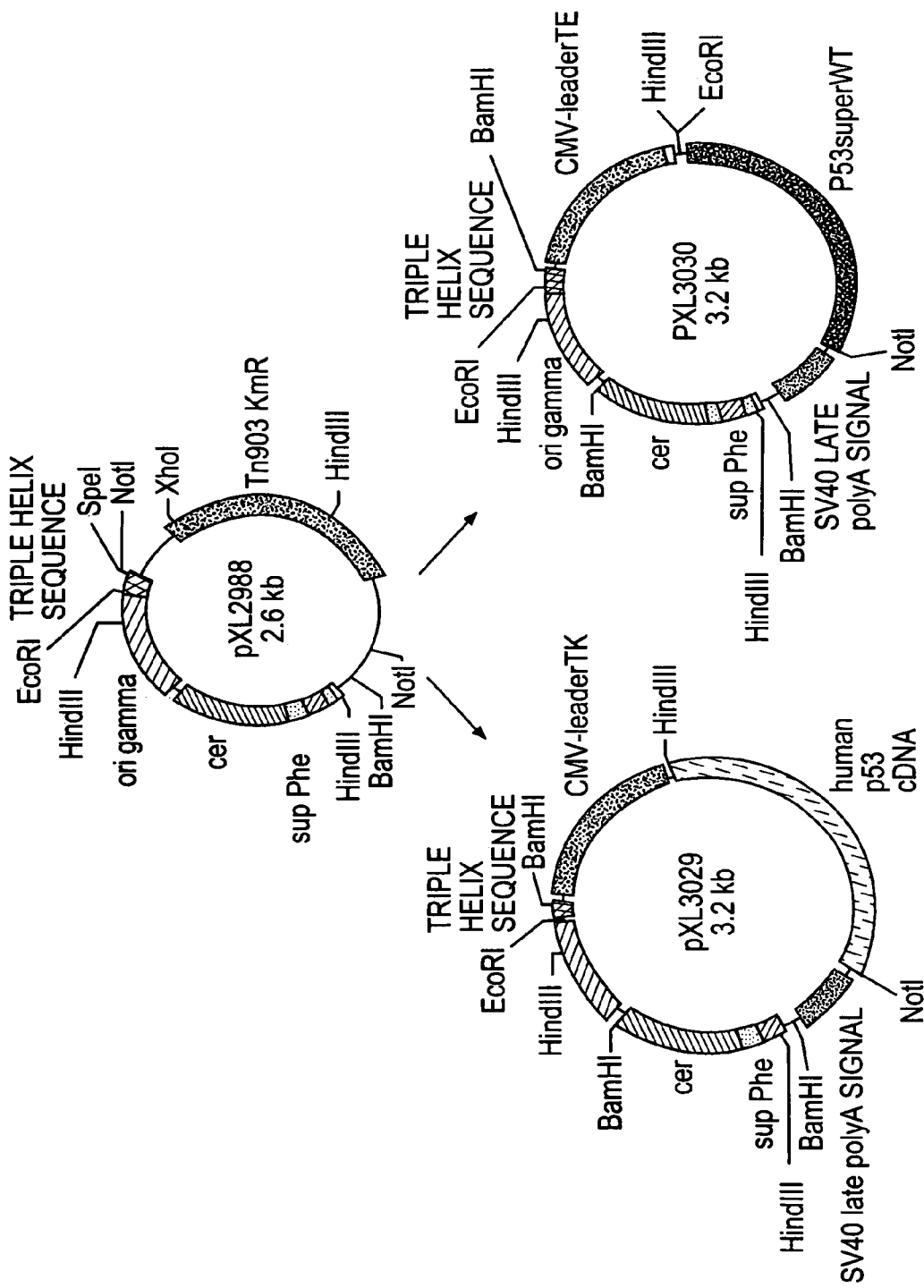
FIG. 10: Schematic representations for vectors pXL3029, pXL3030, and pXL3179 or NV1FGF.
Figure 11:
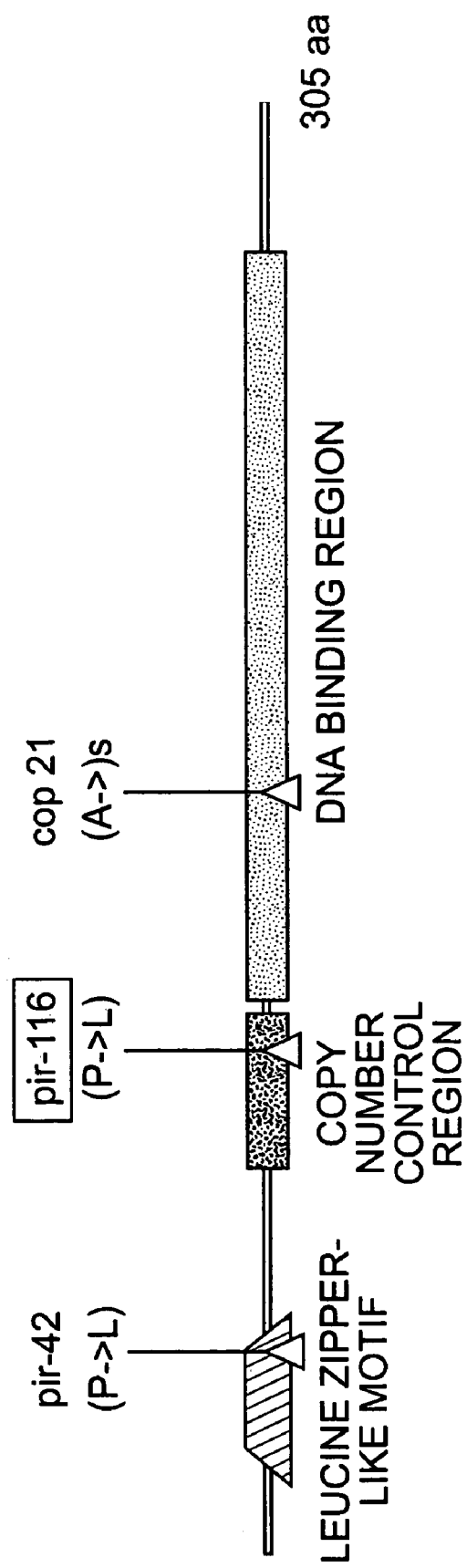
FIG. 11: Schematic representation of the functional domains of R6K π initiator proteins.

The resulting plasmids were named pXL3029, pXL3030, pXL3179 or NV1FGF (FIG. 10).

The functionality of these constructions was verified in vitro on p53-SAOS2 cells in culture by measuring the transcriptional-activator activity of p53 or p53superWT, or by measuring the secretion of FGF1 for example by ELISA experiments which is well known in the art.

EXAMPLE 9

Construction of TEX 1 (XAC1 pir116, endA$^-$, traD$^-$)

The *E. coli* XAC-1pir116 contains an F' episome, a circular DNA molecule of approximately 100 kb, that carries proB$^+$lacI$_{373}$lacZ$_{u118am}$. Many male *E. coli* laboratory strains carry a traD36 mutation on their episome, but no mutation affecting F' transfer ability has been described for XAC-1. The gene traD is at the 5' end of one of the tra (transfer) operons and encodes a membrane protein directly involved in DNA transfer and DNA metabolism (Frost et al., BBRC, 1994, 58:162-210). A 2 kb central fragment from traD, comprising 92% of the gene, was replaced with the 2 kb omega element (Genbank accession number M60473) from pHP45Ω (Prentki and Krisch, 1984, Gene, 29:303-313) by homologous recombination in XAC-1pir116 endA$^-$. The omega element contains the aadA antibiotic resistance gene flanked by short inverted repeats. The gene aadA encodes aminoglycoside-3 adenyltransferase and confers resistance to streptomycin and spectinomycin ("Sp$^R$"). The omega fragment was used because it prematurely terminates RNA and protein synthesis leading to the inactivation of the whole traD operon. This new pCOR strain XAC-1pir116 endA− traD::SpR was designated TEX1. Transfer of any resident plasmids, either pCOR or pUC, was undetectable when the donor was TEX1.

The new pCOR host strain TEX1 was assessed in fermentation experiments. Complex media containing yeast extract were used for fed-batch fermentation with XAC-1pir116. pCOR stability (more than 50 generations) makes it possible to use a non-selective media. Under these conditions, XAC-1pir116 produced more than 40 g/l dry cell weight and 100 mg/l of pCOR pXL2774 were obtained from 2-liter fermenters. pCOR copy number was estimated at 400-500 copies per cell and the rate of plasmid DNA synthesis was constant throughout fermentation. These results were extrapolated to an 800-liter fermenter suitable for manufacturing. The fermentation was also performed in the absence of yeast extract or any raw material from animal origin. Similar results (30 g/l dry cell weight and 100 mg/l of plasmid DNA) were obtained using a defined medium in 2-liter cultures with no loss of productivity.

EXAMPLE 10

Construction of XAC-1pir116pir42 Host Strains by Homologous Recombination

1) Construction of a Suicide Vector Carrying the Cassette "KmR-uidA:pir116; pir42"

The Km$^R$-uidA::pir116 cassette from M13wm33 as described in Example 1 (Metcalf W. et al. Gene, 1994, 138(1-2): p. 1-7), was modified by site-directed mutagenesis using PCR (QuickChange site-directed mutagenesis kit, Stratagene, La Jolla, Calif.) to introduce the pir42 mutation into the pir116 gene. The different cloning/mutagenesis steps are described in FIG. 13.

The oligonucleotides used for mutagenesis contained the pir42 mutation along with a silent mutation that created a ClaI site to easily indicate the processing of pir42 by restriction analysis when needed.

The sense and antisense oligonucleotides used are as follows:

Sense oligonucleotide number 11076 (SEQ ID NO: 7)

```
5'-G TAT ATG GCG CTT GCT CTC ATC GAT AGC AAA GAA CC-3'
                            pir42 ClaI
```

Antisense oligonucleotide number 11077 (SEQ ID NO: 8)

```
5'-GG TTC TTT GCT ATC GAT GAG AGC AAG CGC CAT ATA C-3'
                 ClaI pir42
```

Figure 13:
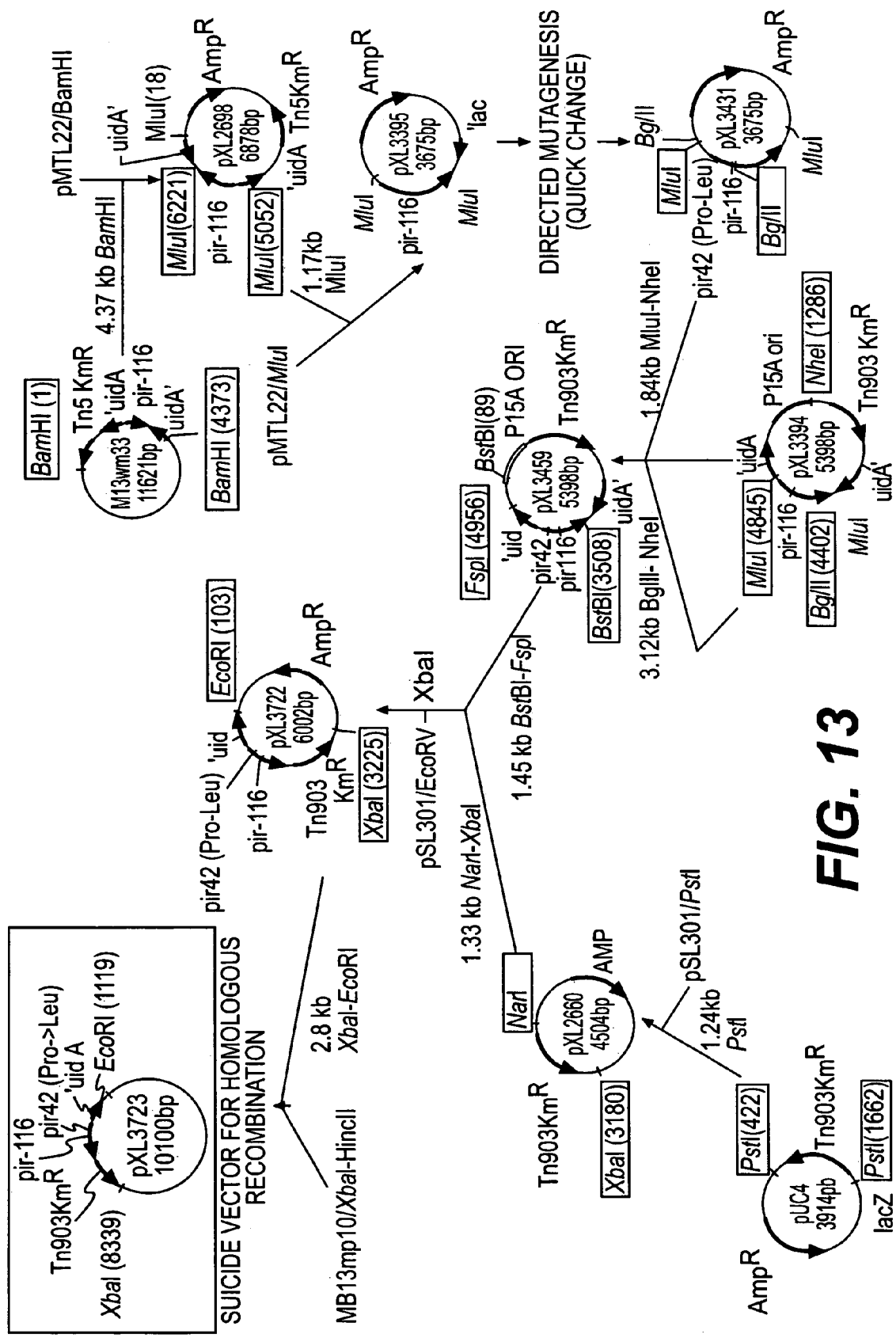
FIG. 13: Construction of pir116pir42 suicide vector for homologous recombination.

The technique used to replace pir116 by pir116pir42 in the genome of E. coli pCOR host TEX1 was based on that of Blum et al. (J. Bacteriol. 1989, 171, pp 538-46). The recombinant bacteriophage pXL3723 shown in FIG. 13 is a suicide vector in all non-suppressor E. coli strains, because it has a non-sense mutation in gene II encoding M13 nickase that prevents viral genome replication.

Double recombination was performed as described for the construction of XAC-1pir116 (Example 1, point 2). Clones that had undergone double homologous recombination events were screened by PCR to test for the presence of the pir42 mutation in the genome of TEX1. Genomic DNA isolated from double recombination candidates was used as a template for PCR. Secondly, sequencing was done on each unique amplified fragment, all of which were of the expected size. The PCR fragments are shown in FIG. 14.

The PCR primers were the following:

```
Primer 11088 (SEQ ID NO: 9):
5'-GAGATCGCTGATGGTATCGG-3'

Primer 11089 (SEQ ID NO: 10):
5'-TCTACACCACGCCGAACACC-3'
```

This analysis showed that one out of the six double recombinants tested had undergone the allele exchange. This new strain, named TEX1pir42, was further evaluated for its ability to replicate pCOR plasmids compared to the parental strain TEX1.

2) Evaluation of TEX1pir42 pCOR plasmids were transformed in parallel into TEX1 and TEX1pir42 and grown overnight in 2 ml of selective M9 medium. Then, the plasmid DNA was extracted with the Wizard SV plus minipreps kit (Promega) to evaluate the relative plasmid copy number and topology of the pCOR plasmids in both strains.

Figure 15:
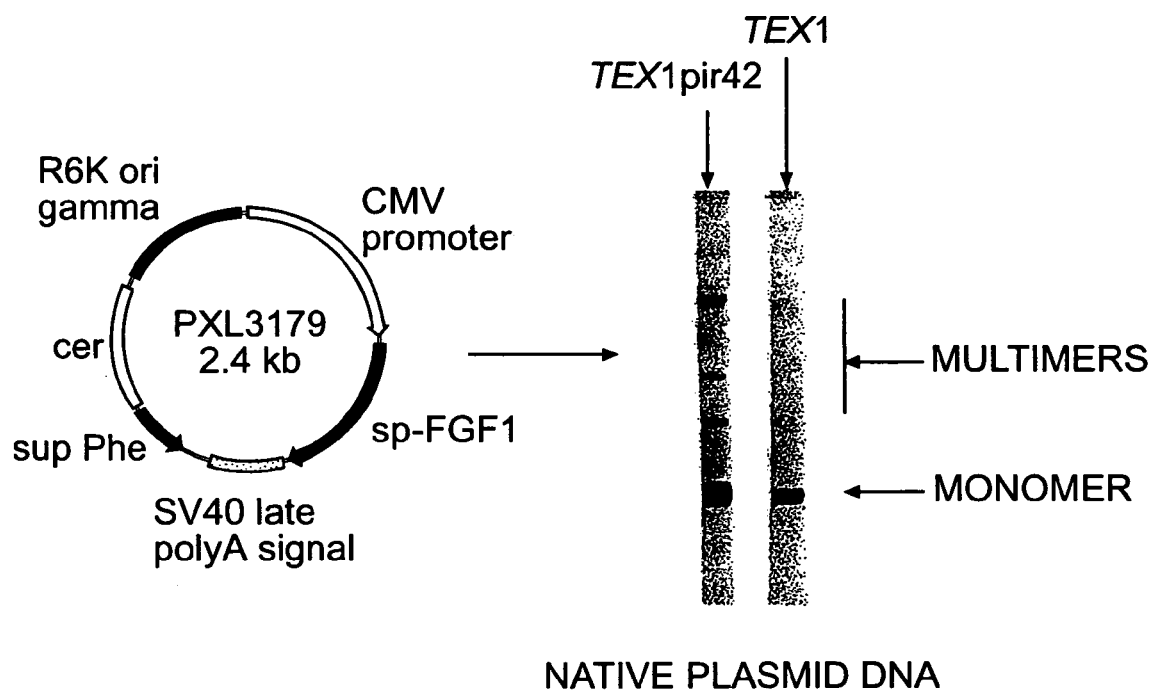
FIG. 15: Agarose gel electrophoresis showing the topology of pCOR plasmid pXL3179 produced in TEX1 or TEX1pir42.

A 2-fold increase in copy number was obtained reproducibly in TEX1pir42 transformed with the pCOR plasmid pXL3516 (2.56 kb). To further characterize TEX1pir42, the copy number and topology of pCOR plasmids such as pXL3179 and pXL2774 were evaluated by agarose gel electrophoresis analysis after small scale purification of plasmid DNA (4 to 6 clones/strain). Copy number was evaluated on plasmids linearized with EcoRI restriction enzyme. A topology test was run on non-digested plasmids, in the absence of ethidium bromide. The resulting agarose gel is displayed in FIG. 15, and clearly shows a higher plasmid copy number when the plasmid pXL3179 was produced in TEX1pir42, than when produced in TEX1 strain. FIG. 15 also displays the topology of the plasmid pXL3179, and shows that an increase in plasmid copy number, which were essentially in the form of monomers, with few plasmids in the form of multimers. The results obtained with these pCOR plasmids are also summarized in Table 5. Relative copy number was calculated in comparison with the same plasmid in TEX1. A 2-3 fold increase in plasmid copy number was observed with plasmids pXL3179 and 2774 produced in TEX1pir42.

TABLE 5

Replication and copy number of pCOR plasmids produced in TEX1*pir42*

| PLASMIDS | SIZE (kb) | RELATIVE COPY NUMBER* |
|---|---|---|
| pXL3179 | 2.4 | x3 |
| pXL2774 | 4.5 | x2 |

*copy number was compared to the same plasmid in TEX1.

EXAMPLE 11

Comparative Experiments: Construction of TEX1cop21 (XAC-1endA-traD-pir116cop21)

1) Construction of TEX1cop21

The TEX1cop21 strain was constructed similarly as that described in Example 10 for TEX1pir42. The following oligonucleotides used to introduced cop21 into the pir116 gene by directed mutagenesis were as follows:

Sense oligonucleotides: 11153 (SEQ ID NO: 11)

```
5'-CG CAA TTG TTA ACG TCC AGC TTA CGC TTA AGT AGC C-3'
                        cop21
```

Antisense oligonucleotide: 11154 (SEQ ID NO: 12)
5'-G GCT ACT TAA GCG TAA GCT GGA CGT TAA CAA TTG CG-3'

The cop21 mutation was introduced as a TCC serine codon instead of the TCA serine codon to eliminate a HindIII restriction site close to the mutation.

Figure 16:
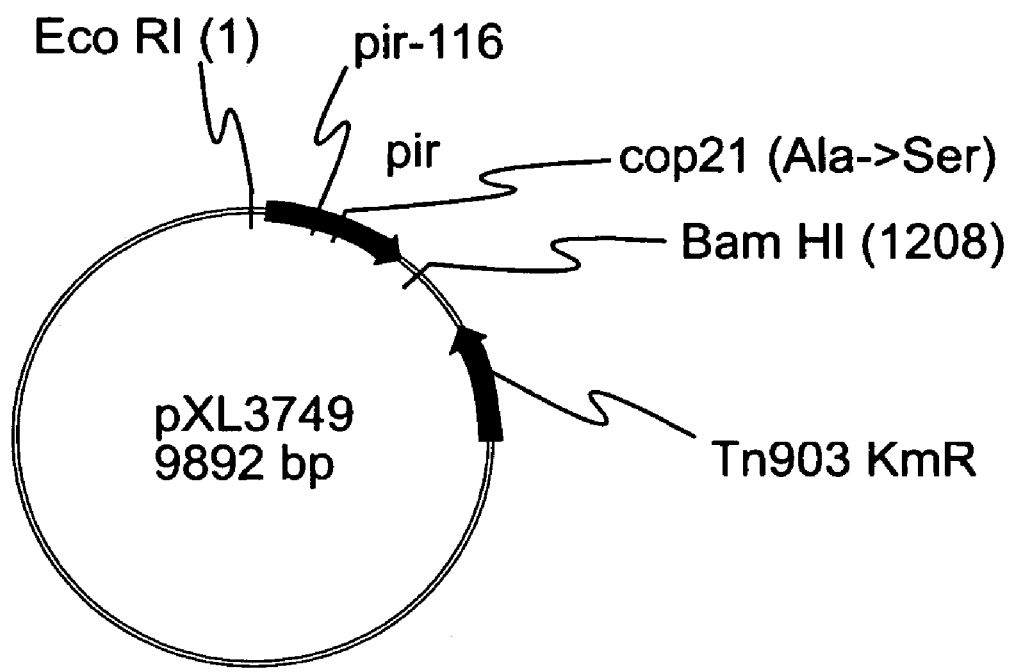
FIG. 16: Schematic representation of the pXL3749 suicide plasmid carrying pir116cop21 gene.

The template used for directed mutagenesis was pXL3395 (see FIG. 13). The resultant plasmid named pXL3432 was used to construct the suicide M13 vector in a similar way as to what is shown for pir42 in FIG. 13. The suicide vector pXL3749 is shown in FIG. 16.

The E. coli clones obtained after homologous recombination with pXL3749 were screened by PCR and subsequent restriction with HindIII and sequencing to monitor the cop21 and pir116 mutations. One clone out of the six double recombinants tested had undergone the gene replacement. The resulting strain was named TEX1cop21.

2) Evaluation of TEX1cop21

Figure 17:
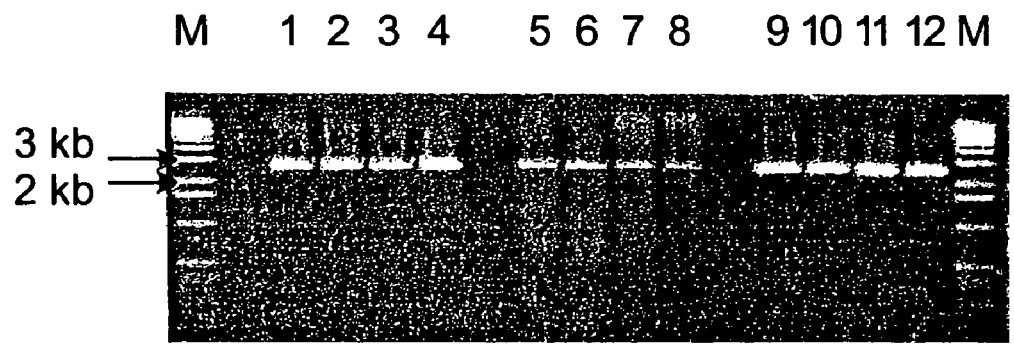
FIG. 17: Agarose gel electrophoresis showing the plasmid copy number of pXL2979 when produced in E. coli host cell TEX1cop21 (lines 1-4), in E. coli host cell XAC1pir (lines 5-8), in E. coli TEX1 (lines 9-12).

TEX1cop21 was transformed by various pCOR plasmids, including pXL2979, a 2.5 kb Km$^R$ pCOR vector (See Example 7.1), and assayed for increased copy number by gel electrophoresis. Such an experiment with pXL2979 is shown in FIG. 17. Plasmid DNA from four independent clones for each strain prepared with Promega miniprep kit was linearized with EcoRI, electrophoresed on agarose gel and then stained with ethidium bromide. Each sample represented a similar amount of bacteria, as measured by optical density at 600 nm. The agarose gel electrophoresis obtained for the pCOR plasmid pXL2979 produced in *E. coli* TEX1cop21, XAC1pir, and TEX1 is displayed in FIG. 17. It clearly shows there was no increase in plasmid copy number when the plasmids are produced in the TEX1cop21 strain, as compared with TEX1.

EXAMPLE 12

Construction of TEX2pir42 (XAC-1pir116 pir42 recA⁻)

Firstly, a recA– derivative of TEX1 was constructed. The pir42 mutation was then introduced into the resulting strain named TEX2 to generate TEX2pir42.

1) Construction of *E. Coli* TEX2, a recA– Derivative of TEX1

A deleted recA gene containing 3 translation stop codons (one in each frame) at its 5' end was obtained by PCR. This deleted recA gene was introduced by gene replacement (Blum et al., *J. Bacteriol.*, 1989, 171, pp. 538-46) into the TEX1 genome. The construction of the suicide vector for homologous recombination is shown in FIG. 18. PCR primers used for the amplification of recA fragments are shown in the following Table 6:

TABLE 6

| primers | DNA sequences |
|---|---|
| seq 10930 SEQ ID NO: 13 | 5'CCCT<u>CTAGA</u>TCGATAGCCATTTTTACTCCTG 3' |
| seq 10931 SEQ ID NO: 14 | 5'CG<u>GGATCC</u>TGATTATGCCGTGTCTATTAG 3' |
| seq 10932 SEQ ID NO: 15 | 5' CCC<u>AAGCTT</u>CTTCGTTAGTTTCTGCTACGCCTTCGC 3' |
| seq 10933 SEQ ID NO: 16 | 5'GG<u>TCTAGA</u>ACGTGAAAGTGGTGAAGAACAAAATCG 3' |

Restriction sites added to the recA sequence are underlined.

To maintain the RecA+ phenotype necessary for homologous recombination to occur, the recA function was provided to *E. coli* TEX1 with a plasmid containing a heterologous recA gene that can complement *E. coli* recA mutants, such as for example the recA gene of the bacterium *Agrobacterium radiobacter*, and an antibiotic gene resistance, such as the ampicillin resistance gene. After gene replacement, the plasmid was eliminated from the recombinant strain by culture-dilution in non-selective medium (LB). The absence of the plasmid was screened for the loss of antibiotic resistance.

Figure 19:
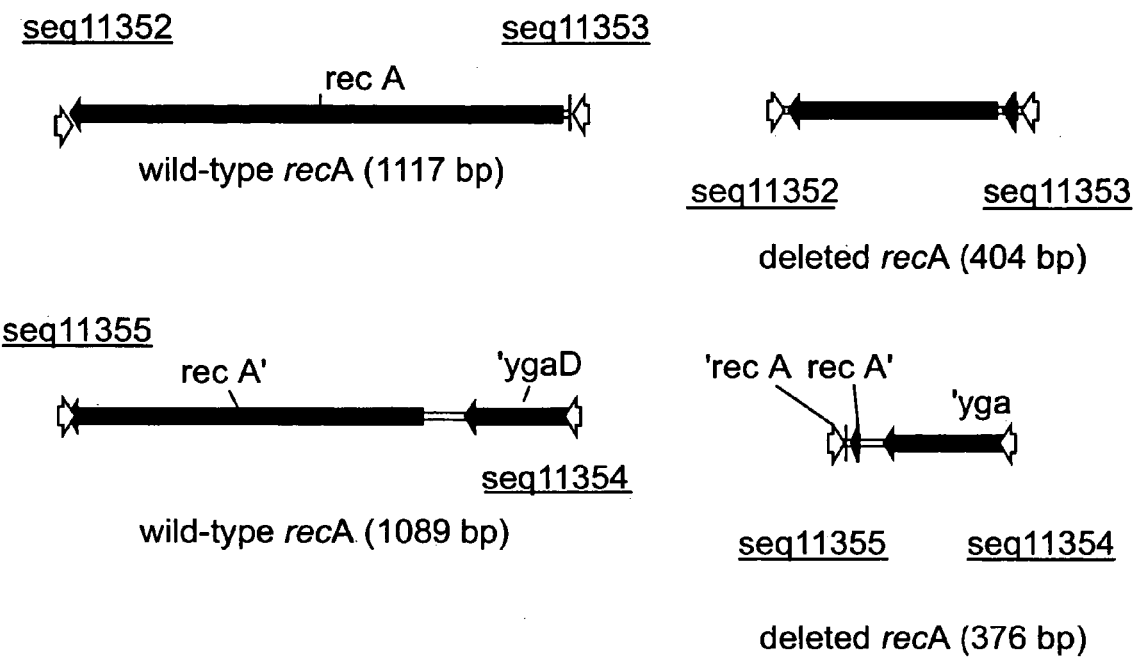
FIG. 19: Schematic representation of the PCR products obtained when amplifying regions of E. coli TEX2 strain.

The resulting strain was named TEX2. Gene replacement was monitored by PCR in FIG. 19. PCR Primers are described in the following Table 7.

TABLE 7

| | Primers 11355-11354 | Primers 11355-11354 |
|---|---|---|
| Wild type recA | 1117 bp | 1089 bp |
| Deleted recA | 404 bp | 376 bp |

The first primer was based on the sequence of the recA gene. The second one was based on a sequence close to but outside the homology region present in the suicide vector pXL3457 (immediately 5' or 3' of recA) to ensure that amplification can only occur on a genomic fragment. The sequence of both oligonucleotides was chosen according to the sequence of *E. coli*, which comprises the recA locus (Genbank ECAE000354).

The PCR fragments obtained from a recA-deleted strain were shorter as compared to those obtained with a wild-type strain, as presented in the following Table 8.

TABLE 8

PCR primers for amplication of recA

| primers | 5'->3' sequence |
|---|---|
| seq 11352 - SEQ ID NO: 17 | GCGACCCTTGTGTATCAAAC |
| seq 11353 - SEQ ID NO: 18 | GGTATTACCCGGCATGACAG |
| seq 11355 - SEQ ID NO: 19 | GTGGTGGAAATGGCGATAGG |
| seq 11354 - SEQ ID NO: 20 | GCGATTTTGTTCTTCACCAC |

The PCR profile obtained was as expected and demonstrated the presence of a truncated recA gene in the genome of TEX2. The recA– phenotype (sensitivity to UV light), as well as phenotypic characteristics of TEX2, were checked. Phenotypic characteristics of TEX2 were the same as those of TEX1 strain, i.e., ara–, Rif$^R$, Nal$^R$, Sp$^R$, UidA–, Arg–, Km$_S$ Amp$^S$), as expected.

B) Construction of *E. Coli* TEX2pir42

A TEX2pir42 strain was constructed by double homologous recombination, according to the strategy described in Example 10, with the exception that recombination in TEX2 was carried out in presence of a plasmid carrying a heterologous recA gene capable of complementing the *E. coli* recA mutants, in order to maintain a recA+ phenotype required for homologous recombination.

Gene replacement was monitored by restriction analysis of the PCR product digested with ClaI (see FIG. 14). Gene replacement had occurred in two out of the four-studied double recombinant clones.

C) Evaluation of *E. Coli* TEX2pir42

Figure 20:
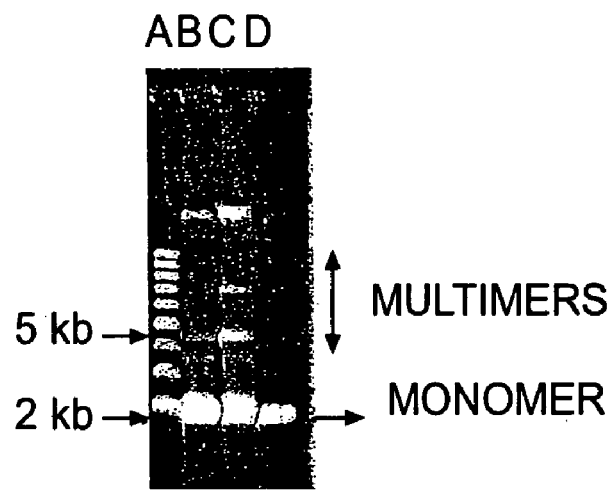
FIG. 20: Agarose gel electrophoresis showing the topology of pCOR pXL3179 produced in E. coli TEX2pir42 (line B), in E. coli TEX1pir42 (line C), in E. coli TEX1 (line D).

1) Evaluation at Lab Scale Plasmid Production:

TEX2pir42 was transformed by the pCOR plasmid pXL3179 (2.4 kb). Production of pXL3179 in TEX2pir42 was intensively studied at the lab scale, in terms of reproducibility of the improvement of plasmid copy number, conditions of culture, as well as stability (number of generations). All the studies consistently showed a 2 to 5-fold increase of plasmid copy number as compared to production of pXL3179 in TEX1 under the same conditions. Plasmid copy number was assessed further to the production of pXL3179 in TEX2pir42, and TEX1pir42 and TEX1 as comparative experiments. In this experiment, plasmids were extracted from identical bacterial biomass, based on the OD at 600 nm, and analyzed by agarose gel electrophoresis. The gel was stained with ethidium bromide after electrophoresis. The agarose gel electrophoresis, which is displayed in FIG. 20, clearly shows that plasmids are produced in TEX2pir42 at high copy number, and advantageously shows that plasmid multimers are reduced when produced in TEX2pir42 instead of TEX1pir42.

2) Evaluation in Fermenters:

These results were confirmed at a larger scale in 7-liter fermenters, as described below.

a) Composition of Fermentation Media

The composition of the medium used for inoculum cultures was: $Na_2HPO_4$ 6 g/l, $KH_2PO_4$ 3 g/l, NaCl 0.5 g/l, $NH_4Cl$ 1 g/l, $NH_4H_2PO_4$ 3 g/l, glucose 5 g/l, $MgSO_4, 7H_2O$ 0.24 g/l, $CaCl_2, 2H_2O$ 0.015 g/l, thiamine HCl 0.010 g/l.

The composition of the medium used for fed-batch culture was as follows: $KH_2PO_4$ 8 g/l, $K_2HPO_4$ 6.3 g/l, $Na_2HPO_4$ 1.7 g/l, $NH_4Cl$ 2.5 g/l, glucose 10 g/l, $MgSO_4, 7H_2O$ 2.6 g/l, thiamine 0.011 g/l, Biospumex36 antifoam 0.1 ml/l, salt mix (see table 9) 2.5 ml/l.

TABLE 9

Composition of salt mix

|  | Salt mix Solution (g/100 ml) | Final concentration in fed-batch medium |
|---|---|---|
| $FeSO_4, 7H_2O$ | 1.6 | 40 |
| $CaCl_2, 2H_2O$ | 1.6 | 40 |
| $MnSO_4, H_2O$ | 0.4 | 10 |
| $CoCl_2, 6H_2O$ | 0.16 | 4 |
| $ZnSO_4, 7H_2O$ | 0.08 | 2 |
| $MoO_4Na_2, 2H_2O$ | 0.072 | 1.8 |
| $CuCl_2, 2H_2O$ | 0.04 | 1 |
| $H_3BO_3$ | 0.02 | 0.5 |
| $AlCl_3, 6H_2O$ | 0.04 | 1 |

The composition of the supply medium was as follows: 50% glucose, 0.7%, magnesium 0.02% thiamine-HCl, 1% Biospumex36 antifoam.

b) Fermentation Parameters

A 7-liter fermenter containing 3 liters of the fed-batch medium was inoculated with 1.2% of the inoculum culture. Inoculum was prepared as follows: 250 ml of the inoculum medium in a 2-liter flask was inoculated with 0.25 ml of a frozen cell suspension of the E. coli strain TEX2pir42 (pXL3179).

Flasks were incubated for 24 hours at 37° C. at 220 rpm. After 24 hours, different parameters were measured: residual glucose: 0 g/l, $OD_{600nm}$ was 2.7 and pH 6.24. During fermentation, the pH was controlled and adjusted automatically between 6.9 and 7 with $NH_3$. The temperature was maintained at 37° C. and the dissolved oxygen adjusted to a 45% pO2 by retroaction on the stirring rate.

After initial batch culturing of the bacterial strain for about 17 hours and consumption of the carbon source (glucose), the supply medium was added. Glucose and acids, such lactate and acetate, were maintained at a concentration close to 0.

c) Results

Final results are presented in Table 10, as compared to production in a 100-liter fermenter with E. coli TEX1 (pXL3179) in optimized conditions.

As for XAC-1pir116, there was no difference between 7-liter and 800-liter fermenters in terms of plasmid copy number of pXL3179 produced in TEX 1.

Plasmids pXL3179 produced in a 7-liter fermenter using a E. coli TEX2pir42 was compared to the production of pXL3179 in a 100-liter fermenter with E. coli TEX1, in optimized conditions. It was demonstrated that as for XAC-1pir116 (See Example 5.3), there is a stable plasmid production rate in a 7-liter, 100-liter, or 800-liter fermenter in TEX1.

TABLE 10

Characteristics of the fermentation of TEX1 and TEX2pir42 strains containing pXL3179.

|  | Reference | Duration of fermentation (h) | Final OD (600 nm) | Cell Dry weight | Concentration of DNA (mg/l) | Estimated copy number (copy/bacterium) |
|---|---|---|---|---|---|---|
| TEX1 (pXL3179) | OpGen090 | 43.00 | 104 | 33.1 | 96 | 616-627 |
| TEX2pir42 (pXL3179) | Op1328S5 | 48.47 | 72 | 27.1 | 205 | 1896-1904 |

There were 3-fold more copies of plasmid pXL3179 per bacterium in TEX2pir42 as compared to TEX1.

Figure 21:
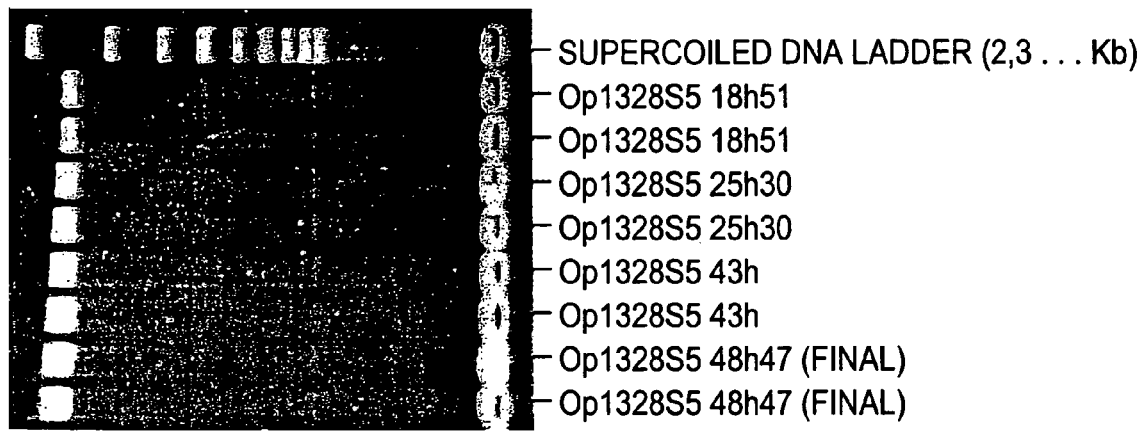
FIG. 21: Analysis of plasmid pXL3179 produced by fermentation in E. coli TEX2pir42.

Plasmids corresponding to different fermentation time points were extracted from identical bacterial biomass, based on the OD at 600 nm, and analyzed by agarose gel electrophoresis. FIG. 21 clearly shows an increase of the plasmid copy number with the duration of the fermentation. Also, FIG. 21 shows the topology of the pXL3179 plasmid produced in Op1328S5 TEX2pir42, which was nearly exclusively in a monomeric form.

In conclusion, the E. coli host strain TEX2pir42 according to the present invention provided an unexpectedly high plasmid copy number improvement of pCOR plasmids, such as pXL3179, of 2 to 5-fold in TEX2pir42 as compared to TEX1, at a lab scale and in fermenters. Furthermore, while the plasmid copy number was greatly improved, plasmids so produced exhibited a monomeric topology, not only at lab-scale but also at a larger scale (7-liter fermenter) compatible with industrial production.

EXAMPLE 13

New Copy-Up Mutants of pir116 Identified by a Novel Fluorescence-Based Screening Method To increase pCOR plasmid copy number in bacterial host cells, we have mutagenized the pir116 gene, which encodes a copy-up mutated version of the pir gene. To date all of the mutations increasing the copy number of R6K-derived plasmids, such as embodiments of pCOR, have been found within the pir gene.

After random mutagenesis by PCR, mutated pir116 genes were introduced into a pCOR vector containing the cobA reporter gene, which is described below. After fluorescence based screening, the copy number and topology of the selected mutant plasmid were evaluated. We obtained three different mutants of pir116 gene that increase plasmid copy number. These novel mutations have not been described previously.

A classical screening method for copy-up mutants is based on antibiotic resistance. In this method, the level of resistance of a host bacterium to an antibiotic is a function of the copy number of an antibiotic resistance gene located on a plasmid within the cell. As the copy number of the plasmid, and therefore the antibiotic resistance gene, increases, the level of antibiotic resistance also increases. This method, however, was not applicable for R6K-derived plasmids in host cells containing the pir116 mutation due to a too high baseline copy number of the plasmid (about 400 copies/cell) in these cells. Accordingly a new screening method based on fluorescence to identify copy-up mutations of the pir116 gene was developed.

For this new method, the cobA gene was introduced into a pCOR vector to provide a simple means of monitoring improvement in plasmid copy number. The cobA gene was obtained from *Pseudomonas denitrificans* (Crouzet et al., J. Bacteriol, 172:5968-79 (1990)). It encodes uroIII methyltransferase, an enzyme of the vitamin B12 pathway that adds two methyl groups to the urogen III molecule. When overexpressed in *E. coli*, cobA leads to the accumulation of red products that are fluorescent under near UV light. When exposed to UV, bacterial colonies overexpressing this gene appear pink to red. We tested this gene to determine if it could serve as a reporter gene for plasmid copy number in the pCOR system.

To evaluate the relationship between plasmid copy number and level of fluorescence of transformed bacteria exposed to UV light a control plasmid (pXL3767) was constructed comprising cobA deleted of its own promoter (FIG. 22). This plasmid was transformed into three different host strains (XAC1pir, XAC1pir116 and TEX1pir42). These strains were selected based on previous experiments showing that the average copy number of a pCOR plasmid in XAC1pir is 1, it is approximately five to ten fold higher in TEX1, and 15 to 30 fold higher in TEX1pir42.

Recombinant colonies were streaked on M9 minimal medium and exposed to UV light on a transilluminator as shown in FIG. 22. We observed that the fluorescence intensity of the colonies was positively correlated with the plasmid copy number, with XAC1pir116 exhibiting more fluorescence than XACpir, and TEX1pir42 exhibiting more fluorescence than XAC1pir116.

The results shown in FIG. 22 demonstrate that this fluorescence-based assay method easily discriminates between the tested plasmid copy numbers, especially between the plasmid copy number found in strains TEX1 and TEX1pir42. That is, the intensity of red fluorescence observed in this assay increases with the plasmid pCOR-cobA copy-number.

Having demonstrated a positive correlation between fluorescence and cobA copy number, we constructed a plasmid into which mutagenized pir116 genes were introduced for screening. Four plasmids with different combinations of constitutive modules, as shown in FIG. 23, were constructed and tested. One of these plasmids demonstrated a significantly different level of fluorescence when transformed into pir116 and pir116pir42 isogenic strains. This plasmid, pXL3830, is shown in pertinent part in FIG. 24.

Control plasmids were used during the screening and evaluation experiments. First, a baseline level control plasmid, pXL3830, containing "wild type" pir116 was used to set a baseline fluorescence level. Second, pXL3795, that contains the double mutation pir116-pir42 which increases the copy number of the plasmid by 4 to 6 as compared to pXL3830, was used as a positive control.

Random mutagenesis was performed on pir116 gene using the Diversify PCR random mutagenesis kit (BD Biosciences Clontech, Palo Alto, Calif., USA). Condition 1, which introduced an average of 2 mutations per 1000 base pairs, was used. A preliminary experiment run using "condition 1" has shown by sequencing of 12 mutants that the mutation rate was actually about 2 mutations in the pir116 gene. The pir116 gene was amplified as an EcoRI-SstI fragment with oligonucleotides C8832 (5-CTTAACGGCT-GACATGGGAATTC-3') (SEQ ID NO: 23) and C8833 (5'-CGATGGGCGAGCTCCACCG-3') (SEQ ID NO: 24). After digestion with EcoRI and SstI, the mutagenized fragment containing pir 16 was cloned into pXL3830 in place of the "wild-type" pir116 gene.

Figures 24, 25:
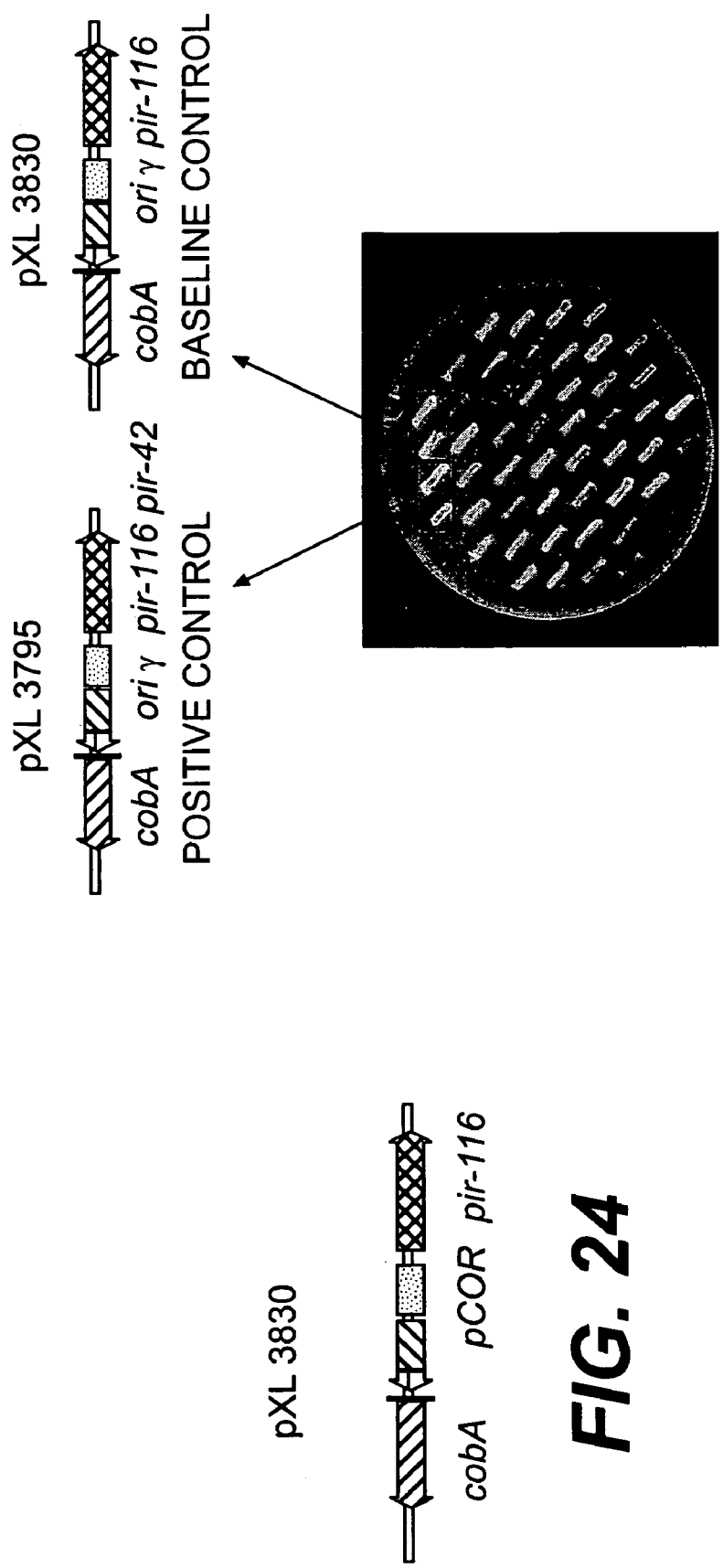
FIG. 24: Diagram of plasmid pXL3830.
FIG. 25: Agar plate demonstrating fluorescence-based screening for copy-up mutants generated by random mutagenesis.

Plasmids carrying mutagenized pir116 ("pir116*") were transformed into *E. coli* strain XAC-1, the parent of pCOR host XAC1pir116. Transform ants were screened for increased fluorescence under UV light and compared to XAC1(pXL3830) and XAC1(pXL3795) controls. A duplicate plate was not exposed to UV to minimize secondary mutations. A representative screening plate under UV light is shown in FIG. 25.

The following flow chart summarizes the results of the screening experiment.

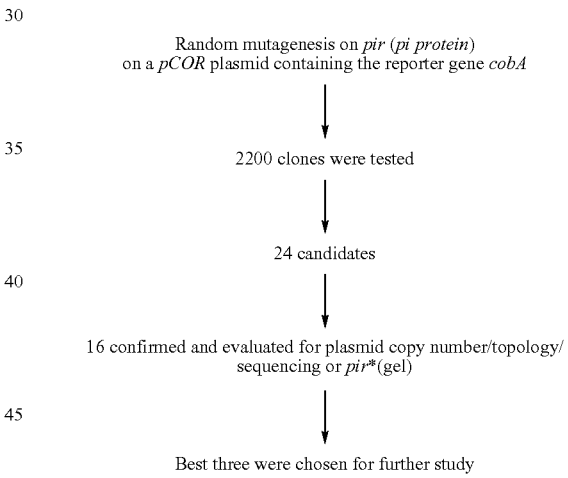

Figure 26:
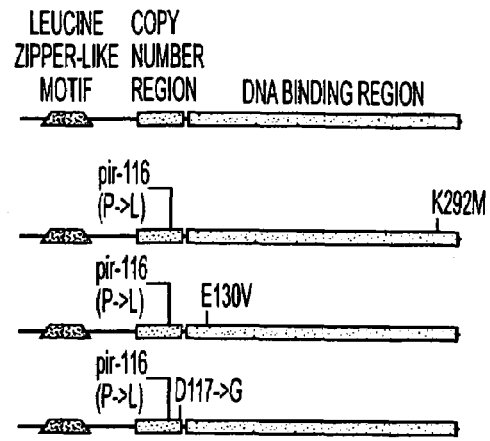
FIG. 26: Evaluation of copy-up mutants identified by the fluorescence-based screening method.

The evaluation of the three selected mutants is summarized in FIG. 26. Each mutant showed an increase in copy number as compared to the pir116 plasmid. In the case of mutants 114C and 100B, the plasmid was essentially in monomeric form. This could be an advantage as compared to a pir116pir42 plasmid, which has an increased copy number and a high multimer content, like mutant 201C.

The pir116* gene of each mutant was sequenced. Each clone contains a single non-isocodant mutation in pir116 ORF. All three of the mutations affect the C terminus of the pi protein, which is involved in DNA binding. None of these mutations have been described before.

Figure 27:
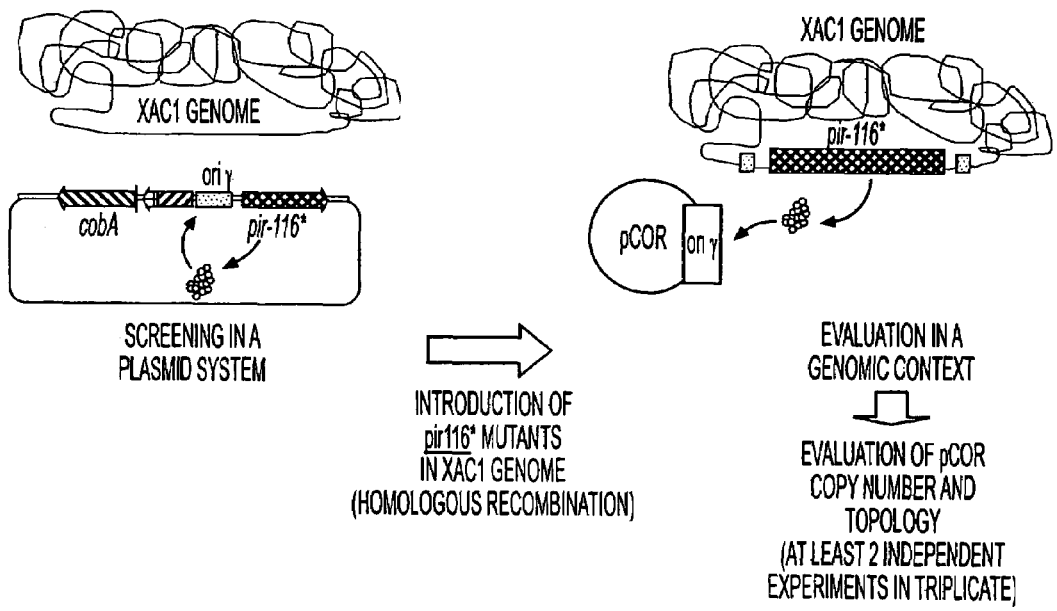
FIG. 27: Diagram of the strategy for evaluating pir116 mutants inserted into the bacterial genome.

Once detected by screening in a plasmid system, these mutations were evaluated in a production system, that is, where the pir116* gene is introduced into the genome of an *E. coli* pCOR host strain. The strategy for this evaluation is summarized in FIG. 27. For this evaluation, plasmid pXL3179 plasmid was transformed into each of the three *E.* coli strains bearing the mutations identified in FIG. 26, and assessed for plasmid copy number and topology. The results of these experiments are presented in FIG. 28. It was observed that plasmid copy number was significantly increased relative to XAC1pir116 only for 201 C mutant.

EXAMPLE 14

Minicircle with M13 Gene III as a Tool for Integration by Homologous Recombination in E. Coli 1. Suicide Vectors Gene replacement by double homologous recombination in E. coli requires the use of a suicide vector. These vectors are constructed and produced in a host capable of replicating them and used subsequently for recombination into the chromosome of a host unable to replicate them.

Bacteriophage M13 is a very useful genetic tool that can be used in rep mutants (Metcalf, W., W. Jiang, et al., Gene 138:1-7 (1994)) or in non-suppressor strains of E. coli when M13 mp8 through 11 are used (Blum, P. et al., J. Bacteriol., 171:538-46 (1989)). Certain limitations in terms of construction, insert size, and instability are frequently encountered. Plasmids carrying the R6K gamma DNA replication origin are well known suicide vectors (Miller, V. and J. Mekalanos, J. Bacteriol., 170:2575-83 (1988)), but they are not useful for modifying E. coli strains that express the pi protein, which permits such plasmids to replicate.

A universal suicide vector was engineered with a novel counter selectable marker and used to construct E. coli strains wherein mutants of the pir116 gene (pir116*) are inserted into a bacterial genome by homologous recombination. The strategy presented here is demonstrated for mutant 114C, but has also been used to produce strains bearing other pir116* mutants.

2. Counter-Selectable Marker

Different markers can be used to select for bacteria having undergone a second recombination event. This event leads to the loss of this marker and in some cases to gene replacement after recombination between the chromosome and a suicide vector. For instance, the SacB gene from Bacillus is lethal when bacteria expressing the gene are plated on a medium containing sucrose (Ried, J. L. and A. Collmer, Gene 57:239-46 (1987)). As another example, the tetracycline resistance gene confers sensitivity to fusaric acid (Bochner, B. R., et al., J. Bacteriol. 143(2):926-3 (1980)). The infection by the bacteriophage M13 confers the sensitivity to the detergent deoxycholate (Blum, P., et al., J. Bacteriol. 171:538-46 (1989)).

Due to a lack of efficiency in some E. coli strains, a positive selection method for double recombinants was developed. Gene III from bacteriophage M13 was evaluated as a counter-selectable marker. This gene encodes a minor virion component responsible for the infectivity of the particles. When overexpressed from the multicopy plasmid pBR322, gene III confers deoxycholate sensitivity on the cells due to insertion of the gene III protein into the membrane of the bacteria (Boeke, J. D. et al., Mol Gen Genet 186:185-92 (1982)). No report indicated if this gene could be used as an efficient counter-selectable marker when present as a single copy in the genome of the E. coli. Therefore, we tested this hypothesis with a minicircle suicide vector.

3. Amplification by PCR of the Deleted Version of Gene III from M13

To reduce the size of the minicircle vector to be constructed, a deleted version of gene III (gene III') that is still able to confer sensitivity to deoxycholate (Boeke, J. D., P. Model, et al., Mol Gen Genet 186:185-92 (1982)) was chosen. It was amplified by PCR along with its own promoter from M13 mp18 (Yanisch-Perron, C., J. Vieira, et al., Gene 33:103-19 (1985)) as a BglII-XhoI fragment (see FIG. 29).

The oligonucleotides were as follows:

(SEQ ID NO: 25)
C19519: 5'-GGCAGATCTTAAACCGATACAATTAAAGG-3'
         BglII (SEQ ID NO: 26)
C19520: 5'-CCGCTCGAGTTACGATTGGCCTTGATATTCACAAAC-3
         XhoI

Figures 28, 29:
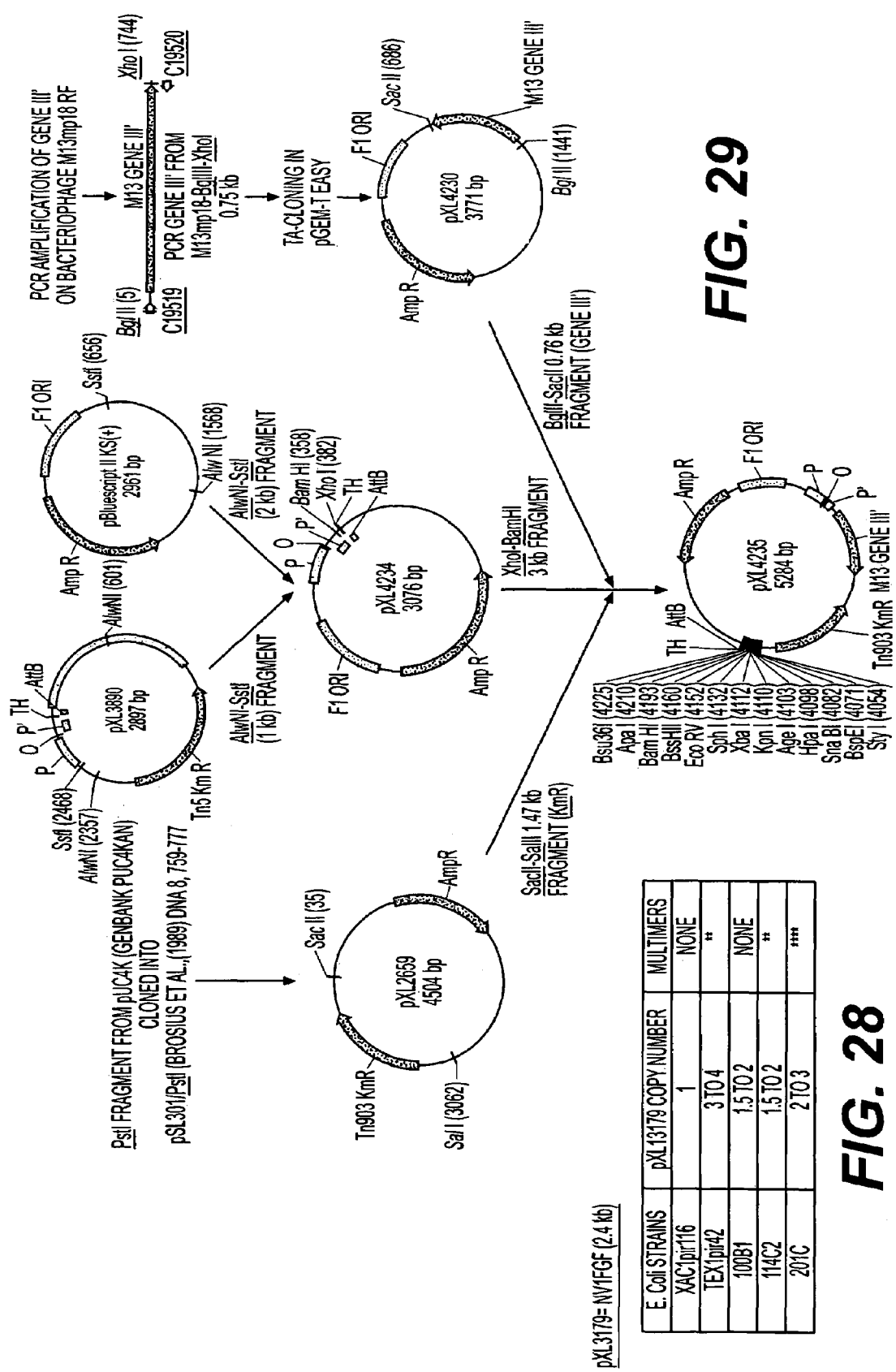
FIG. 28: Evaluation of pXL3179 copy number in different pir116* mutant E. coli strains.
FIG. 29: Construction of a plasmid used to generate minicircle vectors for homologous recombination in E. coli.

The amplified fragment was cloned by T-A cloning into pGEMT-easy (Promega Corporation, Madison, Wis., USA) to generate pXL4230 (FIG. 29). The nucleotide sequence of the insert was found to agree with that described in GenBank under accession no. VB0018. pXL4230 confers sensitivity to deoxycholate when transformed in E. coli strain DH10B (Invitrogen), indicating that it functions as expected.

4. Minicircle-Based Suicide Vector

As it does not contain any origin of replication, a minicircle plasmid may be used as a universal suicide vector. For this purpose, a selectable marker such as the kanamycin resistance gene must be added to select for a first homologous recombination event. To counter-select for bacteria that have not undergone a second event of recombination, the gene III' was added to the minicircle vector. The construction of the plasmid used to produce minicircle for recombination is shown in FIG. 29.

The minicircle is generated from a plasmid, such as pXL4235, after induction of the bacteriophage lambda integrase, which recombines between attP and attB on the plasmid (Darquet, A. M et al., Gene Ther 4(12):1341-9 (1997)). This recombinase is expressed under the control of $P_{BAD}$ in a arabinose-dependent manner in E. coli strain G6264, which is described in U.S. application Ser. No. 09/981,803. The resulting minicircle contains attL, a TH (triple-helix) forming sequence for purification, the selectable marker Tn903 kanamycin resistance gene, the counter-selectable marker gene III' and the fragment of interest for homologous recombination, cloned in the multi-cloning site of pXL4235 (FIG. 29).

As an example, the constructs used to generate E. coli strains expressing a copy-up mutation of pir116 are described in FIG. 30. These strains can be used to produce pCOR plasmids (Soubrier, F. et al., Gene Ther 6:1482-1488 (1999)). Since there is no homology between pir and the bacterial genome, the pir116* sequences were inserted into the E. coli chromosomal uidA gene, which encodes β-D-glucuronidase. This gene provides sufficient sequence similarity with the E. coli genome for homologous recombination to occur.

The protocol for the purification of minicircle and recombination occurred as follows. Plasmid pXL4256 (FIG. 30) was transformed in E. coli strain G6264 to generate G6656. Fifty ml of LB medium supplemented with ampicillin (100 mg/l) were inoculated with 0.5 ml of an overnight culture of G6656 and incubated at 37° C., with shaking at 200 rpm until the optical density at 600 nm reached 0.7. Minicircle production was induced by the addition of 250 μl of a sterile solution of 10% arabinose to the medium. After 30 minutes at 37° C., 200 rpm, total plasmid DNA was extracted using the Wizard Plus Midipreps DNA Purification system (Promega Corporation, Madison Wis., USA).

Six μg of the plasmid DNA preparation were loaded onto a 0.8% agarose preparative gel. A supercoiled DNA ladder (Promega Corporation, Madison Wis., USA) was used as a molecular weight standard. After electrophoresis overnight at 50V, the supercoiled minicircle construct (5.1 kb) was extracted and purified from the gel using an SV gel purification kit (Promega Corporation, Madison Wis., USA).

5. Double Homologous Recombination with Minicircle 4256 (uidA::pir116* Minicircle Suicide Vector)

The recombination steps for constructing the strains and the corresponding phenotypes are described in FIG. 31.

For the first recombination event (integration), 0.2, 1 and 5 μL of purified minicircle 4256 were electroporated in *E. coli* strain XAC1 (Normanly, J et al., *Proc Natl Acad Sci USA* 83:6548-52 (1986)), which is the parental strain for pCOR hosts. Kanamycin resistant colonies were obtained on LB Agar supplemented with kanamycin (50 mg/l) after overnight incubation at 37° C.

To evaluate the number of colonies potentially containing contaminant non-recombined pXL4256, 50 Km$^R$ colonies were streaked in parallel on LB Agar supplemented with kanamycin or ampicillin. Only 4 colonies out of 50 were resistant to kanamycin and ampicillin and were shown by plasmid restriction analysis to contain non-recombined pXL4256. This indicated that 46 colonies out of 50 obtained by electroporation were actually minicircle 4256 integrants.

Figure 32:
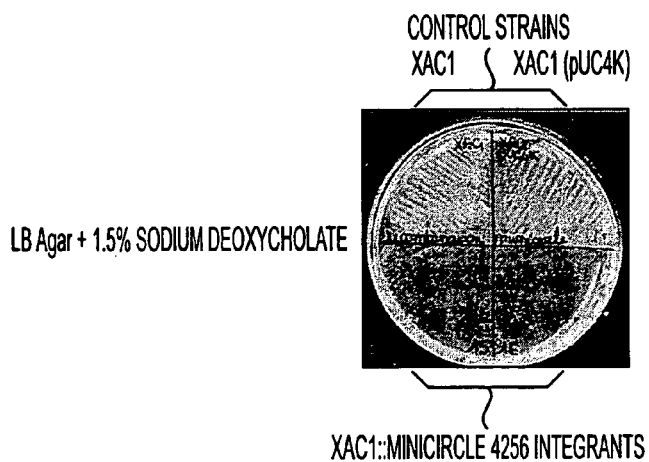
FIG. 32: Demonstration of double recombinant clones grown on medium containing sodium deoxycholate.

For the second recombination event (excision), all of the 46 Km$^R$ integrants were isolated on freshly prepared LB Agar plates containing 1.5% sodium deoxycholate ("Doc"; Sigma) and incubated at 37° C. overnight. Only a few deoxycholate-resistant (Doc$^R$) colonies (1 to 15) were obtained for each integrant, as shown in FIG. 32. This result was consistent with the selection of a relatively rare event, such as the second recombination event. 100 Doc$^R$ colonies obtained from 15 integrants were patched in parallel on LB Agar with 1.5% Doc and LB Agar plus kanamycin to screen for Doc$^R$ and Km$^S$ double recombinants. 86% of the screened colonies were Km$^S$, indicating that they had lost the suicide vector.

Figure 33A:
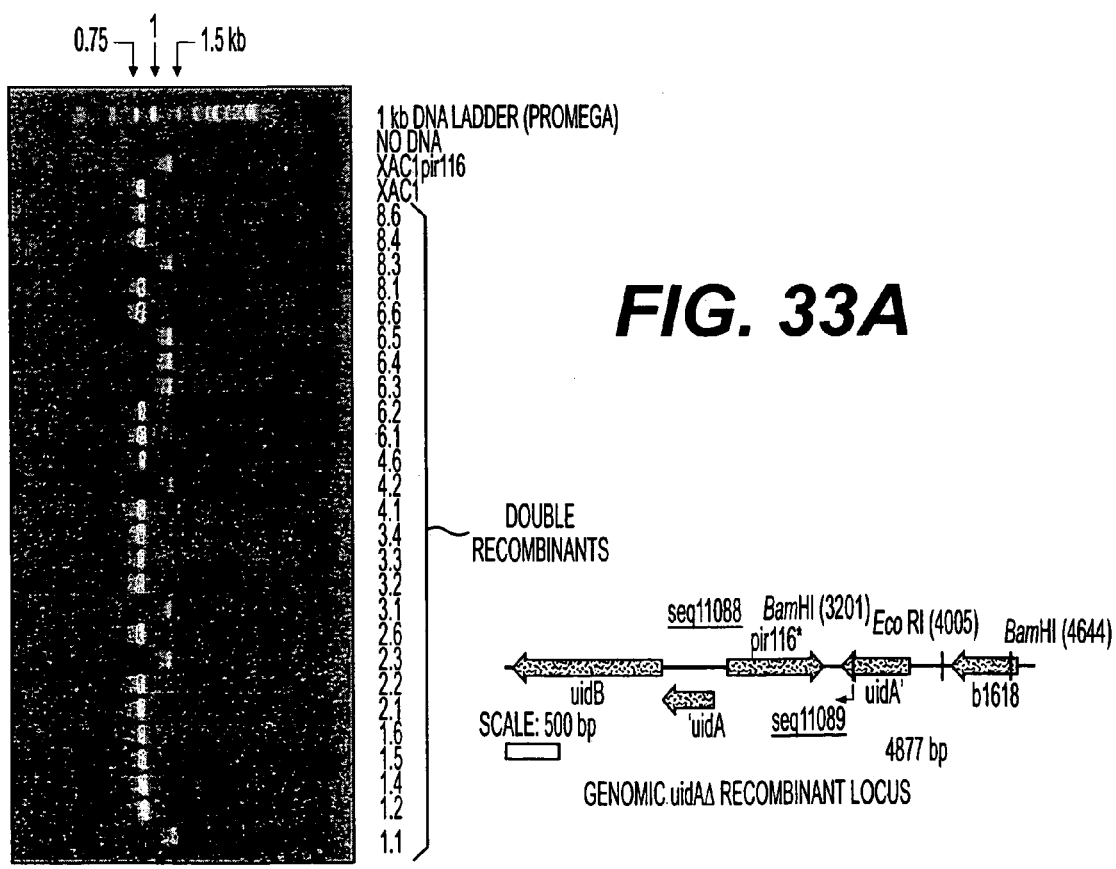
FIGS. 33A and B: The results of control PCR on double recombinants.
Figure 33B:
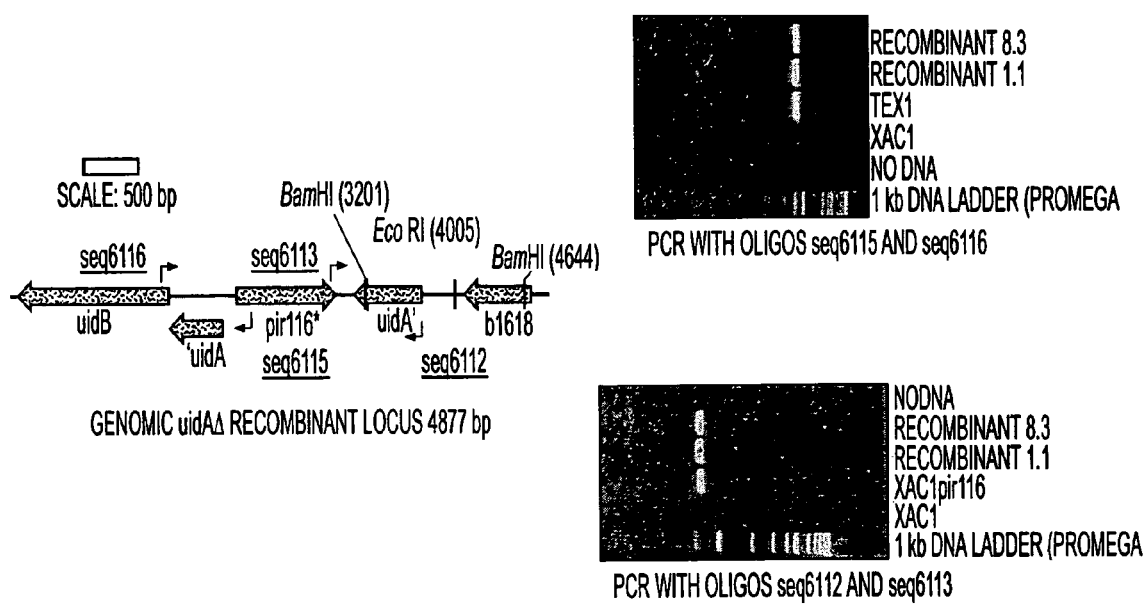

To screen for allele replacement, the chromosomal uidA locus was amplified by PCR. If allele replacement has occurred, the expected PCR fragment size is 1.3 kb. The fragment size corresponding to wild-type uidA locus, that is, without an integrated pir116* mutation, is 0.85 kb. The results presented in FIG. 33—panel A indicate that allele replacement has occurred in 30% of the double recombinants. This was confirmed by phenotypic analysis because these clones are also UidA– (beta glucuronidase–) and give white colonies on LB agar supplemented with Xgluc.

The integrity of the bacterial genome in the region close to the site of homologous recombination was checked by PCR on two independent recombinants. The first primer (seq6113 or seq6115) was based on the sequence of the pir gene and the second (seq6112 or seq6116) had a sequence based on a sequence close to, but outside of, the homology region (immediately 5' or 3' of uidA). XAC1 DNA was used as a negative control, whereas XAC1pir116 or TEX1 (Soubrier, F. et al., *Gene Ther* 6:1482-1488 (1999)) were used as positive controls.

The oligonucleotides used as PCR primers were the following:

```
                                            (SEQ ID NO: 27)
Seq11088: 5'-GAGATCGCTGATGGTATCGG-3'

(SEQ ID NO: 28)
Seq11089: 5'-TCTACACCACGCCGAACACC-3'

(SEQ ID NO: 29)
Seq6112:  5'-GACCAGTATTATTATCTTAATGAG-3'

(SEQ ID NO: 30)
Seq6113:  5'-GTATTTAATGAAACCGTACCTCCC-3'

(SEQ ID NO: 31)
Seq6115:  5'-CTCTTTTAATTGTCGATAAGCAAG-3'

(SEQ ID NO: 32)
Seq6116:  5'-GCGACGTCACCGAGGCTGTAGCCG-3'
```

The expected size for the PCR product is 0.83 kb using primers seq6112 and seq6113, and 0.88 kb when using primers seq6114 and seq6115. Results are presented in FIG. 33—panel B. The two double recombinants obtained with the minicircle suicide vector showed the expected PCR profile. This demonstrates that double homologous recombination can be easily achieved in *E. coli* using minicircle plasmids as suicide vector and the M13 gene III' as a counterselectable marker. This gene replacement technique can be directly universally carried out in any micro-organisms genetic background.

BIBLIOGRAPHY

Alting-Mees, M. A., J. A. Sorge, and J. M. Short. 1992. Methods Enzymol. 216:483-495

Blum, P., D. Holzschu, H. S. Kwan, D. Riggs, and S. Artz. 1989. J. Bacteriol. 171:538-546.

Brosius, J. 1989. Methods Enzymol. 216:469-483.

Chambers, S. P., S. E. Prior, D. A. Barstow, and N. P. Minton. 1988. Gene 68:139-149.

Chung, C. T., and R. H. Miller. 1988. Nucleic Acids Res. 16:3580.

Colloms, S. D., P. Sykora, G. Szatmari, and D. J. Sherrat. 1990 J. Bacteriol. 172:6973-6980.

Datta, N., and P. Kontomichalou. 1965. Nature 208:239-241.

Dickely, F., D. Nilsson, E. B. Hansen, and E. Johansen. 1995. Mol. Microbiol. 15:839-847.

Filutowicz, M., S. Dellis, I. Levchenko, M. Urh, F. Wu, and D. York. 1994. Prog. in Nucleic Acid Res. and Mol. Biol. 48:239-273.

Gibson, T. J. 1984. Ph. D Thesis. University of Cambridge.

Greener, A., M. Filutowicz, M. McEachem, and D. Helsinki. 1990. Mol. Gen. Genet. 224:24-32.

Herrero, M., V. de Lorenzo, and K. N. Timmis. 1990. J. Bacteriol. 172:6557-6567.

Hodgson, C. P. 1995. Bio/Technology 13:222-225.

Inuzuka, M., and Y. Wada. 1985. EMBO J. 4:2301-2307.

Jaye, M. et al., (1986) Science 233:541-5

Kleina, L. G., J. M. Masson, J. Normanly, J. Abelson, and J. H. Miller. 1990. J. Mol. Biol. 213:705-717.

Kowalczykowski, S. C., and A. K. Eggleston. 1994. Annu. Rev. Biochem. 63:9991-10043.

Leung, D. W., E. Chen, G. Cachianes, and D. V. Goeddel. 1985. DNA 4:351-355.

Maniatis, T., E. F. Fritsch, and J. Sambrook. 1989. Cold Spring Harbor Laboratory, Cold Spring Harbor, N.Y.

Meinnel, T., E. Schmitt, Y. Mechulam, and S. Blanquet. 1992. J. Bacteriol. 174:2323-2331.

Mertens, N., E. Remant and W. Fiers. (1995) Bio/Technology 13:175-179

Messing, J., and J. Vieira. 1982. Gene 19: 269-276.

Metcalf, W. W., W. Jiang, and B. L. Wanner. 1994. Gene 138:1-7.

Miller, V. L., and J. J. Mekalanos. 1988. J. Bacteriol. 170:2575-2583.

Normanly, J., J. M. Masson, L. G. Kleina, J. Abelson, and J. H. Miller. 1986. Proc. Natl. Acad. Sci. USA 83:6548-6552.

Normanly, J., L. G. Kleina, J. M. Masson, J. Abelson, and J. H. Miller. 1990. J. Mol. Biol. 213:719-726.

Roca, J. 1995. TIBS 20:156-160.

Saïki, R. K., S. Scharf, F. Faloona, K. B. Mullis, G. T. Horn, H. A. Erlich, and N. Arnheim. 1985. Science 230:1350-1354.

Sanger, F., S. Nicklen, and A. R. Coulson. 1977. Proc. Natl. Acad. Sci. USA 74:5463-5467.

Sawadogo, M., and M. W. Van Dyke. 1991. Nucleic Acids Res. 19:674.

Scott, J. R. 1984. Microbiol. Rev. 48:1-23.

Simoes, D. A., M. Dal Jensen, E. Dreveton, M. O. Loret, S. Blanchin-Roland, J. L. Uribelarrea, and J. M. Masson. 1991. Ann. N.Y. Acad. Sci. 646:254-258.

Simon, R., U. Priefer, and A. Pühler. 1983. Bio/Technology 1:784-791.

Sinha, N. D., J. Biernat, J. McManus, and H. Köster. 1984. Nucleic Acids Res. 12:4539-4557.

Stirling, C. J. G. Stewart, and D. J. Sherrat. 1988. Mol. Gen. Genet. 214:80-84.

Stirling, C. J., S. D. Colloms, J. F. Collins, G. Szatmari, and D. J. Sherrat. 1989. EMBO J. 8:1623-1627.

Studier, F. W., A. H. Rosenberg., J. J. Dunn and J. W. Dubendorff (1990). Methods Enzymol 185:60-89.

Summers, D. K., and D. J. Sherrat. 1984. Cell 36:1097-1103.

Takahashi, K., Y. Sawasaki, J. Hata, K. Mukai and T. Goto. (1990) In Vitro Cell Dev. Biol. 26:265-74.

Vieira, J., and J. Messing. 1982. Gene 19:259-268.

Wiechelman, K., R. Braun, and J. Fitzpatrick. 1988. Anal. Biochem. 175:231-237.

Yanisch-Perron, C. Vieira and J. Messing (1985) Gene 33:103-119 13.

I claim:

1. A plasmid comprising a heterologous pir gene having at least one mutation in the pir gene DNA binding region, wherein the at least one mutation is chosen from the 114C mutation, the 100B mutation, and the 201C mutation, and wherein the heterologous pir gene having at least one mutation in the pir gene DNA binding region encodes a π protein that activates a conditional origin of replication.

2. The plasmid of claim 1, further comprising at least one mutation in the pir gene leucine zipper-like motif.

3. The plasmid of claim 1, further comprising a mutation in the pir gene copy number control region.

4. The plasmid of claim 1, wherein the conditional origin of replication is from bacterial plasmid R6K.

5. The plasmid of claim 1, wherein the mutation in the DNA binding region is the 114C mutation.

6. The plasmid of claim 1, wherein the mutation in the DNA binding region is the 100B mutation.

7. The plasmid of claim 1, wherein the mutation in the DNA binding region is the 201C mutation.

8. A prokaryotic recombinant host cell comprising a heterologous pir gene and a DNA molecule comprising a heterologous gene encoding a protein, a selection gene, a target region for a site-specific recombinase, and a conditional origin of replication whose functionality in a prokaryotic host cell requires a π protein, wherein the heterologous pir gene comprises at least one mutation in the pir gene DNA binding region, wherein the at least one mutation is chosen from the 114C mutation, the 100B mutation, and the 201C mutation, and wherein the heterologous pir gene having at least one mutation in the pir gene DNA binding region encodes a π protein that activates the conditional origin of replication.

9. The prokaryotic recombinant host cell of claim 8, wherein the heterologous pir gene further comprises at least one mutation in the leucine zipper-like motif.

10. The prokaryotic recombinant host cell of claim 8, wherein the heterologous pir gene further comprises a mutation in the pir gene copy number control region.

11. The prokaryotic recombinant host cell of claim 8, wherein the heterologous pir gene is in a plasmid.

12. The prokaryotic recombinant host cell of claim 8, wherein the heterologous pir gene is in the genome of the host cell.

13. The prokaryotic recombinant host cell of claim 8, wherein the mutation in the DNA binding region is the 114C mutation.

14. The prokaryotic recombinant host cell of claim 8, wherein the mutation in the DNA binding region is the 100B mutation.

15. The prokaryotic recombinant host cell of claim 8, wherein the mutation in the DNA binding region is the 201C mutation.

16. The plasmid of claim 3, wherein the mutation in the copy number control region is pir 116.

17. The prokaryotic recombinant host cell of claim 10, wherein the mutation in the copy number control region is pir 116.

18. The prokaryotic recombinant host cell of claim 8, wherein the conditional origin of replication is from bacterial plasmid R6K.

19. The prokaryotic recombinant host cell according to claim 8, further comprising a gene comprising an amber mutation.

20. The prokaryotic recombinant host cell according to claim 8, wherein said host cell is deficient for the gene endA.

21. The prokaryotic recombinant host cell according to claim 8, wherein said host cell is deficient for the gene traD.

22. The prokaryotic recombinant host cell according to claim 8, wherein said host cell further comprises a mutated recA gene.

* * * * *

UNITED STATES PATENT AND TRADEMARK OFFICE
CERTIFICATE OF CORRECTION

| | | |
|---|---|---|
| PATENT NO. | : 7,364,894 B2 | Page 1 of 1 |
| APPLICATION NO. | : 10/684830 | |
| DATED | : April 29, 2008 | |
| INVENTOR(S) | : Fabienne Soubrier | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this

Fifth Day of October, 2010

David J. Kappos
*Director of the United States Patent and Trademark Office*

SEQUENCE LISTING

```
<160> NUMBER OF SEQ ID NOS: 39

<210> SEQ ID NO 1
<211> LENGTH: 389
<212> TYPE: DNA
<213> ORGANISM: Escherichia coli

<400> SEQUENCE: 1
tgtcagccgt taagtgttcc tgtgtcactg aaaattgctt tgagaggctc taagggcttc      60
tcagtgcgtt acatccctgg cttgttgtcc acaaccgtta aaccttaaaa gctttaaaag     120
ccttatatat tctttttttt cttataaaac ttaaaacctt agaggctatt taagttgctg     180
atttatatta attttattgt tcaaacatga gagcttagta cgtgaaacat gagagcttag     240
tacgttagcc atgagagctt agtacgttag ccatgagggt ttagttcgtt aaacatgaga     300
gcttagtacg ttaaacatga gagcttagta cgtgaaacat gagagcttag tacgtactat     360
caacaggttg aactgctgat cttcagatc                                      389

<210> SEQ ID NO 2
<211> LENGTH: 960
<212> TYPE: DNA
<213> ORGANISM: Escherichia coli

<400> SEQUENCE: 2
tatacagaat gatgaggttt ttttatgaga ctcaaggtca tgatggacgt gaacaaaaaa      60
acgaaaattc gccaccgaaa cgagctaaat cacaccctgg ctcaacttcc tttgcccgca     120
aagcgagtga tgtatatggc gcttgctccc attgatagca aagaacctct tgaacgaggg     180
cgagttttca aaattagggc tgaagacctt gcagcgctcg ccaaaatcac cccatcgctt     240
gcttatcgac aattaaaaga gggtggtaaa ttacttggtg ccagcaaaat ttcgctaaga     300
ggggatgata tcattgcttt agctaaagag cttaacctgc cctttactgc taaaaactcc     360
cctgaagagt tagatcttaa cattattgag tggatagctt attcaaatga tgaaggatac     420
ttgtctttaa aattcaccag aaccatagaa ccatatatct ctagccttat tgggaaaaaa     480
```

-continued

```
aataaattca caacgcaatt gttaacggca agcttacgct taagtagcca gtattcatct    540
tctctttatc aacttatcag gaagcattac tctaatttta agaagaaaaa ttattttatt    600
atttccgttg atgagttaaa ggaagagtta acagcttata cttttgataa agatggaaat    660
attgagtaca ataccctga ctttcctatt tttaaaaggg atgtgttaaa taaagccatt    720
gctgaaatta aaagaaaac agaaatatcg tttgttggct tcactgttca tgaaaaagaa    780
ggaagaaaaa ttagtaagct gaagttcgaa tttgtcgttg atgaagatga attttctggc    840
gataaagatg atgaagcttt ttttatgaat ttatctgaag ctgatgcagc ttttctcaag    900
gtatttaatg aaaccgtacc tcccaaaaaa gctaaggggt gatatatggc taaaatttac    960
```

<210> SEQ ID NO 3
<211> LENGTH: 24
<212> TYPE: DNA
<213> ORGANISM: Escherichia coli

<400> SEQUENCE: 3

```
gaccagtatt attatcttaa tgag                                            24
```

<210> SEQ ID NO 4
<211> LENGTH: 24
<212> TYPE: DNA
<213> ORGANISM: Escherichia coli

<400> SEQUENCE: 4

```
gtatttaatg aaaccgtacc tccc                                            24
```

<210> SEQ ID NO 5
<211> LENGTH: 24
<212> TYPE: DNA
<213> ORGANISM: Escherichia coli

<400> SEQUENCE: 5

```
ctcttttaat tgtcgataag caag                                            24
```

<210> SEQ ID NO 6
<211> LENGTH: 24
<212> TYPE: DNA
<213> ORGANISM: Escherichia coli

<400> SEQUENCE: 6

```
gcgacgtcac cgaggctgta gccg                                            24
```

<210> SEQ ID NO 7
<211> LENGTH: 36
<212> TYPE: DNA
<213> ORGANISM: Escherichia coli

<400> SEQUENCE: 7

```
gtatatggcg cttgctctca tcgatagcaa agaacc                               36
```

<210> SEQ ID NO 8
<211> LENGTH: 36
<212> TYPE: DNA
<213> ORGANISM: Escherichia coli

<400> SEQUENCE: 8

```
ggttctttgc tatcgatgag agcaagcgcc atatac                               36
```

<210> SEQ ID NO 9
<211> LENGTH: 20

```
<212> TYPE: DNA
<213> ORGANISM: Escherichia coli

<400> SEQUENCE: 9
gagatcgctg atggtatcgg                                                     20

<210> SEQ ID NO 10
<211> LENGTH: 20
<212> TYPE: DNA
<213> ORGANISM: Escherichia coli

<400> SEQUENCE: 10
tctacaccac gccgaacacc                                                     20

<210> SEQ ID NO 11
<211> LENGTH: 36
<212> TYPE: DNA
<213> ORGANISM: Escherichia coli

<400> SEQUENCE: 11
cgcaattgtt aacgtccagc ttacgcttaa gtagcc                                   36

<210> SEQ ID NO 12
<211> LENGTH: 36
<212> TYPE: DNA
<213> ORGANISM: Escherichia coli

<400> SEQUENCE: 12
ggctacttaa gcgtaagctg gacgttaaca attgcg                                   36

<210> SEQ ID NO 13
<211> LENGTH: 31
<212> TYPE: DNA
<213> ORGANISM: Escherichia coli

<400> SEQUENCE: 13
ccctctagat cgatagccat ttttactcct g                                        31

<210> SEQ ID NO 14
<211> LENGTH: 29
<212> TYPE: DNA
<213> ORGANISM: Escherichia coli

<400> SEQUENCE: 14
cgggatcctg attatgccgt gtctattag                                           29

<210> SEQ ID NO 15
<211> LENGTH: 36
<212> TYPE: DNA
<213> ORGANISM: Escherichia coli

<400> SEQUENCE: 15
cccaagcttc ttcgttagtt tctgctacgc cttcgc                                   36

<210> SEQ ID NO 16
<211> LENGTH: 35
<212> TYPE: DNA
<213> ORGANISM: Escherichia coli

<400> SEQUENCE: 16
ggtctagaac gtgaaagtgg tgaagaacaa aatcg                                    35

<210> SEQ ID NO 17
```

```
<211> LENGTH: 20
<212> TYPE: DNA
<213> ORGANISM: Escherichia coli

<400> SEQUENCE: 17
gcgacccttg tgtatcaaac                                                 20

<210> SEQ ID NO 18
<211> LENGTH: 20
<212> TYPE: DNA
<213> ORGANISM: Escherichia coli

<400> SEQUENCE: 18
ggtattaccc ggcatgacag                                                 20

<210> SEQ ID NO 19
<211> LENGTH: 20
<212> TYPE: DNA
<213> ORGANISM: Escherichia coli

<400> SEQUENCE: 19
gtggtggaaa tggcgatagg                                                 20

<210> SEQ ID NO 20
<211> LENGTH: 20
<212> TYPE: DNA
<213> ORGANISM: Escherichia coli

<400> SEQUENCE: 20
gcgattttgt tcttcaccac                                                 20

<210> SEQ ID NO 21
<211> LENGTH: 918
<212> TYPE: DNA
<213> ORGANISM: Escherichia coli

<400> SEQUENCE: 21
atgagactca aggtcatgat ggacgtgaac aaaaaaacga aaattcgcca ccgaaacgag     60
ctaaatcaca ccctggctca acttcctttg cccgcaaagc gagtgatgta tatggcgctt    120
gctctcatcg atagcaaaga acctcttgaa cgagggcgag ttttcaaaat tagggctgaa    180
gaccttgcag cgctcgccaa atcaccccca tcgcttgctt atcgacaatt aaaagagggt    240
ggtaaattac ttggtgccag caaaatttcg ctaagagggg atgatatcat tgctttagct    300
aaagagctta acctgctctt tactgctaaa aactcccctg aagagttaga tcttaacatt    360
attgagtgga tagcttattc aaatgatgaa ggatacttgt ctttaaaatt caccagaacc    420
atagaaccat atatctctag ccttattggg aaaaaaaata aattcacaac gcaattgtta    480
acggcaagct tacgcttaag tagccagtat tcatcttctc tttatcaact tatcaggaag    540
cattactcta attttaagaa gaaaaattat tttattattt ccgttgatga gttaaaggaa    600
gagttaatag cttatacttt tgataaagat ggaaatattg agtacaaata ccctgacttt    660
cctattttta aaagggatgt gttaaataaa gccattgctg aaattaaaaa gaaaacagaa    720
atatcgtttg ttggcttcac tgttcatgaa aagaaggaa gaaaaattag taagctgaag    780
ttcgaatttg tcgttgatga agatgaattt tctggcgata agatgatga agcttttttt    840 atgaatttat ctgaagctga tgcagctttt ctcaaggtat tgatgaaac cgtacctccc    900 aaaaaagcta agggggtga                                                918
```

```
<210> SEQ ID NO 22
<211> LENGTH: 305
<212> TYPE: PRT
<213> ORGANISM: Escherichia coli

<400> SEQUENCE: 22

Met Arg Leu Lys Val Met Met Asp Val Asn Lys Thr Lys Ile Arg
1               5                   10                  15

His Arg Asn Glu Leu Asn His Thr Leu Ala Gln Leu Pro Leu Pro Ala
                20                  25                  30

Lys Arg Val Met Tyr Met Ala Leu Ala Leu Ile Asp Ser Lys Glu Pro
            35                  40                  45

Leu Glu Arg Gly Arg Val Phe Lys Ile Arg Ala Glu Asp Leu Ala Ala
        50                  55                  60

Leu Ala Lys Ile Thr Pro Ser Leu Ala Tyr Arg Gln Leu Lys Glu Gly
65                  70                  75                  80

Gly Lys Leu Leu Gly Ala Ser Lys Ile Ser Leu Arg Gly Asp Asp Ile
                85                  90                  95

Ile Ala Leu Ala Lys Glu Leu Asn Leu Leu Phe Thr Ala Lys Asn Ser
            100                 105                 110

Pro Glu Glu Leu Asp Leu Asn Ile Ile Glu Trp Ile Ala Tyr Ser Asn
        115                 120                 125

Asp Glu Gly Tyr Leu Ser Leu Lys Phe Thr Arg Thr Ile Glu Pro Tyr
    130                 135                 140

Ile Ser Ser Leu Ile Gly Lys Lys Asn Lys Phe Thr Thr Gln Leu Leu
145                 150                 155                 160

Thr Ala Ser Leu Arg Leu Ser Ser Gln Tyr Ser Ser Ser Leu Tyr Gln
                165                 170                 175

Leu Ile Arg Lys His Tyr Ser Asn Phe Lys Lys Asn Tyr Phe Ile
            180                 185                 190

Ile Ser Val Asp Glu Leu Lys Glu Leu Ile Ala Tyr Thr Phe Asp
        195                 200                 205

Lys Asp Gly Asn Ile Glu Tyr Lys Tyr Pro Asp Phe Pro Ile Phe Lys
    210                 215                 220

Arg Asp Val Leu Asn Lys Ala Ile Ala Glu Ile Lys Lys Thr Glu
225                 230                 235                 240

Ile Ser Phe Val Gly Phe Thr Val His Glu Lys Glu Gly Arg Lys Ile
                245                 250                 255

Ser Lys Leu Lys Phe Glu Phe Val Val Asp Glu Asp Glu Phe Ser Gly
            260                 265                 270

Asp Lys Asp Asp Glu Ala Phe Phe Met Asn Leu Ser Glu Ala Asp Ala
        275                 280                 285

Ala Phe Leu Lys Val Phe Asp Glu Thr Val Pro Pro Lys Lys Ala Lys
    290                 295                 300

Gly
305

<210> SEQ ID NO 23
<211> LENGTH: 23
<212> TYPE: DNA
<213> ORGANISM: Escherichia coli

<400> SEQUENCE: 23
cttaacggct gacatgggaa ttc                                          23

<210> SEQ ID NO 24
```

```
<211> LENGTH: 19
<212> TYPE: DNA
<213> ORGANISM: Escherichia coli

<400> SEQUENCE: 24
cgatgggcga gctccaccg                                                  19

<210> SEQ ID NO 25
<211> LENGTH: 29
<212> TYPE: DNA
<213> ORGANISM: Bacteriophage M13mp18

<400> SEQUENCE: 25
ggcagatctt aaaccgatac aattaaagg                                       29

<210> SEQ ID NO 26
<211> LENGTH: 36
<212> TYPE: DNA
<213> ORGANISM: Bacteriophage M13mp18

<400> SEQUENCE: 26
ccgctcgagt tacgattggc cttgatattc acaaac                               36

<210> SEQ ID NO 27
<211> LENGTH: 20
<212> TYPE: DNA
<213> ORGANISM: Escherichia coli

<400> SEQUENCE: 27
gagatcgctg atggtatcgg                                                 20

<210> SEQ ID NO 28
<211> LENGTH: 20
<212> TYPE: DNA
<213> ORGANISM: Escherichia coli

<400> SEQUENCE: 28
tctacaccac gccgaacacc                                                 20

<210> SEQ ID NO 29
<211> LENGTH: 24
<212> TYPE: DNA
<213> ORGANISM: Escherichia coli

<400> SEQUENCE: 29
gaccagtatt attatcttaa tgag                                            24

<210> SEQ ID NO 30
<211> LENGTH: 24
<212> TYPE: DNA
<213> ORGANISM: Escherichia coli

<400> SEQUENCE: 30
gtatttaatg aaaccgtacc tccc                                            24

<210> SEQ ID NO 31
<211> LENGTH: 24
<212> TYPE: DNA
<213> ORGANISM: Escherichia coli

<400> SEQUENCE: 31
ctcttttaat tgtcgataag caag                                            24
```

```
<210> SEQ ID NO 32
<211> LENGTH: 24
<212> TYPE: DNA
<213> ORGANISM: Escherichia coli

<400> SEQUENCE: 32
gcgacgtcac cgaggctgta gccg                                          24

<210> SEQ ID NO 33
<211> LENGTH: 12
<212> TYPE: DNA
<213> ORGANISM: Escherichia coli

<400> SEQUENCE: 33
agaaaaaaag ga                                                       12

<210> SEQ ID NO 34
<211> LENGTH: 12
<212> TYPE: DNA
<213> ORGANISM: Escherichia coli

<400> SEQUENCE: 34 tcttttttc ct                                                        12

<210> SEQ ID NO 35
<211> LENGTH: 14
<212> TYPE: DNA
<213> ORGANISM: Escherichia coli

<400> SEQUENCE: 35
aagaaaaaaa agaa                                                     14

<210> SEQ ID NO 36
<211> LENGTH: 14
<212> TYPE: DNA
<213> ORGANISM: Escherichia coli

<400> SEQUENCE: 36
ttcttttttt tctt                                                     14

<210> SEQ ID NO 37
<211> LENGTH: 12
<212> TYPE: DNA
<213> ORGANISM: Escherichia coli

<400> SEQUENCE: 37
tctttttttc ct                                                       12

<210> SEQ ID NO 38
<211> LENGTH: 14
<212> TYPE: DNA
<213> ORGANISM: Escherichia coli

<400> SEQUENCE: 38 ttctttttttt tctt                                                    14

<210> SEQ ID NO 39
<211> LENGTH: 17
<212> TYPE: DNA
<213> ORGANISM: Escherichia coli

<400> SEQUENCE: 39
aaaaaaggga ataaggg                                                  17
```